US009273146B1

(12) United States Patent
Frank et al.

(10) Patent No.: US 9,273,146 B1
(45) Date of Patent: Mar. 1, 2016

(54) ANTI-GCC ANTIBODY MOLECULES AND METHODS FOR USE OF SAME

(71) Applicant: MILLENNIUM PHARMACEUTICALS, INC., Cambridge, MA (US)

(72) Inventors: Helen A. Frank, Sharon, MA (US); Alice Mcdonald, Swampscott, MA (US); Theresa L. O'Keefe, Waltham, MA (US)

(73) Assignee: MILLENNIUM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 14/634,438

(22) Filed: Feb. 27, 2015

Related U.S. Application Data

(62) Division of application No. 13/872,080, filed on Apr. 27, 2013, now Pat. No. 9,000,129.

(60) Provisional application No. 61/639,376, filed on Apr. 27, 2012.

(51) Int. Cl.
*C07K 16/30* (2006.01)
*C07K 16/40* (2006.01)
*G01N 33/574* (2006.01)

(52) U.S. Cl.
CPC .......... *C07K 16/40* (2013.01); *G01N 33/57492* (2013.01); *C07K 2317/56* (2013.01); *C07K 2317/565* (2013.01); *G01N 2333/988* (2013.01)

(58) Field of Classification Search
None
See application file for complete search history.

(56) References Cited

U.S. PATENT DOCUMENTS

| | | | |
|---|---|---|---|
| 5,237,051 A | 8/1993 | Garbers et al. | |
| 5,518,888 A | 5/1996 | Waldman | |
| 5,601,990 A | 2/1997 | Waldman | |
| 5,731,159 A | 3/1998 | Waldman | |
| 5,879,656 A | 3/1999 | Waldman | |
| 5,928,873 A | 7/1999 | Waldman | |
| 6,060,037 A | 5/2000 | Waldman | |
| 6,120,995 A | 9/2000 | Waldman et al. | |
| 6,268,159 B1 | 7/2001 | Waldman | |
| 6,455,251 B1 | 9/2002 | Waldman | |
| 6,602,659 B1 | 8/2003 | Waldman et al. | |
| 6,696,550 B2 | 2/2004 | LaRosa et al. | |
| 6,767,704 B2 | 7/2004 | Waldman et al. | |
| 6,942,985 B2 | 9/2005 | Waldman | |
| 7,041,786 B2 | 5/2006 | Shailubhai et al. | |
| 7,097,839 B1 | 8/2006 | Waldman | |
| 7,304,036 B2 | 12/2007 | Currie et al. | |
| 7,371,727 B2 | 5/2008 | Currie et al. | |
| 7,402,401 B2 | 7/2008 | Waldman | |
| 7,799,897 B2 | 9/2010 | Jacob et al. | |
| 7,820,390 B2 | 10/2010 | Waldman | |
| 7,854,933 B2 | 12/2010 | Waldman et al. | |
| 7,879,802 B2 | 2/2011 | Shailubhai et al. | |
| 7,910,546 B2 | 3/2011 | Currie et al. | |
| 8,034,782 B2 | 10/2011 | Shailubhai | |
| 8,067,007 B2 | 11/2011 | Waldman et al. | |
| 8,114,831 B2 | 2/2012 | Shailubhai et al. | |
| 8,206,704 B2 | 6/2012 | Waldman et al. | |
| 8,207,295 B2 | 6/2012 | Shailubhai et al. | |
| 8,357,775 B2 | 1/2013 | Shailubhai et al. | |
| 8,367,800 B2 | 2/2013 | Shailubhai | |
| 8,563,682 B2 | 10/2013 | Wolfe et al. | |
| 8,785,600 B2 | 7/2014 | Nam et al. | |
| 2003/0099656 A1 | 5/2003 | Patti et al. | |
| 2003/0147809 A1 | 8/2003 | Gudas | |
| 2003/0165496 A1 | 9/2003 | Basi et al. | |
| 2004/0031072 A1 | 2/2004 | La Rosa et al. | |
| 2004/0081651 A1 | 4/2004 | Karpusas et al. | |
| 2004/0110933 A1 | 6/2004 | Rondon et al. | |
| 2004/0258687 A1 | 12/2004 | Waldman et al. | |
| 2005/0287067 A1 | 12/2005 | Wolfe et al. | |
| 2006/0024297 A1 | 2/2006 | Wood et al. | |
| 2006/0035852 A1 | 2/2006 | Sahin et al. | |
| 2006/0246071 A1 | 11/2006 | Green et al. | |
| 2008/0124345 A1 | 5/2008 | Rothe et al. | |
| 2009/0005257 A1 | 1/2009 | Jespers et al. | |
| 2009/0041717 A1 | 2/2009 | MacDonald et al. | |
| 2011/0110936 A1* | 5/2011 | Nam et al. ............. | C07K 16/30 424/133.1 |
| 2011/0195415 A1 | 8/2011 | Waldman et al. | |
| 2011/0306055 A1 | 12/2011 | Haince et al. | |
| 2012/0251509 A1 | 10/2012 | Waldman et al. | |
| 2012/0308583 A1 | 12/2012 | Waldman et al. | |
| 2012/0321552 A1 | 12/2012 | Waldman et al. | |

(Continued)

FOREIGN PATENT DOCUMENTS

| | | | |
|---|---|---|---|
| EP | 1225844 A2 | 7/2002 | |
| WO | 9511694 A1 | 5/1995 | |

(Continued)

OTHER PUBLICATIONS

Almenoff et al., "Ligand-based histochemical localization and capture of cells expressing heat-stable enterotoxin receptors" Molecular Microbiology, 8(5), pp. 865-873 (1993).

Bakre et al., "Homologous desensitization of the human guanylate cyclase C receptor. Cell-specific regulation of catalytic activity." Eur. J. Biochem. 267:179-187 (2000).

Belisle et al., "Characterization of Monoclonal Antibodies to Heat-Labile Enterotoxin Encoded by a Palsmid from a Clinical Isolate of *Escherichia coli*", Infection and Immunity, pp. 1027-1032 (1984).

Bhandari et al., "Functional inactivation of the human guanylyl cyclase C receptor: modeling and mutation of the protein kinase-like domain." Biochemistry 40:9196-9206 (2001).

(Continued)

*Primary Examiner* — Brad Duffy
*Assistant Examiner* — Nelson B Moseley, II
(74) *Attorney, Agent, or Firm* — Finnegan, Henderson, Farabow, Garrett & Dunner LLP

(57) ABSTRACT

Antibodies and antigen-binding fragments of antibodies that bind GCC are disclosed. The invention also provides therapeutic and diagnostic methods utilizing the antibodies and antigen-binding fragments provided herein.

12 Claims, 1 Drawing Sheet

(56) References Cited

U.S. PATENT DOCUMENTS

| | | | |
|---|---|---|---|
| 2013/0315923 | A1 | 11/2013 | Waldman et al. |
| 2014/0147380 | A1 | 5/2014 | Wolfe et al. |

FOREIGN PATENT DOCUMENTS

| | | | |
|---|---|---|---|
| WO | 9742220 | A1 | 11/1997 |
| WO | 9742506 | A1 | 11/1997 |
| WO | 0173132 | A1 | 10/2001 |
| WO | 2004071436 | A2 | 8/2004 |
| WO | 2006012264 | A1 | 2/2006 |
| WO | 2010065293 | A1 | 6/2010 |
| WO | 2010096929 | A1 | 9/2010 |
| WO | 2010147684 | A1 | 12/2010 |
| WO | 2011050242 | A1 | 4/2011 |
| WO | 2011066048 | A1 | 6/2011 |
| WO | 2013016662 | A1 | 1/2013 |

OTHER PUBLICATIONS

Birbe et al., "Guanylyl cyclase C is a marker of intestinal metaplasia, dysplasia, and adenocarcinoma of the gastrointestinal tract." Hum Pathol. 36(2):170-179 (2005).

Buc et al., "Guanylyl cyclas C as a reliable immunohistochemical marker and its ligand *Escherichia coli* heat-stable enterotoxin as a potential protein-delivering vehicle for colorectal cancer cells", European Journal of Cancer, vol. 41 pp. 1618-1627 (2005).

Camci, C. et al. Peripheral blood guanylyl cyclase c (GCC) expressions are associated with prognostic parameters and response to therapy in colorectal cancer patients. Tumour. Biol. 32, 1265-1270 (2011).

Carrithers et al., "Diarrhea or colorectal cancer: can bacterial toxins serve as a treatment for colon cancer?" Proc. Natl. Acad. Sci. USA 100:3018-3020 (2003).

Carrithers et al., "*Escherichia coli* Heat-Stable Enterotoxin Receptors—A Novel Marker for Colorectal Tumors" Dis Colon Rectum, vol. 39, pp. 171-181 (1996).

Carrithers et al., "*Escherichia coli* Heat-Stable Toxin Receptors in Human Colonic Tumors" Gastroenterology vol. 107, pp. 1653-1661 (1994).

Carrithers et al., "Guanylyl cyclase C is a selective marker for metastatic colorectal tumors in human extraintestinal tissues." Proc Natl Acad Sci U S A. 93(25):14827-14832 (1996).

Chang et al., "Guanylyl cyclas C as a biomarker for targeted imagining and therapy of metastatic colorectal cancer" Biomarkers Med., 3(1), 33-45 (2009).

De Sauvage et al., "Primary structure and functional expression of the human receptor for *Escherichia coli* heat-stable enterotoxin." J Biol Chem. 266(27):17912-17918 (1991).

Debruyne et al., "Bile acids induce ectopic expression of intestinal guanylyl cyclase C Through nuclear factor-kappaB and Cdx2 in human esophageal cells." Gastroenterology 130, pp. 1191-1206 (2006).

Doronina et al., "Novel peptide linkers for hightly potent antibody-auristatin conjugate" Bioconjug Chem. 19(10): 1960-1960 (2008).

Extended European Search Report from European Serial No. 10825726 dated May 7, 2013.

Frick et al. "Guanylyl cyclase C: a molecular marker for staging and postoperative surveillance of patients with colorectal cancer" Expert. Rev. Mol. Diagn. 5, pp. 701-713 (2005).

Gali, et al. "Chemical synthesis of *Escherichia coli* ST(h) analogues by regioselective disulfide bond formation: biological evaluation of an 111In-DOTA-Phe19-STh analogue for specific targeting of human colon cancers" Bioconjug. Chem. 13, pp. 224-231 (2002).

Guarino et al., "Binding of *E. coli* heat-stable enterotoxin to rat intestinal brush borders and to basolateral membranes." Dig Dis Sci 32: 1017-1026 (1987).

Gussow et al., "Humanization of monoclonal antibodies" Methods in Enzymology, vol. 203, pp. 99-121 (1991).

Holm et al., "Functional mapping and single chain construction of the anti-cytokeratin 8 monoclonal antibody TS1" Annu. Rev. Biophys. Chem., vol. 16, pp. 139-159 (1987).

International Preliminary Report on Patenability from International Application Serial No. PCT/US13/38542 mailed Mar. 20, 2014.

International Preliminary Report on Patentability from corresponding International Application No. PCT/US10/53686 dated Mar. 10, 2011.

International Search Report from corresponding International Application No. PCT/US10/53686 dated Mar. 10, 2011.

Kloeters et al., "Uroguanylin inhibits proliferation of pancreatic cancer cells" Scandinavian J. of Gastroenterology, 43, pp. 447-455 (2008).

Knoop et al., "Pharmacologic action of *Escherichia coli* heat-stable (STa) enterotoxin." J. Pharmacol. Toxicol. Methods 28:67-72 (1992).

Liu et al., "In vivo imaging of human colorectal cancer using radiolableled analogs of the uroguanylin peptide hormone" Anticancer Research, pp. 293777-293784 (2009).

Mann et al., "Mice lacking the guanylyl cyclase C receptor are resistant to STa-induced intestinal secretion." Biochem Biophys Res Commun 239: 463-466 (1997).

Mao et al., "Ectopic expression of guanylyl cyclase C in gastric cancer as a potential biomarker and therapeutic target" Journal of Digestive Diseases, vol. 10, pp. 272-285 (2009).

McCallum et al., "Antibody-antigen Interactions: Contact Analysis and Binding Site Topography" J. Mol. Biol., vol. 262 (5) pp. 732-745 (1996).

Nandi et al., "Epitope conservation and immunohistochemical localization of the guanylin/stable toxin peptide receptor, guanylyl cyclase C." J. Cell. Biochem. 66:500-511 (1997).

Nandi et al., "Expression of the extracellular domain of the human heat-stable enterotoxin receptor in *Escherichia coli* and generation of neutralizing antibodies." Protein Expr. Purif. 8:151-159 (1996).

Nandi et al., "Topological mimicry and epitope duplication in the guanylyl cyclase C receptor." Protein Sci. 7:2175-2183 (1998).

Park et al., "Ectopic Expression of Guanylyl Cyclas C in Adenocarcinomas of the Esophagus and Stomach", Cancer Epidermiol Biomarkers Prev, vol. 11, pp. 739-744 (2002).

Pitari et al., "Bacterial enterotoxins are associated with resistance to colon cancer." Proc Natl Acad Sci USA 100: 2695-2699 (2003).

Pitari et al., "Interruption of homologous desensitization in cyclic guanosine 3',5'-monophosphate signaling restores colon cancer cytostasis by bacterial enterotoxins." Cancer Res. 65(23):11129-11135 (2005).

Rudikoff et al., "Single Amino acid substitution altering antigen-binding specificity" Proc. Natl. Acad. Sci., USA vol. 79, pp. 1979-1983 (1982).

Sargent et al., "Evaluation of guanylyl cyclase C lymph node status for colon cancer staging and prognosis" Ann. Surg. Oncol., 18, pp. 3261-3270 (2011).

Schulz et al., "A validated quantitative assay to detect occult micrometastases by reverse transcriptase-polymerase chain reaction of guanylyl cyclase C in patients with colorectal cancer", Clin Cancer Res. 12, pp. 4545-4552 (2006).

Search Report from corresponding Kenya Application No. KE/P/2012/001534 dated Jun. 25, 2014.

Singh et al., "Isolation and expression of a guanylate cyclase-coupled heat stable enterotoxin receptor cDNA from a human colonic cell line." Biochem Biophys Res Commun. 179(3):1455-1463 (1991).

Snook et al., "Guanylyl Cyclase C—Induced Immunotherapeutic Responses Opposing Tumor Metastases Without Autoimmunity" J. Natl. Cancer Inst., vol. 100, pp. 950-961 (2008).

Urbanski et al., "Interalization of *E. coli* ST mediated by guanylyl cyclase C in T84 human colon carcinoma cells", Biochimica eta Biophysica Acta., 1245, pp. 29-36 (1995).

Vaandrager et al., "Guanylyl cyclase C is an N-linked glycoprotein receptor that accounts for multiple heat-stable enterotoxin-binding proteins in the intestine." J Biol Chem. 268(3):2174-2179 (1993).

Vijayachandra et al., "Biochemical characterization of the intracellular domain of the human guanylyl cyclase C receptor provides

(56) References Cited

OTHER PUBLICATIONS evidence for a catalytically active homotrimer." Biochemistry 39:16075-16083 (2000).

Wiegand et al., "Human guanylin: cDNA isolation, structure, and activity." FEBS Lett. 311:150-154 (1992).

Wolfe et al., :In vivo imaging of human colon cancer xenografts in immunodeficient mice using a guanylyl cyclase C-specific ligand J Nucl. Med. 43, pp. 392-399 (2002).

Written Opinion from corresponding International Application No. PCT/US10/53686 dated Mar. 10, 2011.

* cited by examiner

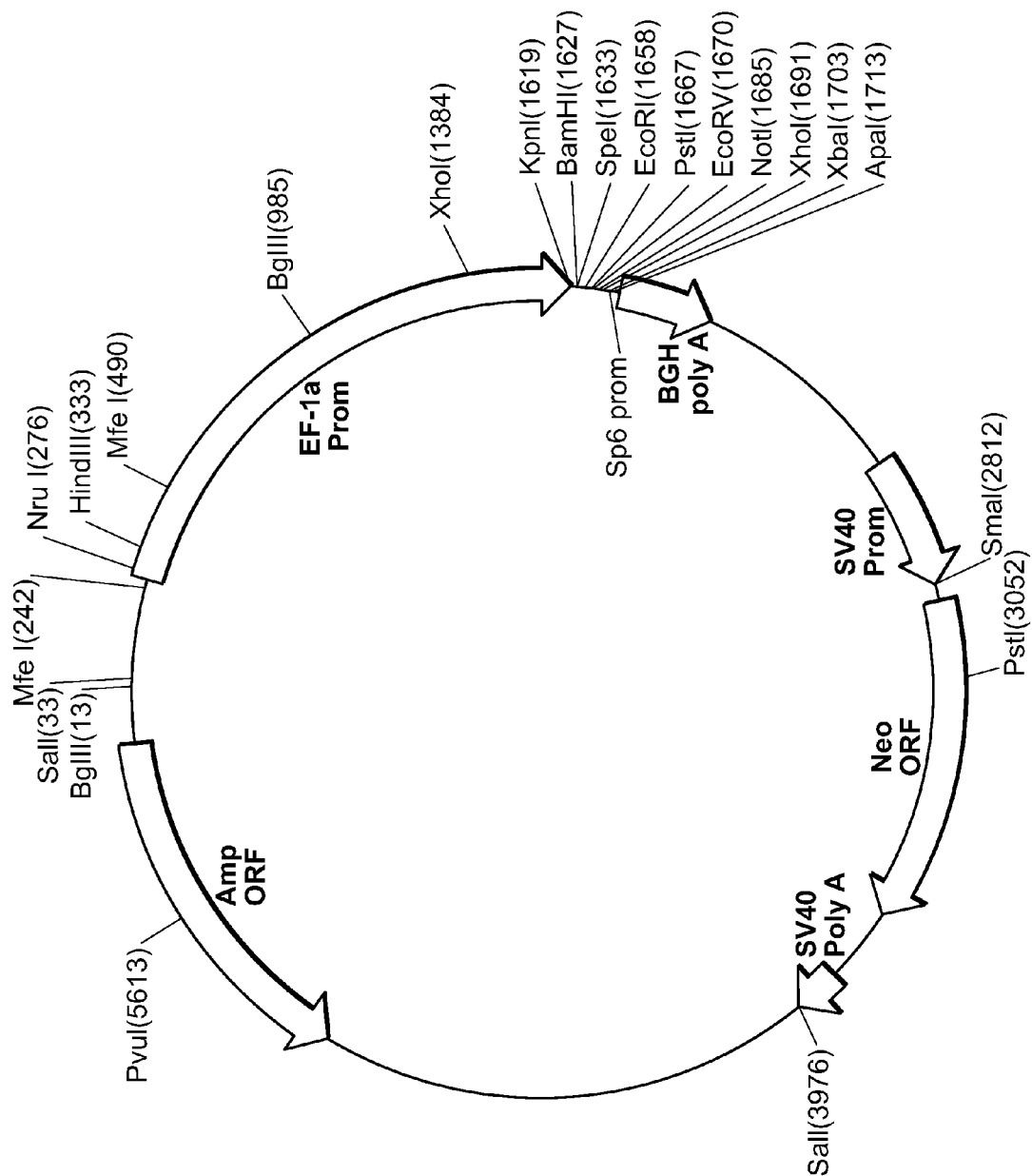

ANTI-GCC ANTIBODY MOLECULES AND METHODS FOR USE OF SAME

RELATED APPLICATIONS

The present application is a divisional of U.S. application Ser. No. 13/872,080, filed Apr. 27, 2013, now allowed, which claims the benefit of U.S. Provisional Application Ser. No. 61/639,376, filed Apr. 27, 2012. The entire content of U.S. Provisional Application Ser. No. 61/639,376 is incorporated herein by this reference.

BACKGROUND OF THE INVENTION

Guanylyl cyclase C ("GCC") is a transmembrane cell surface receptor that functions in the maintenance of intestinal fluid, electrolyte homeostasis and cell proliferation, see, e.g., Carrithers et al., Proc. Natl. Acad. Sci. USA 100:3018-3020 (2003). GCC is expressed at the mucosal cells lining the small intestine, large intestine and rectum (Carrithers et al., Dis Colon Rectum 39: 171-181 (1996)). GCC expression is maintained upon neoplastic transformation of intestinal epithelial cells, with expression in all primary and metastatic colorectal tumors (Carrithers et al., Dis Colon Rectum 39: 171-181 (1996); Buc et al. Eur J Cancer 41: 1618-1627 (2005); Carrithers et al., Gastroenterology 107: 1653-1661 (1994)).

The inventors have discovered novel anti-GCVC monoclonal antibodies. Accordingly, in one aspect, the invention features an anti-GCC antibody molecule, as disclosed herein. The anti-GCC antibody molecules are useful as naked antibody molecules and as components of immunoconjugates. Accordingly, in another aspect, the invention features immunoconjugates comprising an anti-GCC antibody molecule and a therapeutic agent or label. The invention also features methods of using the anti-GCC antibody molecules and immunoconjugates described herein for detection of GCC and of cells or tissues that express GCC; for diagnosis, prognosis, imaging, or staging of a GCC-mediated disease; for modulating an activity or function of a GCC protein; and for treatment of a GCC-mediated disease, as described herein. In another aspect, the invention also features isolated and/or recombinant nucleic acids encoding anti-GCC antibody molecule amino acid sequences, as well as vectors and host cells comprising such nucleic acids, and methods for producing anti-GCC antibody molecules.

All publications, patent applications, patents and other references mentioned herein are incorporated by references in their entirety.

Other features, objects, and advantages of the invention(s) disclosed herein will be apparent from the description and drawings, and from the claims.

BRIEF DESCRIPTION OF THE DRAWINGS

FIG. 1 is a circular map of a protein expression vector used to generate a human GCC (hGCC) extracellular domain (ECD) mouse Fc (mFc) fusion protein (hGCC-ECD-mFc) of the invention.

DETAILED DESCRIPTION

Guanylyl cyclase C (GCC) (also known as STAR, ST Receptor, GUC2C, and GUCY2C) is a transmembrane cell surface receptor that functions in the maintenance of intestinal fluid, electrolyte homeostasis and cell proliferation (Carrithers et al., *Proc Natl Acad Sci* USA 100: 3018-3020 (2003); Mann et al., *Biochem Biophys Res Commun* 239: 463-466 (1997); Pitari et al., *Proc Natl Acad Sci* USA 100: 2695-2699 (2003)); GenBank Accession No. NM_004963, each of which is incorporated herein by reference in its entirety). This function is mediated through binding of guanylin (Wiegand et al. FEBS Lett. 311:150-154 (1992)). GCC also is a receptor for heat-stable enterotoxin (ST, e.g., having an amino acid sequence of NTFYCCELCCNPACAGCY, SEQ ID NO: 1) which is a peptide produced by *E. coli*, as well as other infectious organisms (Rao, M. C. *Ciba Found. Symp.* 112:74-93 (1985); Knoop F. C. and Owens, M. *J. Pharmacol. Toxicol. Methods* 28:67-72 (1992)). Binding of ST to GCC activates a signal cascade that results in enteric disease, e.g., diarrhea.

```
                    Nucleotide sequence for human GCC
               (GenBank Accession No. NM_004963; SEQ ID NO: 2):

1 gaccagagag aagcgtgggg aagagtgggc tgagggactc cactagaggc tgtccatctg 61 gattccctgc ctccctagga gcccaacaga gcaaagcaag tgggcacaag gagtatggtt 121 ctaacgtgat tggggtcatg aagacgttgc tgttggactt ggctttgtgg tcactgctct 181 tccagcccgg gtggctgtcc tttagttccc aggtgagtca gaactgccac aatggcagct 241 atgaaatcag cgtcctgatg atgggcaact cagcctttgc agagccctg aaaaacttgg 301 aagatgcggt gaatgagggg ctggaaatag tgagaggacg tctgcaaaat gctggcctaa 361 atgtgactgt gaacgctact ttcatgtatt cggatggtct gattcataac tcaggcgact 421 gccggagtag cacctgtgaa ggcctcgacc tactcaggaa aatttcaaat gcacaacgga 481 tgggctgtgt cctcataggg ccctcatgta catactccac cttccagatg taccttgaca 541 cagaattgag ctaccccatg atctcagctg gaagttttgg attgtcatgt gactataaag 601 aaaccttaac caggctgatg tctccagcta gaaagttgat gtacttcttg gttaactttt 661 ggaaaaccaa cgatctgccc ttcaaaactt attcctggag cacttcgtat gtttacaaga 721 atggtacaga aactgaggac tgtttctggt accttaatgc tctggaggct agcgtttcct 781 atttctccca cgaactcggc tttaaggtgg tgttaagaca agataaggag tttcaggata
```

-continued

| Nucleotide sequence for human GCC (GenBank Accession No. NM_004963; SEQ ID NO: 2): |
|---|
| 841 tcttaatgga ccacaacagg aaaagcaatg tgattattat gtgtggtggt ccagagttcc |
| 901 tctacaagct gaagggtgac cgagcagtgg ctgaagacat tgtcattatt ctagtggatc |
| 961 ttttcaatga ccagtacttt gaggacaatg tcacagcccc tgactatatg aaaaatgtcc |
| 1021 ttgttctgac gctgtctcct gggaattccc ttctaaatag ctctttctcc aggaatctat |
| 1081 caccaacaaa acgagacttt gctcttgcct atttgaatgg aatcctgctc tttggacata |
| 1141 tgctgaagat atttcttgaa aatggagaaa atattaccac ccccaaattt gctcatgctt |
| 1201 tcaggaatct cacttttgaa gggtatgacg tccagtgac cttggatgac tgggggatg |
| 1261 ttgacagtac catggtgctt ctgtatacct ctgtggacac caagaaatac aaggttcttt |
| 1321 tgacctatga tacccacgta aataagacct atcctgtgga tatgagcccc acattcactt |
| 1381 ggaagaactc taaacttcct aatgatatta caggccgggg ccctcagatc ctgatgattg |
| 1441 cagtcttcac cctcactgga gctgtggtgc tgctcctgct cgtcgctctc ctgatgctca |
| 1501 gaaaatatag aaaagattat gaacttcgtc agaaaaaatg gtcccacatt cctcctgaaa |
| 1561 atatctttcc tctggagacc aatgagacca atcatgttag cctcaagatc gatgatgaca |
| 1621 aaagacgaga tacaatccag agactacgac agtgcaaata cgacaaaaag cgagtgattc |
| 1681 tcaaagatct caagcacaat gatggtaatt tcactgaaaa acagaagata gaattgaaca |
| 1741 agttgcttca gattgactat tacaacctga ccaagttcta cggcacagtg aaacttgata |
| 1801 ccatgatctt cggggtgata gaatactgtg agagaggatc cctccgggaa gttttaaatg |
| 1861 acacaatttc ctaccctgat ggcacattca tggattggga gtttaagatc tctgtcttgt |
| 1921 atgacattgc taagggaatg tcatatctgc actccagtaa gacagaagtc catggtcgtc |
| 1981 tgaaatctac caactgcgta gtggacagta aatggtggt gaagatcact gattttggct |
| 2041 gcaattccat tttacctcca aaaaaggacc tgtggacagc tccagagcac ctccgccaag |
| 2101 ccaacatctc tcagaaagga gatgtgtaca gctatgggat catcgcacag agatcatcc |
| 2161 tgcggaaaga aaccttctac actttgagct gtcgggaccg gaatgagaag attttcagag |
| 2221 tggaaaattc caatggaatg aaaccettcc gcccagattt attcttggaa acagcagagg |
| 2281 aaaaagagct agaagtgtac ctacttgtaa aaaactgttg ggaggaagat ccagaaaaga |
| 2341 gaccagattt caaaaaaatt gagactacac ttgccaagat atttggactt tttcatgacc |
| 2401 aaaaaaatga aagctatatg gataccttga tccgacgtct acagctatat tctcgaaacc |
| 2461 tggaacatct ggtagaggaa aggacacagc tgtacaaggc agagagggac agggctgaca |
| 2521 gacttaactt tatgttgctt ccaaggctag tggtaaagtc tctgaaggag aaaggctttg |
| 2581 tggagccgga actatatgag gaagttacaa tctacttcag tgacattgta ggtttcacta |
| 2641 ctatctgcaa atacagcacc cccatggaag tggtggacat gcttaatgac atctataaga |
| 2701 gttttgacca cattgttgat catcatgatg tctacaaggt ggaaaccatc ggtgatgcgt |
| 2761 acatggtggc tagtggtttg cctaagagaa atggcaatcg gcatgcaata gacattgcca |
| 2821 agatggcctt ggaaatcctc agcttcatgg gaccttttga gctggagcat ttcctggcc |
| 2881 tcccaatatg gattcgcatt ggagttcact ctggtccctg tgctgctgga gttgtgggaa |
| 2941 tcaagatgcc tcgttattgt ctatttggag atacggtcaa cacagcctct aggatggaat |
| 3001 ccactggcct ccctttgaga attcacgtga gtggctccac catagccatc tgaagagaa |
| 3061 ctgagtgcca gttcctttat gaagtgagag gagaaacata cttaaaggga agaggaaatg |

-continued

Nucleotide sequence for human GCC
(GenBank Accession No. NM_004963; SEQ ID NO: 2):

```
3121 agactaccta ctggctgact gggatgaagg accagaaatt caacctgcca acccctccta
3181 ctgtggagaa tcaacagcgt ttgcaagcag aattttcaga catgattgcc aactctttac
3241 agaaaagaca ggcagcaggg ataagaagcc aaaaacccag acgggtagcc agctataaaa
3301 aaggcactct ggaatacttg cagctgaata ccacagacaa ggagagcacc tattttaaa
```

Amino acid sequence for human GCC
(GenPept Accession No. NP_004954; SEQ ID NO: 3):

```
   1 mktllldlal wsllfqpgwl sfssqvsqnc hngsyeisvl mmgnsafaep lknledavne
  61 gleivrgrlq naglnvtvna tfmysdglih nsgdcrsstc egldllrkis naqrmgcvli
 121 gpsctystfq myldtelsyp misagsfgls cdyketltrl msparklmyf lvnfwktndl
 181 pfktyswsts yvykngtete dcfwylnale asvsyfshel gfkvvlrqdk efqdilmdhn
 241 rksnviimcg gpeflyklkg dravaedivi ilvdlfndqy fednvtapdy mknvlvltls
 301 pgnsllnssf srnlsptkrd falaylngil lfghmlkifl engenittpk fahafrnltf
 361 egydgpvtld dwgdvdstmv llytsvdtkk ykvlltydth vnktypvdms ptftwknskl
 421 pnditgrgpq ilmiavftlt gavvllllva llmlrkyrkd yelrqkkwsh ippenifple
 481 tnetnhvslk idddkrrdti qrlrqckydk krvilkdlkh ndgnftekqk ielnkllqid
 541 yynltkfygt vkldtmifgv ieycergslr evlndtisyp dgtfmdwefk isvlydiakg
 601 msylhsskte vhgrlkstnc vvdsrmvvki tdfgcnsilp pkkdlwtape hlrqanisqk
 661 gdvysygiia geiilrketf ytlscrdrne kifrvensng mkpfrpdlfl etaeekelev
 721 yllvkncwee dpekrpdfkk iettlakifg lfhdqknesy mdtlirrlql ysrnlehlve
 781 ertqlykaer dradrlnfml lprlvvkslk ekgfvepely eevtiyfsdi vgfttickys
 841 tpmevvdmln diyksfdhiv dhhdvykvet igdaymvasg lpkrngnrha idiakmalei
 901 lsfmgtfele hlpglpiwir igvhsgpcaa gvvgikmpry clfgdtvnta srmestglpl
 961 rihvsgstia ilkrtecqfl yevrgetylk grgnettywl tgmkdqkfnl ptpptvenqq
1021 rlqaefsdmi anslqkrqaa girsqkprrv asykkgtley lqlnttdkes tyf
```

The GCC protein has some generally accepted domains each of which contributes a separable function to the GCC molecule. The portions of GCC include a signal sequence (for directing the protein to the cell surface) from amino acid residue 1 to about residue 23, or residue 1 to about residue 21 of SEQ ID NO: 3 (excised for maturation to yield functional mature protein from about amino acid residues 22 or 24 to 1073 of SEQ ID NO: 3), an extracellular domain for ligand, e.g., guanylin or ST, binding from about amino acid residue 24 to about residue 420, or about residue 54 to about residue 384 of SEQ ID NO: 3, a transmembrane domain from about amino acid residue 431 to about residue 454, or about residue 436 to about residue 452 of SEQ ID NO: 3, a kinase homology domain, predicted to have tyrosine kinase activity from about amino acid residue 489 to about residue 749, or about residue 508 to about residue 745 of SEQ ID NO: 3 and a guanylyl cyclase catalytic domain from about residue 750 to about residue 1007, or about residue 816 to about residue 1002 of SEQ ID NO: 3.

In normal human tissues, GCC is expressed at the mucosal cells, e.g., at the apical brush border membranes, lining the small intestine, large intestine and rectum (Carrithers et al., *Dis Colon Rectum* 39: 171-181 (1996)). GCC expression is maintained upon neoplastic transformation of intestinal epithelial cells, with expression in all primary and metastatic colorectal tumors (Carrithers et al., *Dis Colon Rectum* 39: 171-181 (1996); Buc et al. Eur J Cancer 41: 1618-1627 (2005); Carrithers et al., *Gastroenterology* 107: 1653-1661 (1994)). Neoplastic cells from the stomach, esophagus and the gastroesophageal junction also express GCC (see, e.g., U.S. Pat. No. 6,767,704; Debruyne et al. Gastroenterology 130:1191-1206 (2006)). The tissue-specific expression and association with cancer, e.g., of gastrointestinal origin, (e.g., colon cancer, stomach (gastric) cancer, or esophageal cancer), can be exploited for the use of GCC as a diagnostic marker for this disease (Carrithers et al., *Dis Colon Rectum* 39: 171-181 (1996); Buc et al. *Eur J Cancer* 41: 1618-1627 (2005)).

As a cell surface protein, GCC can also serve as a diagnostic or therapeutic target for receptor binding proteins such as antibodies or ligands. In normal intestinal tissue, GCC is expressed on the apical side of epithelial cell tight junctions that form an impermeable barrier between the luminal environment and vascular compartment (Almenoff et al., Mol Microbiol 8: 865-873); Guarino et al., Dig Dis Sci 32: 1017-1026 (1987)). As such, systemic intravenous administration of a GCC-binding protein therapeutic will have minimal effect on intestinal GCC receptors, while having access to neoplastic cells of the gastrointestinal system, including invasive or metastatic colon cancer cells, extraintestinal or metastatic colon tumors, esophageal tumors or stomach tumors, adenocarcinoma at the gastroesophageal junction. Additionally, GCC internalizes through receptor mediated endocytosis upon ligand binding (Buc et al. *Eur J Cancer* 41: 1618-1627 (2005); Urbanski et al., *Biochem Biophys Acta* 1245: 29-36 (1995)).

Polyclonal antibodies raised against the extracellular domain of GCC (Nandi et al. *Protein Expr. Purif.* 8:151-159 (1996)) were able to inhibit the ST peptide binding to human and rat GCC and inhibit ST-mediated cGMP production by human GCC.

GCC has been characterized as a protein involved in cancers, including colon cancers. See also, Carrithers et al., *Dis Colon Rectum* 39: 171-181 (1996); Buc et al. Eur J Cancer 41: 1618-1627 (2005); Carrithers et al., *Gastroenterology* 107: 1653-1661 (1994); Urbanski et al., *Biochem Biophys Acta* 1245: 29-36 (1995). Antibody molecules directed to GCC can thus be used alone in unconjugated form to inhibit the GCC-expressing cancerous cells. Additionally, antibody molecules directed to GCC can be used in naked or labeled form, to detect GCC-expressing cancerous cells. Anti-GCC antibody molecules of the invention can bind human GCC. In some embodiments, an anti-GCC antibody molecule of the invention can inhibit the binding of a ligand, e.g., guanylin or heat-stable enterotoxin to GCC. In other embodiments, an anti-GCC antibody molecule of the invention does not inhibit the binding of a ligand, e.g., guanylin or heat-stable enterotoxin to GCC.

Monoclonal antibodies specific for GCC include GCC:B10 (Nandi et al., *J. Cell. Biochem.* 66:500-511 (1997)), GCC:4D7 (Vijayachandra et al. *Biochemistry* 39:16075-16083 (2000)) and GCC:C8 (Bakre et al. *Eur. J. Biochem.* 267:179-187 (2000)). GCC:B10 has a kappa light chain and an IgG2a isotype and cross-reacts to rat, pig and monkey GCC. GCC:B10 binds to the first 63 amino acids of the intracellular domain of GCC, specifically to residues 470-480 of SEQ ID NO: 3 (Nandi et al. *Protein Sci.* 7:2175-2183 (1998)). GCC:4D7 binds to the kinase homology domain, within residues 491-568 of GCC (Bhandari et al. *Biochemistry* 40:9196-9206 (2001)). GCC:C8 binds to the protein kinase-like domain in the cytoplasmic portion of GCC.

DEFINITIONS

Unless otherwise defined herein, scientific and technical terms used in connection with the present invention have the meanings that are commonly understood by those of ordinary skill in the art. Generally, nomenclature utilized in connection with, and techniques of, cell and tissue culture, molecular biology, and protein and oligo- or polynucleotide chemistry and hybridization described herein are those known in the art. GenBank or GenPept accession numbers and useful nucleic acid and peptide sequences can be found at the website maintained by the National Center for Biotechnological Information, Bethesda Md. Standard techniques are used for recombinant DNA, oligonucleotide synthesis, and tissue culture and transformation and transfection (e.g., electroporation, lipofection). Enzymatic reactions and purification techniques are performed according to manufacturer's specifications or as commonly accomplished in the art or as described herein. The foregoing techniques and procedures are generally performed according to methods known in the art, e.g., as described in various general and more specific references that are cited and discussed throughout the present specification. See e.g., Sambrook et al. *Molecular Cloning: A Laboratory Manual* (3rd ed., Cold Spring Harbor Laboratory Press, Cold Spring Harbor, N.Y. (2000)) or see generally, Harlow, E. and Lane, D. (1988) *Antibodies: A Laboratory Manual*, Cold Spring Harbor Laboratory Press, Cold Spring Harbor, N.Y. The nomenclatures utilized in connection with, and the laboratory procedures and techniques of, described herein are known in the art. Furthermore, unless otherwise required by context, singular terms shall include pluralities and plural terms shall include the singular.

As used herein, the term "antibody molecule" refers to an antibody, antibody peptide(s) or immunoglobulin, or an antigen binding fragment of any of the foregoing, e.g., of an antibody. Antibody molecules include single chain antibody molecules, e.g., scFv, see. e.g., Bird et al. (1988) *Science* 242:423-426; and Huston et al. (1988) *Proc. Natl. Acad. Sci. USA* 85:5879-5883), and single domain antibody molecules, see, e.g., WO9404678. Although not within the term "antibody molecules," the invention also includes "antibody analog(s)," other non-antibody molecule protein-based scaffolds, e.g., fusion proteins and/or immunoconjugates that use CDRs to provide specific antigen binding.

An "anti-GCC antibody molecule" refers to an antibody molecule (i.e., an antibody, antigen-binding fragment of an antibody or antibody analog) which interacts with or recognizes, e.g., binds (e.g., binds specifically) to GCC, e.g., human GCC. Exemplary anti-GCC antibody molecules are such as those summarized in Tables 1 and 2.

As used herein, the term "antibody," "antibody peptide(s)" or "immunoglobulin" refers to single chain, two-chain, and multi-chain proteins and glycoproteins. The term antibody includes polyclonal, monoclonal, chimeric, CDR-grafted and human or humanized antibodies, all of which are discussed in more detail elsewhere herein. Also included within the term are camelid antibodies, see, e.g., US2005/0037421, and nanobodies, e.g., IgNARs (shark antibodies), see, e.g., WO03/014161. The term "anti body" also includes synthetic and genetically engineered variants.

As used herein, the term "antibody fragment" or "antigen binding fragment" of an antibody refers, e.g., to Fab, Fab', F(ab')$_2$, and Fv fragments, single chain antibodies, functional heavy chain antibodies (nanobodies), as well as any portion of an antibody having specificity toward at least one desired epitope, that competes with the intact antibody for specific binding (e.g., a fragment having sufficient CDR sequences and having sufficient framework sequences so as to bind specifically to an epitope). E.g., an antigen binding fragment can compete for binding to an epitope which binds the antibody from which the fragment was derived. Derived, as used in this and similar contexts, does not imply any particular method or process of derivation, but can refer merely to sequence similarity. Antigen binding fragments can be produced by recombinant techniques, or by enzymatic or chemical cleavage of an intact antibody. The term, antigen binding fragment, when used with a single chain, e.g., a heavy chain, of an antibody having a light and heavy chain means that the fragment of the chain is sufficient such that when paired with a complete variable region of the other chain, e.g., the light chain, it will allow binding of at least 25, 50, 75, 85 or 90% of that seen with the whole heavy and light variable region.

The term, "antigen binding constellation of CDRs" or "a number of CDRs sufficient to allow binding" (and similar language), as used herein, refers to sufficient CDRs of a chain, e.g., the heavy chain, such that when placed in a framework and paired with a complete variable region of the other chain, or with a portion of the other chain's variable region of similar length and having the same number of CDRs, e.g., the light chain, will allow binding, e.g., of at least 25, 50, 75, 85 or 90% of that seen with the whole heavy and light variable region.

As used herein, the term "humanized antibody" refers to an antibody that is derived from a non-human antibody e.g., rabbit, rodent (e.g., murine), sheep or goat, that retains or substantially retains the antigen-binding properties of the parent antibody but is less immunogenic in humans. Humanized as used herein is intended to include deimmunized antibodies. Typically, humanized antibodies include non-human CDRs and human or human derived framework and constant regions.

The term "modified" antibody, as used herein, refers to antibodies that are prepared, expressed, created or isolated by recombinant means, such as antibodies expressed using a recombinant expression vector transfected into a host cell, antibodies isolated from a recombinant, combinatorial antibody library, antibodies isolated from a non-human animal (e.g., a rabbit, mouse, rat, sheep or goat) that is transgenic for human immunoglobulin genes or antibodies prepared, expressed, created or isolated by any other means that involves splicing of human immunoglobulin gene sequences to other DNA sequences. Such modified antibodies include humanized, CDR grafted (e.g., an antibody having CDRs from a first antibody and a framework region from a different source, e.g., a second antibody or a consensus framework), chimeric, in vitro generated (e.g., by phage display) antibodies, and may optionally include variable or constant regions derived from human germline immunoglobulin sequences or human immunoglobulin genes or antibodies which have been prepared, expressed, created or isolated by any means that involves splicing of human immunoglobulin gene sequences to alternative immunoglobulin sequences. In embodiments a modified antibody molecule includes an antibody molecule having a sequence change from a reference antibody.

The term "monospecific antibody" refers to an antibody or antibody preparation that displays a single binding specificity and affinity for a particular epitope. This term includes a "monoclonal antibody" or "monoclonal antibody composition."

The term "bispecific antibody" or "bifunctional antibody" refers to an antibody that displays dual binding specificity for two epitopes, where each binding site differs and recognizes a different epitope.

The terms "non-conjugated antibody" and "naked antibody" are used interchangeably to refer to an antibody molecule that is not conjugated to a non-antibody moiety, e.g., a label.

The terms "immunoconjugate" and "antibody conjugate", are used interchangeably and refer to an antibody that is conjugated to a non-antibody moiety, e.g., an agent or a label.

The term "agent" is used herein to denote a chemical compound, a mixture of chemical compounds, a biological macromolecule, or an extract made from biological materials. The term "therapeutic agent" refers to an agent that has biological activity.

The term "anti-cancer agent" or "chemotherapeutic agent" is used herein to refer to agents that have the functional property of inhibiting a development or progression of a neoplasm in a human, particularly a malignant (cancerous) lesion, such as a carcinoma, sarcoma, lymphoma, or leukemia Inhibition of metastasis or angiogenesis is frequently a property of anti-cancer or chemotherapeutic agents. A chemotherapeutic agent may be a cytotoxic or cytostatic agent. The term "cytostatic agent" refers to an agent which inhibits or suppresses cell growth and/or multiplication of cells.

"Cytotoxic agents" refer to compounds which cause cell death primarily by interfering directly with the cell's functioning, including, but not limited to, alkylating agents, tumor necrosis factor inhibitors, intercalators, microtubule inhibitors, kinase inhibitors, proteasome inhibitors and topoisomerase inhibitors. A "toxic payload" as used herein refers to a sufficient amount of cytotoxic agent which, when delivered to a cell results in cell death. Delivery of a toxic payload may be accomplished by administration of a sufficient amount of immunoconjugate comprising an antibody or antigen binding fragment of the invention and a cytotoxic agent. Delivery of a toxic payload may also be accomplished by administration of a sufficient amount of an immunoconjugate comprising a cytotoxic agent, wherein the immunoconjugate comprises a secondary antibody or antigen binding fragment thereof which recognizes and binds an antibody or antigen binding fragment of the invention.

As used herein the phrase, a sequence "derived from" or "specific for a designated sequence" refers to a sequence that comprises a contiguous sequence of approximately at least 6 nucleotides or at least 2 amino acids, at least about 9 nucleotides or at least 3 amino acids, at least about 10-12 nucleotides or 4 amino acids, or at least about 15-21 nucleotides or 5-7 amino acids corresponding, i.e., identical or complementary to, e.g., a contiguous region of the designated sequence. In certain embodiments, the sequence comprises all of a designated nucleotide or amino acid sequence. The sequence may be complementary (in the case of a polynucleotide sequence) or identical to a sequence region that is unique to a particular sequence as determined by techniques known in the art. Regions from which sequences may be derived, include but are not limited to, regions encoding specific epitopes, regions encoding CDRs, regions encoding framework sequences, regions encoding constant domain regions, regions encoding variable domain regions, as well as non-translated and/or non-transcribed regions. The derived sequence will not necessarily be derived physically from the sequence of interest under study, but may be generated in any manner, including, but not limited to, chemical synthesis, replication, reverse transcription or transcription, that is based on the information provided by the sequence of bases in the region(s) from which the polynucleotide is derived. As such, it may represent either a sense or an antisense orientation of the original polynucleotide. In addition, combinations of regions corresponding to that of the designated sequence may be modified or combined in ways known in the art to be consistent with the intended use. For example, a sequence may comprise two or more contiguous sequences which each comprise part of a designated sequence, and are interrupted with a region which is not identical to the designated sequence but is intended to represent a sequence derived from the designated sequence. With regard to antibody molecules, "derived therefrom" includes an antibody molecule which is functionally or structurally related to a comparison antibody, e.g., "derived therefrom" includes an antibody molecule having similar or substantially the same sequence or structure, e.g., having the same or similar CDRs, framework or variable regions. "Derived therefrom" for an antibody also includes residues, e.g., one or more, e.g., 2, 3, 4, 5, 6 or more residues, which may or may not be contiguous, but are defined or identified according to a numbering scheme or homology to general antibody structure or three-dimensional proximity, i.e., within a CDR or a framework region, of a comparison sequence. The term "derived therefrom" is not limited to physically derived therefrom but includes generation by any manner, e.g., by use of sequence information from a comparison antibody to design another antibody.

As used herein, the phrase "encoded by" refers to a nucleic acid sequence that codes for a polypeptide sequence, wherein the polypeptide sequence or a portion thereof contains an amino acid sequence of at least 3 to 5 amino acids, at least 8 to 10 amino acids, or at least 15 to 20 amino acids from a polypeptide encoded by the nucleic acid sequence.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 30%, 40%, or 50%, at least 60%, or at least 70%, 80%, 90%, 95%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. The percent homology between two amino acid sequences can be determined using any method known in the art. For example, the Needleman and Wunsch, J. Mol. Biol. 48:444-453 (1970), algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. The percent homology between two nucleotide sequences can also be determined using the GAP program in the GCG software package (Accelerys, Inc. San Diego, Calif.), using an NWSgapdna.CMP matrix and a gap weight of 40, 50, 60, 70, or 80 and a length weight of 1, 2, 3, 4, 5, or 6. An exemplary set of parameters for determination of homology are a Blossum 62 scoring matrix with a gap penalty of 12, a gap extend penalty of 4, and a frameshift gap penalty of 5.

As used herein, the term "hybridizes under stringent conditions" describes conditions for hybridization and washing. Guidance for performing hybridization reactions can be found in Current Protocols in Molecular Biology, John Wiley & Sons, N.Y. (1989), 6.3.1-6.3.6. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C. Very high stringency conditions (4) are often the preferred conditions and the ones that should be used unless otherwise specified.

It is understood that the antibody molecules of the invention may have additional conservative or non-essential amino acid substitutions, which do not have a substantial effect on the polypeptide functions. Whether or not a particular substitution will be tolerated, i.e., will not adversely affect desired biological properties, such as binding activity, can be determined as described in Bowie, J U et al. *Science* 247:1306-1310 (1990) or Padlan et al. *FASEB J.* 9:133-139 (1995). A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), non-polar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of the binding agent, e.g., the antibody, without abolishing or, without substantially altering a biological activity, whereas an "essential" amino acid residue results in such a change. In an antibody, an essential amino acid residue can be a specificity determining residue (SDR).

As used herein, the term "isolated" refers to material that is removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such polynucleotide or polypeptide could be part of a vector and/or such polynucleotide or polypeptide could be part of a composition, e.g., a mixture, solution or suspension or comprising an isolated cell or a cultured cell which comprises the polynucleotide or polypeptide, and still be isolated in that the vector or composition is not part of its natural environment.

As used herein, the term "replicon" refers to any genetic element, such as a plasmid, a chromosome or a virus, that behaves as an autonomous unit of polynucleotide replication within a cell.

As used herein, the term "operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequence.

As used herein, the term "vector" refers to a replicon in which another polynucleotide segment is attached, such as to bring about the replication and/or expression of the attached segment.

As used herein, the term "control sequence" refers to a polynucleotide sequence that is necessary to effect the expression of a coding sequence to which it is ligated. The nature of such control sequences differs depending upon the host organism. In prokaryotes, such control sequences generally include a promoter, a ribosomal binding site and terminators and, in some instances, enhancers. The term "control sequence" thus is intended to include at a minimum all components whose presence is necessary for expression, and also may include additional components whose presence is advantageous, for example, leader sequences.

As used herein, the term "purified product" refers to a preparation of the product which has been isolated from the cellular constituents with which the product is normally associated and/or from other types of cells that may be present in the sample of interest.

As used herein, the term "epitope" refers to a protein determinate capable of binding specifically to an antibody. Epitopic determinants usually consist of chemically active surface groupings of molecules such as amino acids or sugar side chains and usually have specific three dimensional structural characteristics, as well as specific charge characteristics. Some epitopes are linear epitopes while others are conformational epitopes. A linear epitope is an epitope wherein a contiguous amino acid primary sequence comprises the epitope recognized. A linear epitope typically includes at least 3, and more usually, at least 5, for example, about 8 to about 10 contiguous amino acids. A conformational epitope can result from at least two situations, such as: a) a linear sequence which is only exposed to antibody binding in certain protein conformations, e.g., dependent on ligand binding, or dependent on modification (e.g., phosphorylation) by signaling molecules; or b) a combination of structural features from more than one part of the protein, or in multisubunit proteins, from more than one subunit, wherein the features are in sufficiently close proximity in 3-dimensional space to participate in binding.

As used herein, "isotype" refers to the antibody class (e.g., IgM, IgA, IgE or IgG) that is encoded by heavy chain constant region genes.

As used herein, the terms "detectable agent," "label" or "labeled" are used to refer to incorporation of a detectable marker on a polypeptide or glycoprotein. Various methods of labeling polypeptides and glycoproteins are known in the art and may be used. Examples of labels for polypeptides include, but are not limited to, the following: radioisotopes or radionuclides (e.g., indium ($^{111}$In), iodine ($^{131}$I or $^{125}$I), yttrium ($^{90}$Y), lutetium ($^{177}$Lu), actinium ($^{225}$Ac), bismuth ($^{212}$Bi or $^{213}$Bi), sulfur ($^{35}$S), carbon ($^{14}$C), tritium ($^{3}$H), rhodium ($^{188}$Rh), technetium ($^{99}$ mTc), praseodymium, or phosphorous ($^{32}$P) or a positron-emitting radionuclide, e.g., carbon-11 ($^{11}$C), potassium-40 ($^{40}$K), nitrogen-13 ($^{13}$N), oxygen-15 ($^{15}$O)$_9$, fluorine-18 ($^{18}$F), gallium-68 ($^{68}$Ga), and iodine-121 ($^{121}$I)), fluorescent labels (e.g., FITC, rhodamine, lanthanide phosphors), enzymatic labels (e.g., horseradish peroxidase, beta-galactosidase, luciferase, alkaline phosphatase), chemiluminescent, biotinyl groups (which can be detected by a marked avidin, e.g., a molecule containing a streptavidin moiety and a fluorescent marker or an enzymatic activity that can be detected by optical or calorimetric methods), and predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "specific binding," "bind(s) specifically" or "binding specificity" means, for an anti-GCC antibody molecule, that the antibody molecule binds to GCC, e.g., human GCC protein, with greater affinity than it does to a non-GCC protein, e.g., BSA. Typically an anti-GCC molecule will have a $K_d$ for the non-GCC protein, e.g., BSA, which is greater than 2, greater than 10, greater than 100, greater than 1,000 times, greater than $10^4$, greater than $10^5$, or greater than $10^6$ times its $K_d$ for GCC, e.g., human GCC protein. In determination of $K_d$, the K $K_d$ for GCC and the non-GCC protein, e.g., BSA, should be done under the same conditions.

As used herein, the term "treat" or "treatment" is defined as the administration of an anti-GCC antibody molecule to a subject, e.g., a patient, or administration, e.g., by application, to an isolated tissue or cell from a subject which is returned to the subject. The anti-GCC antibody molecule can be administered alone or in combination with a second agent. The treatment can be to cure, heal, alleviate, relieve, alter, remedy, ameliorate, palliate, improve or affect the disorder, the symptoms of the disorder or the predisposition toward the disorder, e.g., a cancer. While not wishing to be bound by theory, treating is believed to cause the inhibition, ablation, or killing of a cell in vitro or in vivo, or otherwise reducing capacity of a cell, e.g., an aberrant cell, to mediate a disorder, e.g., a disorder as described herein (e.g., a cancer).

As used herein, the term "subject" is intended to include mammals, primates, humans and non-human animals. For example, a subject can be a patient (e.g., a human patient or a veterinary patient), having a cancer, e.g., of gastrointestinal origin (e.g., colon cancer), a symptom of a cancer, e.g., of gastrointestinal origin (e.g., colon cancer), in which at least some of the cells express GCC, or a predisposition toward a cancer, e.g., of gastrointestinal origin (e.g., colon cancer), in which at least some of the cells express GCC. The term "non-human animals" of the invention includes all non-human vertebrates, e.g., non-human mammals and non-mammals, such as non-human primates, sheep, dog, cow, chickens, amphibians, reptiles, mouse, rat, rabbit or goat etc., unless otherwise noted. In an embodiment, "subject" excludes one or more or all of a mouse, rat, rabbit, sheep or goat.

As used herein, an amount of an anti-GCC antibody molecule "effective" or "sufficient" to treat a disorder, or a "therapeutically effective amount" or "therapeutically sufficient amount" refers to an amount of the antibody molecule which is effective, upon single or multiple dose administration to a subject, in treating a cell, e.g., cancer cell (e.g., a GCC-expressing tumor cell), or in prolonging curing, alleviating, relieving or improving a subject with a disorder as described herein beyond that expected in the absence of such treatment. As used herein, "inhibiting the growth" of the tumor or cancer refers to slowing, interrupting, arresting or stopping its growth and/or metastases and does not necessarily indicate a total elimination of the tumor growth.

As used herein, "GCC," also known as "STAR", "GUC2C", "GUCY2C" or "ST receptor" protein refers to mammalian GCC, preferably human GCC protein. Human GCC refers to the protein shown in SEQ ID NO: 3 and naturally occurring allelic protein variants thereof. The allele in SEQ ID NO: 3 can be encoded by the nucleic acid sequence of GCC shown in SEQ ID NO: 2. Other variants are known in the art. See, e.g., accession number Ensp0000261170, Ensembl Database, European Bioinformatics Institute and Wellcome Trust Sanger Institute, which has a leucine at residue 281; SEQ ID NO: 14 of published US patent application number 20060035852; or GenBank accession number AAB 19934. Typically, a naturally occurring allelic variant has an amino acid sequence at least 95%, 97% or 99% identical to the GCC sequence of SEQ ID NO: 3. The transcript encodes a protein product of 1073 amino acids, and is described in GenBank accession no.: NM_004963. GCC protein is characterized as a transmembrane cell surface receptor protein, and is believed to play a critical role in the maintenance of intestinal fluid, electrolyte homeostasis and cell proliferation.

Antibodies

In certain aspects, the invention relates to anti-GCC antibody molecules with features such as those summarized in Tables 1 and 2. In other aspects, the invention relates to anti-GCC antibody molecules with features such as those summarized in Tables 3, 4, 5 and/or 6.

In an embodiment, the anti-GCC antibody molecule is a rabbit hybridoma antibody and is one of antibody MIL-44-148-2 or MIL-44-67-4. In an embodiment, the anti-GCC antibody molecule is derived from antibody MIL-44-148-2 or MIL-44-67-4. In an embodiment, the anti-GCC antibody molecule is produced by hybridoma MIL-44-148-2 or MIL-44-67-4.

In an embodiment an anti-GCC antibody molecule will have an affinity for GCC, e.g., as measured by direct binding or competition binding assays. In an embodiment the anti-GCC antibody molecule has a $K_d$ of less than $1\times10^{-6}$ M, less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In an embodiment the antibody molecule is an IgG, or antigen-binding fragment thereof, and has a $K_d$ of less than $1\times10^{-6}$ M, less than $1\times10^{-7}$ M, less than $1\times10^{-8}$ M, or less than $1\times10^{-9}$ M. In an embodiment, an anti-GCC antibody molecule, e.g., a MIL-44-148-2 antibody or antibody derived therefrom has a $K_d$ of about 80 to about 200 pM, preferably about 100 to about 150 pM or about 120 pM. In an embodiment, an anti-GCC antibody molecule, e.g., a MIL-44-148-2 antibody or antibody derived therefrom has a $k_a$ of about 0.9 to about $1.25\times10^5$ $M^{-1}$ $s^{-1}$, preferably about $1.1\times10^5$ $M^{-1}$ $s^{-1}$. In an embodiment the antibody molecule is an ScFv and has a $K_d$ of less than $1\times10^{-6}$ M, less than $1\times10^{-7}$ M, less than $1\times10^{-8}$ M, less than $1\times10^{-9}$ M, less than $1\times10^{-10}$ M, $1\times10^{-11}$ M, less than $1\times10^{-12}$ M, or less than $1\times10^{-13}$ M.

In embodiments, the antibody molecules are not immunoconjugates, i.e., are "naked" and in embodiments cause a cellular reaction upon binding to GCC. In related embodiments, the cellular reaction is performed by the GCC-expressing cell to which the antibody binds. Such a cellular reaction can be signal transduction mediated by GCC, e.g., if the antibody molecule is an agonist of GCC (see, e.g., US Patent Application publication no. US20040258687). In other embodiments, the cellular reaction is performed by a second cell, e.g., an immune effector cell (e.g., a natural killer cell) which recognizes the antibody molecule bound to GCC on the first cell. In some embodiments, surveillance molecules, e.g., complement molecules, contact the GCC-bound antibody molecule prior to the cellular reaction. The cellular reactions in these embodiments can cause death of the GCC-expressing cell.

In further embodiments, antibody molecules which are immunoconjugates can both cause a cellular reaction upon binding to GCC and internalize to deliver an agent to the GCC-expressing cell to which it binds.

In some embodiments, an anti-GCC antibody molecule of the invention can block ligand binding to GCC.

In an embodiment, the antibody molecule is not GCC:B10, GCC:4D7 or GCC:C8. In another embodiment, an anti-GCC antibody molecule does not bind an intracellular domain of GCC, about amino acid residue 455 to 1073 of SEQ ID NO: 3. For example, in this embodiment, an anti-GCC antibody molecule does not bind the kinase homology domain or the guanylyl cyclase domain of GCC.

The naturally occurring mammalian antibody structural unit is typified by a tetramer. Each tetramer is composed of two pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains can be classified as kappa and lambda light chains. Heavy chains can be classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)).

The variable regions of each light/heavy chain pair form the antibody binding site. In some embodiments, isotypes for the anti-GCC antibody molecules are IgG immunoglobulins, which can be classified into four subclasses, IgG1, IgG2, IgG3 and IgG4, having different gamma heavy chains. Most therapeutic antibodies are human, chimeric, or humanized antibodies of the IgG1 isotype. In a particular embodiment, the anti-GCC antibody molecule is a rabbit IgG antibody.

The variable regions of each heavy and light chain pair form the antigen binding site. Thus, an intact IgG antibody has two binding sites which are the same. However, bifunctional or bispecific antibodies are artificial hybrid constructs which have two different heavy/light chain pairs, resulting in two different binding sites.

The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk *J. Mol. Biol.* 196:901-917 (1987); Chothia et al. *Nature* 342:878-883 (1989). As used herein, CDRs are referred to for each of the heavy (HCDR1, HCDR2, HCDR3) and light (LCDR1, LCDR2, LCDR3) chains.

An anti-GCC antibody molecule can comprise all, or an antigen binding subset of the CDRs, of one or both, the heavy and light chain, of one of the above-referenced rabbit antibodies. Amino acid sequences of rabbit hybridoma antibodies, including variable regions and CDRs, can be found in Table 3 and Table 5.

Thus, in an embodiment the antibody molecule includes one or both of:

(a) one, two, three, or an antigen binding number of, light chain CDRs (LCDR1, LCDR2 and/or LCDR3) of one of the above-referenced rabbit hybridoma antibodies. In embodiments the CDR(s) may comprise an amino acid sequence of one or more or all of LCDR1-3 as follows:

LCDR1, or modified LCDR1 wherein one to seven amino acids are conservatively substituted)

LCDR2, or modified LCDR2 wherein one or two amino acids are conservatively substituted); or LCDR3, or modified LCDR3 wherein one or two amino acids are conservatively substituted; and (b) one, two, three, or an antigen binding number of, heavy chain CDRs (HCDR1, HCDR2 and/or HCDR3) of one of the above-referenced rabbit hybridoma antibodies. In embodiments the CDR(s) may comprise an amino acid sequence of one or more or all of HCDR1-3 as follows: HCDR1, or modified HCDR1 wherein one or two amino acids are conservatively substituted; HCDR2, or modified HCDR2 wherein one to four amino acids are conservatively substituted; or HCDR3, or modified HCDR3 wherein one or two amino acids are conservatively substituted.

Useful immunogens for production of anti-GCC antibodies include GCC e.g., human GCC-expressing cells (e.g., a tumor cell line, e.g., T84 cells, or fresh or frozen colon tumor cells, recombinant cells expressing GCC); membrane fractions of GCC-expressing cells (e.g., a colon tumor cell line, e.g., T84 cells), or fresh or frozen colonic tumor cells; recombinant cells expressing GCC; isolated or purified GCC, e.g., human GCC protein (e.g., biochemically isolated GCC, e.g., isolated from gastrointestinal tumor cells or recombinant cells expressing GCC or a variant thereof), or a portion thereof (e.g., the extracellular domain of GCC, the kinase homology domain of GCC or the guanylyl cyclase catalytic domain of GCC or peptide corresponding to a portion thereof, e.g., comprising at least about 8, 10, 12, 14, 16, 20, 24, 28 or 32 amino acid residues of SEQ ID NO: 3); or an immunogen comprising SEQ ID NO: 46 or comprising a mature portion thereof without the signal sequence (i.e., without amino acid residues 1 to about 21 or 23 of SEQ ID NO: 46), e.g., the mature hGCC(ECD)-mIgG2a FcR r-mutII (also referred to herein as "pLKTOK108") protein, SEQ ID NO: 48.

Immunogens can be fused to heterologous sequences to aid in biochemical manipulation, purification, immunization or antibody titer measurement. Such immunogens can comprise a portion of GCC, e.g., the extracellular domain, and a portion comprising a non-GCC polypeptide. Many options exist for constructing a fusion protein for ease of purification or immobilization onto a solid support, e.g., an affinity column or a microtiter plate or other suitable assay substrate/chip. For example, a fusion moiety can add a domain, e.g., glutathione-S-transferase/kinase (GST), which can bind glutathione; an Fc region of an immunoglobulin, which can bind to protein A or protein G; amino acid residues, e.g., two, three, four, five, preferably six histidine residues which can bind nickel or cobalt on an affinity column; an epitope tag, e.g., a portion of c-myc oncogene (myc-tag), a FLAG tag (U.S. Pat. No. 4,703,004), a hemagglutinin (HA) tag, a T7 gene 10 tag, a V5 tag, an HSV tag, or a VSV-G tag which can bind a tag-specific antibody; or a cofactor, e.g., biotin, which can bind streptavidin.

Immunogens which comprise the Fc portion of an immunoglobulin can hold the GCC, either in solution or attached to a cell, in a configuration which allows structural access to GCC epitopes by the host immune surveillance components for efficient antibody generation. Because immunoglobulin heavy chains comprising the Fc regions associate into dimers through interchain disulfide bonds, immunogens resulting from fusion with Fc regions are dimers. Valency of fusion proteins can reflect the type of immunoglobulin contributing an Fc region. For example, fusions with IgG proteins can be dimers, IgA fusions can make tetrameric immunogens, and IgM fusions can make decameric immunogens, the latter two is facilitated with co-transfection of the J chain. An exemplary immunoglobulin for an Fc fusion protein is IgG1. The portion used typically has the IgG1 hinge, CH2 and CH3 domains encoded by a single exon. Because this exon also has a portion of the CH1 region, which has a cysteine oriented to disulfide bond with a cysteine from the light chain, a useful modification is to mutate the CH1 cysteine, e.g., to a serine, to ensure there is no unpaired cysteine in the fusion protein. Such a mutation also increases flexibility of the hinge.

An Fc portion derived from a non-host species, e.g., human Ig Fc region, for fusing to an immunogen for immunization in a host species, e.g., mouse, rat, rabbit, goat, acts as an adjuvant. This adjuvant function can trigger specific antibodies against both Fc and GCC epitopes. Fc-reactive antibodies can be identified and discarded during screening. The Fc portion can have a wild type sequence or a sequence which is mutated to modify effector function. For example, a mutated constant region (variant) can be incorporated into a fusion protein to minimize binding to Fc receptors and/or ability to fix complement (see e.g. Winter et al, GB 2,209,757 B; Morrison et al., WO 89/07142; Morgan et al., WO 94/29351). For example, lysine 235 and glycine 237, numbered according to Fc region standards, can be mutated, e.g., to alanine. An immunogen/fusion protein with Fc-mutated IgG can have reduced interaction with Fc receptors in the host. In one embodiment, a soluble immunogen fusion protein (after maturation to cleave the signal peptide and secretion) is hGCC(ECD)-mIgG2a FcR r-mutII (pLKTOK108), which consists of amino acid residues 24 to 430 of SEQ ID NO: 3 fused to mutated mouse IgG2a immunoglobulin Fc (collectively SEQ ID NO:48).

To prepare a cell-expressed immunogen, the immunoglobulin portion can be structured to mimic an immunoglobulin portion of the B cell receptor. For example, the immunoglobulin Fc region can be further fused to a polypeptide comprising a transmembrane region from an immune receptor, such as Fcγ receptors, Fcα receptors, Fcα/μ receptor or Fcε receptors. Proper orientation of such an Fc receptor cell-bound immunogen with adequate exposure on the cell surface may be improved if the cell expressing the immunogen fusion protein further comprises additional components of the antigen receptor complex, e.g., B cell IgM receptor or IgD receptor. Suitable components of the complex include immunoglobulin (Ig) sheath proteins, such as MB-1 and B29 (CD79A and CD79B; Hombach et al. Eur. J. Immunol. 20:2795-2799 (1990) for IgM receptor), which form a heterodimer. The Ig sheath proteins can be provided endogenously by the transfected cell, e.g., if transfecting a B cell lymphoma cell line; or by co-transfection of the immunogen with sheath proteins, e.g., in a separate vector or in the same vector.

Useful epitopes, e.g., reference epitopes, from the GCC molecule, to which the anti-GCC antibody molecules, e.g., rabbit monoclonal antibodies, or humanized versions thereof, as described herein, can bind, can be found on the extracellular portion of GCC. Such GCC epitopes can bind antibody molecules on the surface of cells, e.g., on the cell exterior.

For example, an epitope for an anti-GCC antibody molecule can reside within, or include a residue(s) from, residues 1-50 of SEQ ID NO: 3, or a fragment thereof that binds an anti-GCC antibody molecule of the invention, e.g., a MIL-44-148-2-binding fragment thereof. Such fragments can comprise residues 1-25, 5-30, 10-35, 15-40, 20-45, 25-50, 5-45, 10-40, 15-35, 20-30 or 33-50 of SEQ ID NO: 3. In some embodiments, an epitope for an anti-GCC antibody molecule, e.g., a MIL-44-148-2 antibody, is a conformational epitope further comprising one or more additional amino acid residues in the GCC amino acid sequence beyond residue 50, i.e., selected from about residue 50 to 1073 of SEQ ID NO: 3.

Antibodies raised against such epitopes or the extracellular domain, e.g., epitopes that reside within, or include a residue(s) from amino acid residues 24 to 420 of SEQ ID NO: 3, or a reference portion thereof, e.g., residues 24 to 75, 75 to 150, 150 to 225, 225 to 300, 300 to 375 or 375 to 420 of GCC, or antibody molecules derived therefrom, can be useful as therapeutic or diagnostic antibodies, as described herein.

In an embodiment, the anti-GCC antibody molecule has one or more of the following properties:

a) it competes for binding, e.g., binding to cell surface GCC or purified GCC, with one of the above-referenced anti-GCC antibody molecules summarized in Tables 1 and 2 e.g., rabbit hybridoma antibodies (e.g., MIL-44-148-2);

b) it binds to the same, or substantially the same, epitope on GCC as one of the above-referenced anti-GCC antibody molecules summarized in Tables 1 and 2, e.g., e.g., rabbit hybridoma antibodies (e.g., MIL-44-148-2). In an embodiment, the antibody binds the same epitope, as determined by one or more of a peptide array assay or by binding to truncation mutants, chimeras or point mutants expressed on the cell surface or membrane preparations, e.g., as those assays are described herein;

c) it binds to an epitope which has at least 1, 2, 3, 4, 5, 8, 10, 15 or 20 contiguous amino acid residues in common with the epitope of one of the above-referenced anti-GCC antibody molecules summarized in Tables 1 and 2, e.g., rabbit hybridoma antibodies (e.g., MIL-44-148-2);

d) it binds a region of human GCC that is bound by an anti-GCC antibody of the invention, wherein the region e.g., an extracellular or cytoplasmic region, is 10-15, 10-20, 20-30, or 20-40 residues in length, and binding is determined, e.g., by binding to truncation mutants; In an embodiment the anti-GCC antibody molecule binds the extracellular region of human GCC. In an embodiment an anti-GCC antibody molecule can bind the human GCC portion of the extracellular domain defined by amino acid residues 24 to 420 of SEQ ID NO: 3. In an embodiment an anti-GCC antibody molecule can bind the guanylate cyclase signature site at amino acid residues 931 to 954 of SEQ ID NO: 3; or e) it binds to a reference epitope described herein.

In an embodiment the anti-GCC antibody molecule binds the GCC sequence (SEQ ID NO: 8)
ILVDLFNDQYFEDNVTAPDYMKNVLVLTLS.

In an embodiment the anti-GCC antibody molecule binds the GCC sequence (SEQ ID NO: 9)
FAHAFRNLTFEGYDGPVTLDDWGDV.

In an embodiment the antibody molecule binds a conformational epitope. In other embodiments an antibody molecule binds a linear epitope.

The anti-GCC antibody molecules can be polyclonal antibodies, monoclonal antibodies, monospecific antibodies, chimeric antibodies (See U.S. Pat. No. 6,020,153) or humanized antibodies or antibody fragments or derivatives thereof. Synthetic and genetically engineered variants (See U.S. Pat. No. 6,331,415) of any of the foregoing are also contemplated by the present invention. Monoclonal antibodies can be produced by a variety of techniques, including conventional murine monoclonal antibody methodology (e.g., the standard somatic cell hybridization technique of Kohler and Milstein, Nature 256: 495 (1975); see generally, Harlow, E. and Lane, D. (1988) Antibodies: A Laboratory Manual, Cold Spring Harbor Laboratory Press, Cold Spring Harbor, N.Y.), and the rabbit monoclonal antibody technology and services provided by Epitomics (Burlingame, Calif.) which produces custom rabbit monoclonal antibodies (RabMAbs®) using rabbit-rabbit hybridomas generated by fusing isolated B-cells from an immunized rabbit with Epitomics' proprietary fusion partner cell line, as described in U.S. Pat. Nos. 7,402,409, 7,429, 487, 7,462,697, 7,575,896, 7,732,168, and 8,062,867, each of which are incorporated by reference herein in their entireties.

Immunization with protein, e.g., GCC or a soluble portion, or fusion protein comprising a portion of GCC (e.g., hGCC (ECD)-mIgG2a FcRbr-mutII (pLKTOK108), or cells or membrane fractions therefrom, e.g., cells expressing surface-exposed GCC or a portion thereof (e.g., the pLKTOK4 product), can be performed with the immunogen prepared for injection in a manner to induce a response, e.g., with adjuvant, e.g., complete Freund's adjuvant. Other suitable adjuvants include, Titermax Gold® adjuvant (CYTRX Corporation, Los Angeles, Calif.) and alum. Small peptide immunogens can be linked to a larger molecule, such as keyhole limpet hemocyanin. Mice or rabbits can be injected in a number of manners, e.g., subcutaneous, intravenous or intramuscular at a number of sites, e.g., in the peritoneum (i.p.), base of the tail, or foot pad, or a combination of sites, e.g., iP and base of tail (BIP). Booster injections can include the same or a different immunogen and can additionally include adjuvant, e.g., incomplete Freund's adjuvant. Immunization with DNA, e.g., DNA encoding GCC or a portion thereof or fusion protein comprising GCC or a portion thereof (e.g., encoding hGCC(ECD)-mIgG2a FcRbr-mutII) can be injected using gene gun technology. For example, DNA is loaded onto microscopic gold particles and injected into mice or rabbits at frequent intervals over a brief period.

Generally, where a monoclonal antibody is desired, a hybridoma is produced by fusing a suitable cell from an immortal cell line (e.g., a myeloma cell line such as SP2/0, P3X63Ag8.653 or a heteromyeloma) with antibody-producing cells. Antibody-producing cells can be obtained from the peripheral blood or, preferably the spleen or lymph nodes, of humans, human-antibody transgenic animals or other suitable animals (e.g., rabbits) immunized with the antigen of interest. Cells that produce antibodies of human origin (e.g., a human antibody) can be produced using suitable methods, for example, fusion of a human antibody-producing cell and a heteromyeloma or trioma, or immortalization of an activated human B cell via infection with Epstein Barr virus. (See, e.g., U.S. Pat. No. 6,197,582 (Trakht); Niedbala et al., Hybridoma, 17:299-304 (1998); Zanella et al., J Immunol Methods, 156:205-215 (1992); Gustafsson et al., Hum Antibodies Hybridomas, 2:26-32 (1991).) The fused or immortalized antibody-producing cells (hybridomas) can be isolated using selective culture conditions, and cloned by limiting dilution. Cells which produce antibodies with the desired specificity can be identified using a suitable assay (e.g., ELISA (e.g., with immunogen, e.g., hGCC(ECD)-mIgG2a FcRbr-mutII, immobilized on the microtiter well) or by FACS on a cell expressing GCC or a portion thereof, e.g., a cell expressing the pLKTOK4 product). For example, if the GCC-immunogen comprises a fusion moiety that is an affinity reagent, this moiety can allow the fusion protein comprising GCC or a portion thereof to be bound to a matrix, e.g., protein G-coated, streptavidin-coated, glutathione-derivatized or antibody-coated microtitre plates or assay chips, which are then combined with the immune serum or conditioned medium from a hybridoma or antibody-expressing recombinant cell, and the mixture incubated under conditions conducive to complex formation (e.g., at physiological conditions for salt and pH). Following incubation, the microtitre plate wells or chip cells are washed to remove any unbound components and binding by anti-GCC antibody is measured.

In embodiments, for therapeutic applications, the antibodies of the present invention are humanized antibodies. The advantage of humanized antibodies is that they potentially decrease or eliminate the immunogenicity of the antibody in a host recipient, thereby permitting an increase in the bioavailability and a reduction in the possibility of adverse immune reaction, thus potentially enabling multiple antibody administrations.

Modified antibodies include humanized, chimeric or CDR-grafted antibodies. Human anti-mouse antibody (HAMA) responses have led to development of chimeric or otherwise humanized antibodies. While chimeric antibodies have a human constant region and a non-human variable region, it is expected that certain human anti-chimeric antibody (HACA) responses will be observed, particularly in chronic or multi-dose utilizations of the antibody. The presence of such non-human (e.g., murine, rat, rabbit, sheep or goat) derived proteins can lead to the rapid clearance of the antibodies or can lead to the generation of an immune response against the antibody by a patient. In order to avoid the utilization of non-human derived antibodies, humanized antibodies where sequences are introduced to an antibody sequence to make it closer to human antibody sequence, or fully human antibodies generated by the introduction of human antibody function into a non-human species, such as a mouse, rat, rabbit, sheep or goat, have been developed so that the non-human species would produce antibodies having fully human sequences. Human antibodies avoid certain of the problems associated with antibodies that possess rabbit, rodent, sheep or goat variable and/or constant regions.

Humanization and Display Technologies and Modifications to Antibodies

Humanized antibody molecules can minimize the immunogenic and allergic responses intrinsic to non-human or non-human-derivatized mAbs and thus to increase the efficacy and safety of the administered antibodies. The use of humanized antibody molecules can provide a substantial advantage in the treatment of chronic and recurring human diseases, such as inflammation, autoimmunity, and cancer, which require repeated antibody administrations. In one aspect, a therapeutic antibody molecule is a humanized antibody prepared from the sequences in rabbit antibodies MIL-44-148-2 or MIL-44-67-4. In some embodiments, the variable regions provided in Tables 3 and 4 and/or the CDRs provided in Tables 5 and 6, or variations of any of the foregoing, can be incorporated in a humanized anti-GCC antibody molecule.

The production of humanized antibodies with reduced immunogenicity can be accomplished in connection with techniques of humanization and display techniques using appropriate libraries. It will be appreciated that antibodies from non-human species, such as mice, rats, rabbits, sheep, goats, etc., can be humanized or primatized using techniques known in the art. See e.g., Winter and Harris Immunol Today 14:43-46 (1993) and Wright et al. *Crit. Reviews in Immunol.* 12125-168 (1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al. *Proc Natl Acad Sci* USA. 84:3439 (1987) and J. Immunol. 139:3521 (1987)). mRNA is isolated from a hybridoma or other cell producing the antibody and used to produce cDNA: The cDNA of interest may be amplified by the polymerase chain reaction using specific primers (U.S. Pat. Nos. 4,683,195 and 4,683,202).

Alternatively, phage display technology (see, e.g., McCafferty et al, *Nature*, 348:552-553 (1990)) can be used to produce human antibodies or antibodies from other species, as well as antibody fragments in vitro, from immunoglobulin variable (V) domain genes, e.g., from repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson and Chiswell, *Current Opinion in Structural Biology*, 3:564-571 (1993). Several sources of V-gene segments can be used for phage display. Clackson et al., *Nature*, 352: 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.*, 222: 581-597 (1991), or Griffith et al, *EMBO J.*, 12:725-734 (1993). See, also, U.S. Pat. Nos. 5,565,332 and 5,573,905. Display libraries can contain antibodies or antigen-binding fragments of antibodies that contain artificial amino acid sequences. For example, the library can contain Fab fragments which contain artificial CDRs (e.g., random amino acid sequences) and human framework regions. (See, for example, U.S. Pat. No. 6,300,064 (Knappik, et al.).)

The sequences of human constant region genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. Isotypes can be IgG1, IgG2, IgG3 or IgG4. In particular embodiments, antibody molecules of the invention are IgG1 and IgG2. Either of the human light chain constant regions, kappa or lambda, may be used. The chimeric, humanized antibody is then expressed by conventional methods.

In some embodiments, an anti-GCC antibody molecule of the invention can draw antibody-dependent cellular cytotoxicity (ADCC) to a cell expressing GCC, e.g., a tumor cell. Antibodies with the IgG1 and IgG3 isotypes are useful for eliciting effector function in an antibody-dependent cytotoxic capacity, due to their ability to bind the Fc receptor. Antibodies with the IgG2 and IgG4 isotypes are useful to minimize an ADCC response because of their low ability to bind the Fc receptor. In related embodiments substitutions in the Fc region or changes in the glycosylation composition of an antibody, e.g., by growth in a modified eukaryotic cell line, can be made to enhance the ability of Fc receptors to recognize, bind, and/or mediate cytotoxicity of cells to which anti-GCC antibodies bind (see, e.g., U.S. Pat. Nos. 7,317,091, 5,624,821 and publications including WO 00/42072, Shields, et al. *J. Biol. Chem.* 276:6591-6604 (2001), Lazar et al. *Proc. Natl. Acad. Sci.* U.S.A. 103:4005-4010 (2006), Satoh et al. *Expert Opin Biol. Ther.* 6:1161-1173 (2006)). In certain embodiments, the antibody or antigen-binding fragment (e.g., antibody of human origin, human antibody) can include amino acid substitutions or replacements that alter or tailor function (e.g., effector function). For example, a constant region of human origin (e.g., γ1 constant region, γ2 constant region) can be designed to reduce complement activation and/or Fc receptor binding. (See, for example, U.S. Pat. No. 5,648,260 (Winter et al.), U.S. Pat. No. 5,624,821 (Winter et al.) and U.S. Pat. No. 5,834,597 (Tso et al.), the entire teachings of which are incorporated herein by reference.) Preferably, the amino acid sequence of a constant region of human origin that contains such amino acid substitutions or replacements is at least about 95% identical over the full length to the amino acid sequence of the unaltered constant region of human origin, more preferably at least about 99% identical over the full length to the amino acid sequence of the unaltered constant region of human origin.

In still another embodiment, effector functions can also be altered by modulating the glycosylation pattern of the antibody. By altering is meant deleting one or more carbohydrate moieties found in the antibody, and/or adding one or more glycosylation sites that are not present in the antibody. For example, antibodies with enhanced ADCC activities with a mature carbohydrate structure that lacks fucose attached to an Fc region of the antibody are described in U.S. Patent Application Publication No. 2003/0157108 (Presta). See also U.S. Patent Application Publication No. 2004/0093621 (Kyowa Hakko Kogyo Co., Ltd). Glycofi has also developed yeast cell lines capable of producing specific glycoforms of antibodies.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which are engineered to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 *J. Biol. Chem.* 277:26733-26740). PCT Publication WO 99/54342 by Umana et al. describes cell lines engineered to express glycoprotein-modifying glycosyl transferases (e.g., beta(1,4)-N acetylglucosaminyltransferase 111 (GnTIII)) such that antibodies expressed in the engineered cell lines exhibit increased bisecting GlcNac structures which results in increased ADCC activity of the antibodies (see also Umana et al., 1999 *Nat. Biotech*. 17:176-180).

Humanized antibodies can also be made using a CDR-grafted approach. Techniques of generation of such humanized antibodies are known in the art. Generally, humanized antibodies are produced by obtaining nucleic acid sequences that encode the variable heavy and variable light sequences of an antibody that binds to GCC, identifying the complementary determining region or "CDR" in the variable heavy and variable light sequences and grafting the CDR nucleic acid sequences on to human framework nucleic acid sequences. (See, for example, U.S. Pat. Nos. 4,816,567 and 5,225,539). The location of the CDRs and framework residues can be determined (see, Kabat, E. A., et al. (1991) Sequences of Proteins of Immunological Interest, Fifth Edition, U.S. Department of Health and Human Services, NIH Publication No. 91-3242, and Chothia, C. et al. J. Mol. Biol. 196:901-917 (1987)). Anti-GCC antibody molecules described herein have the CDR amino acid sequences and nucleic acid sequences encoding CDRs listed in Tables 5 and 6. In some embodiments sequences from Tables 5 and 6 can be incorporated into molecules which recognize GCC for use in the therapeutic or diagnostic methods described herein. The human framework that is selected is one that is suitable for in vivo administration, meaning that it does not exhibit immunogenicity. For example, such a determination can be made by prior experience with in vivo usage of such antibodies and studies of amino acid similarities. A suitable framework region can be selected from an antibody of human origin having at least about 65% amino acid sequence identity, and preferably at least about 70%, 80%, 90% or 95% amino acid sequence identity over the length of the framework region within the amino acid sequence of the equivalent portion (e.g., framework region) of the donor antibody, e.g., an anti-GCC antibody molecule (e.g., 3G1). Amino acid sequence identity can be determined using a suitable amino acid sequence alignment algorithm, such as CLUSTAL. W, using the default parameters. (Thompson J. D. et al., Nucleic Acids Res. 22:4673-4680 (1994).)

Once the CDRs and FRs of the cloned antibody that are to be humanized are identified, the amino acid sequences encoding the CDRs are identified and the corresponding nucleic acid sequences grafted on to selected human FRs. This can be done using known primers and linkers, the selection of which are known in the art. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen. After the CDRs are grafted onto selected human FRs, the resulting "humanized" variable heavy and variable light sequences are expressed to produce a humanized Fv or humanized antibody that binds to GCC. Preferably, the CDR-grafted (e.g., humanized) antibody binds a GCC protein with an affinity similar to, substantially the same as, or better than that of the donor antibody. Typically, the humanized variable heavy and light sequences are expressed as a fusion protein with human constant domain sequences so an intact antibody that binds to GCC is obtained. However, a humanized Fv antibody can be produced that does not contain the constant sequences.

Also within the scope of the invention are humanized antibodies in which specific amino acids have been substituted, deleted or added. In particular, humanized antibodies can have amino acid substitutions in the framework region, such as to improve binding to the antigen. For example, a selected, small number of acceptor framework residues of the humanized immunoglobulin chain can be replaced by the corresponding donor amino acids. Locations of the substitutions include amino acid residues adjacent to the CDR, or which are capable of interacting with a CDR (see e.g., U.S. Pat. No. 5,585,089 or 5,859,205). The acceptor framework can be a mature human antibody framework sequence or a consensus sequence. As used herein, the term "consensus sequence" refers to the sequence found most frequently, or devised from the most common residues at each position in a sequence in a region among related family members. A number of human antibody consensus sequences are available, including consensus sequences for the different subgroups of human variable regions (see, Kabat, E. A., et al., Sequences of Proteins of Immunological Interest, Fifth Edition, U.S. Department of Health and Human Services, U.S. Government Printing Office (1991)). The Kabat database and its applications are freely available on line, e.g. via IgBLAST at the National Center for Biotechnology Information, Bethesda, Md. (also see, Johnson, G. and Wu, T. T., Nucleic Acids Research 29:205-206 (2001)).

Other techniques for humanizing antibodies are described in Padlan et al. EP 519596 A1, published on Dec. 23, 1992.

The anti-GCC antibody molecule includes other humanized antibodies which may also be modified by specific deletion of human T cell epitopes or "deimmunization" by the methods disclosed in PCT Publication Nos. WO 98/52976 and WO 00/34317, the contents of which are incorporated herein by reference. Briefly, the rabbit, or other non-human species, heavy and light chain variable regions of an anti-GCC antibody can be analyzed for peptides that bind to MHC Class II; these peptides represent potential T-cell epitopes. For detection of potential T-cell epitopes, a computer modeling approach termed "peptide threading" can be applied, and in addition a database of human MHC class 11 binding peptides can be searched for motifs present in the rabbit VH and VL sequences, as described in PCT Publication Nos. WO 98/52976 and WO 00/34317. These motifs bind to any of the 18 major MHC class 11 DR allotypes, and thus constitute potential T cell epitopes. Potential T-cell epitopes detected can be eliminated by substituting small numbers of amino acid residues in the variable regions, or preferably, by single amino acid substitutions. As far as possible, conservative substitutions are made, often but not exclusively, an amino acid common at this position in human germline antibody sequences may be used. Human germline sequences are disclosed in Tomlinson, I. A. et al., *J. Mol. Biol.* 227:776-798 (1992); Cook, G. P. et al., Immunol. Today Vol. 16 (5): 237-242 (1995); Chothia, D. et al., *J. Mol. Bio.* 227:799-817 (1992). The V BASE directory provides a comprehensive directory of human immunoglobulin variable region sequences (compiled by Tomlinson, I. A. et al. MRC Centre for Protein Engineering, Cambridge, UK). After the deimmunized VH and VL of an anti-GCC antibody are constructed by mutagenesis of the rabbit VH and VL genes, the mutagenized variable sequence can, optionally, be fused to a human constant region, e.g., human IgG1 or K (kappa) constant regions.

In other embodiments, reduction of an immunogenic response by a CDR-grafted antibody can be achieved by changes, e.g., deletions, substitutions, of amino acid residues in CDRs (Kashmiri et al. Methods 36:25-34 (2005), U.S. Pat. No. 6,818,749, Tan et al. *J. Immunol.* 169:1119-1125 (2006)). For example, residues at positions involved in contact with the antigen preferably would not be changed. Typically, such residues, the specificity determining residues (SDRs), are in positions which display high levels of variability among antibodies. Consensus sequences derived, e.g., by the Clustal method (Higgins D. G. et al., Meth. Enzymol. 266:383-402 (1996)), from anti-GCC antibody molecules, e.g., from antibodies described herein, aid in identifying SDRs. In the anti-GCC antibody molecules described herein, the SDRs are the following, at least the first residue or in some embodiments, the first four residues of heavy chain CDR1; at least the N-terminal portion, e.g., the first seven, ten or 13 residues of heavy chain CDR2; nearly all of heavy chain CDR3; the C-terminal portion, e.g., after residue six, eight, or nine of light chain CDR1; about the first, middle and/or last residue of light chain CDR2; and most of light chain CDR3, or at least after residue two or three. Accordingly, to maintain binding to GCC protein after humanization or modification of an anti-GCC antibody molecule, such SDR residues in CDRs of the anti-GCC antibody molecules are less amenable to changes, e.g., from rabbit residues to human consensus residues than are residues in other residues of the CDRs or the framework regions. Conversely, it can be beneficial to change residues in non-human, e.g., rabbit CDRs to residues identified as consensus in human CDRs, e.g., CDRs of anti-GCC antibody molecules described in US Published Patent Application No. 20110110936, the contents of which are incorporated by reference herein in its entirety.

Anti-GCC antibodies that are not intact antibodies are also useful in this invention. Such antibodies may be derived from any of the antibodies described above. Useful antibody molecules of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., Nature 341:544-546 (1989)), which consists of a VH domain; (vii) a single domain functional heavy chain antibody, which consists of a VHH domain (known as a nanobody) see e.g., Cortez-Retamozo, et al., *Cancer Res*. 64: 2853-2857 (2004), and references cited therein; and (vii) an isolated CDR, e.g., one or more isolated CDRs together with sufficient framework to provide an antigen binding fragment. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. *Science* 242:423-426 (1988); and Huston et al. *Proc. Natl. Acad. Sci.* USA 85:5879-5883 (1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antibody fragments, such as Fv, F(ab')$_2$ and Fab may be prepared by cleavage of the intact protein, e.g. by protease or chemical cleavage.

In embodiments, some or all of the CDRs sequences, of one or both the heavy and light chain, can be used in another antibody molecule, e.g., in a CDR-grafted, humanized, or chimeric antibody molecule.

Embodiments include an antibody molecule that comprises sufficient CDRs, e.g., all six CDRs from one of the rabbit hybridoma antibodies described herein to allow binding to cell surface GCC.

In an embodiment the CDRs, e.g., all of the HCDRs, or all of the LCDRs, or all six, are embedded in human or human derived framework region(s). Examples of human framework regions include human germline framework sequences, human germline sequences that have been affinity matured (either in vivo or in vitro), or synthetic human sequences, e.g., consensus sequences. In an embodiment the heavy chain framework is an IgG1 or IgG2 framework. In an embodiment the light chain framework is a kappa framework.

In an embodiment the anti-GCC antibody molecule, e.g., a CDR-grafted or humanized antibody molecule, comprises sufficient CDRs, e.g., all six CDRs from one of the antibodies described herein, e.g., sequences listed in Table 5, to allow binding to GCC. (Exemplary nucleic acid sequences which can encode the CDR amino acid sequences listed in Table 5, are provided, in Table 6 herein). In particular embodiments, an anti-GCC antibody molecule can comprise CDRs from MIL-44-148-2 or MIL-44-67-4.

Antibody fragments for in vivo therapeutic or diagnostic use can benefit from modifications which improve their serum half lives. Suitable organic moieties intended to increase the in vivo serum half-life of the antibody can include one, two or more linear or branched moiety selected from a hydrophilic polymeric group (e.g., a linear or a branched polymer (e.g., a polyalkane glycol such as polyethylene glycol, monomethoxy-polyethylene glycol and the like), a carbohydrate (e.g., a dextran, a cellulose, a polysaccharide and the like), a polymer of a hydrophilic amino acid (e.g., polylysine, polyaspartate and the like), a polyalkane oxide and polyvinyl pyrrolidone), a fatty acid group (e.g., a mono-carboxylic acid or a di-carboxylic acid), a fatty acid ester group, a lipid group (e.g., diacylglycerol group, sphingolipid group (e.g., ceramidyl)) or a phospholipid group (e.g., phosphatidyl ethanolamine group). Preferably, the organic moiety is bound to a predetermined site where the organic moiety does not impair the function (e.g., decrease the antigen binding affinity) of the resulting immunoconjugate compared to the non-conjugated antibody moiety. The organic moiety can have a molecular weight of about 500 Da to about 50,000 Da, preferably about 2000, 5000, 10,000 or 20,000 Da. Examples and methods for modifying polypeptides, e.g., antibodies, with organic moieties can be found, for example, in U.S. Pat. Nos. 4,179,337 and 5,612,460, PCT Publication Nos. WO 95/06058 and WO 00/26256, and U.S. Patent Application Publication No. 20030026805.

An anti-GCC antibody molecule can comprise all, or an antigen binding fragment of the variable region, of one or both, the heavy and light chain, of one of the above-referenced rabbit hybridoma antibodies.

In an embodiment the light chain amino acid sequence of (a) can differ from one of the reference amino acid sequence(s) referred to in (a)(i-ii) by as many as 1, 2, 3, 4, 5, 10, or 15 residues. In embodiments the differences are conservative substitutions. In embodiments, the differences are in the framework regions. In an embodiment the heavy chain amino acid sequence of (b) can differ from one of the reference amino acid sequence(s) referred to in (b)(i-ii) by as many as 1, 2, 3, 4, 5, 10, or 15 residues. In embodiments the differences are conservative substitutions. In embodiments the differences are in the framework regions.

In an embodiment the anti-GCC antibody molecule comprises one or both of:

(a) a light chain amino acid sequence of all, or an antigen binding fragment of, either, (i) a light chain variable region amino acid sequence from Table 3, e.g., SEQ ID NO:13, or (ii) a light chain variable region amino acid encoded by a nucleotide sequence from Table 4, e.g., SEQ ID NO:12; and (b) a heavy chain amino acid sequence of all, or an antigen binding fragment of, either (i) a heavy chain variable region amino acid sequence from Table 3, e.g., SEQ ID NO:11, or (ii) a heavy chain amino acid sequence encoded by a nucleotide sequence from Table 4, e.g., SEQ ID NO:10.

In an embodiment the anti-GCC antibody molecule comprises one or both of:

a) a light chain variable region, or an antigen binding fragment thereof, having at least 85, 90, 95, 97 or 99% homology with the light chain variable region of an anti-GCC antibody molecule of the invention; and (b) a heavy chain variable region, or an antigen binding fragment thereof, having at least 85, 90, 95, 97 or 99% homology with the heavy chain variable region of an anti-GCC antibody molecule of the invention.

Amino acid sequences of the variable regions of the anti-GCC antibodies of the invention can be found in Table 3.

In one approach, consensus sequences encoding the heavy and light chain J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, cosmids, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Suitable expression vectors can contain a number of components, for example, an origin of replication, a selectable marker gene, one or more expression control elements, such as a transcription control element (e.g., promoter, enhancer, terminator) and/or one or more translation signals, a signal sequence or leader sequence, and the like. Polyadenylation and transcription termination occur at native chromosomal sites downstream of the coding regions. The resulting chimeric antibody may be joined to any strong promoter. Examples of suitable vectors that can be used include those that are suitable for mammalian hosts and based on viral replication systems, such as simian virus 40 (SV40), Rous sarcoma virus (RSV), adenovirus 2, bovine papilloma virus (BPV), papovavirus BK mutant (BKV), or mouse and human cytomegalovirus (CMV), and moloney murine leukemia virus (MMLV), native Ig promoters, etc. A variety of suitable vectors are known in the art, including vectors which are maintained in single copy or multiple copies, or which become integrated into the host cell chromosome, e.g., via LTRs, or via artificial chromosomes engineered with multiple integration sites (Lindenbaum et al. Nucleic Acids Res. 32:e172 (2004), Kennard et al. Biotechnol. Bioeng. Online May 20, 2009). Additional examples of suitable vectors are listed in a later section.

Thus, the invention provides an expression vector comprising a nucleic acid encoding an antibody, antigen-binding fragment of an antibody (e.g., a humanized, chimeric antibody or antigen-binding fragment of any of the foregoing), antibody chain (e.g., heavy chain, light chain) or antigen-binding portion of an antibody chain that binds a GCC protein.

Expression in eukaryotic host cells is useful because such cells are more likely than prokaryotic cells to assemble and secrete a properly folded and immunologically active antibody. However, any antibody produced that is inactive due to improper folding may be renaturable according to known methods (Kim and Baldwin, "Specific Intermediates in the Folding Reactions of Small Proteins and the Mechanism of Protein Folding", Ann. Rev. Biochem. 51, pp. 459-89 (1982)). It is possible that the host cells will produce portions of intact antibodies, such as light chain dimers or heavy chain dimers, which also are antibody homologs according to the present invention.

Further, as described elsewhere herein, antibodies or antibodies from human or non-human species can be generated through display-type technologies, including, without limitation, phage display, retroviral display, ribosomal display, and other techniques, using techniques well known in the art and the resulting molecules can be subjected to additional maturation, such as affinity maturation, as such techniques are known in the art. Winter and Harris Immunol Today 14:43-46 (1993) and Wright et al. Crit. Reviews in Immunol. 12125-168 (1992), Hanes and Plucthau PNAS USA 94:4937-4942 (1997) (ribosomal display), Parmley and Smith Gene 73:305-318 (1988) (phage display), Scott TIBS 17:241-245 (1992), Cwirla et al. Proc Natl Acad Sci USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH 10:80-84 (1992), and U.S. Pat. No. 5,733,743. If display technologies are utilized to produce antibodies that are not human, such antibodies can be humanized as described above.

It will be appreciated that antibodies that are generated need not initially possess a particular desired isotype but, rather, the antibody as generated can possess any isotype. For example, the antibody produced by the MIL-44-148-2 rabbit hybridoma has an IgG isotype. The isotype of the antibody can be switched thereafter, e.g., to IgG2, or IgG3 to elicit an ADCC response when the antibody binds GCC on a cell, using conventional techniques that are known in the art. Such techniques include the use of direct recombinant techniques (see e.g., U.S. Pat. No. 4,816,397), cell-cell fusion techniques (see e.g., U.S. Pat. No. 5,916,771), among others. In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

In certain embodiments, the GCC antibody molecule is a rabbit anti-GCC IgG1 antibody. Since such antibodies possess desired binding to the GCC molecule, any one of such antibodies can be readily isotype-switched to generate another isotype while still possessing the same variable region (which defines the antibody's specificity and affinity, to a certain extent). Accordingly, as antibody candidates are generated that meet desired "structural" attributes as discussed above, they can generally be provided with at least certain additional "functional" attributes that are desired through isotype switching.

In an embodiment the variable region or antigen binding fragment thereof can be coupled to a constant region (or fragment thereof) other than the constant region it was generated with, e.g., a constant region (or fragment thereof) from another antibody or to a synthetic constant region (or fragment thereof). In embodiments the constant region is an IgG1 or IgG2 constant region (or fragment thereof). Sequence changes can be made in the variable or constant regions to modify effector activity of the antibody molecule.

Design and Generation of Other Therapeutics

The antibodies that are produced and characterized herein with respect to GCC provide for the design of other therapeutic modalities including other antibodies, other antagonists, or chemical moieties other than antibodies is facilitated. Such modalities include, without limitation, antibodies having similar binding activity or functionality, advanced antibody therapeutics, such as bispecific antibodies, immunoconjugates, and radiolabeled therapeutics, generation of peptide therapeutics, particularly intrabodies, and small molecules. Furthermore, as discussed above, the effector function of the antibodies of the invention may be changed by isotype switching to an IgG1, IgG2, IgG3, IgG4, IgD, IgA1, IgA2, IgE, or IgM for various therapeutic uses.

In connection with bispecific antibodies, bispecific antibodies can be generated that comprise (i) two antibodies, one with a specificity to GCC and another to a second molecule that are conjugated together, (ii) a single antibody that has one chain specific to GCC and a second chain specific to a second molecule, or (iii) a single chain antibody that has specificity to GCC and the other molecule. Such bispecific antibodies can be generated using techniques that are known. For example, bispecific antibodies may be produced by crosslinking two or more antibodies (of the same type or of different types). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill. See also, e.g., Fanger et al. *Immunomethods* 4:72-81 (1994) and Winter and Harris *Immunol Today* 14:43-46 (1993) and Wright et al. *Crit. Reviews in Immunol.* 12125-168 (1992) and in connection with (iii) see e.g., Traunecker et al. *Int. J. Cancer* (Suppl.) 7:51-52 (1992). Songsivilai & Lachmann *Clin. Exp. Immunol.* 79: 315-321 (1990), Kostelny et al. *J. Immunol.* 148: 1547-1553 (1992).

In addition, "Kappabodies" (Ill. et al. "Design and construction of a hybrid immunoglobulin domain with properties of both heavy and light chain variable regions" *Protein Eng* 10:949-57 (1997)), "Minibodies" (Martin et al. *EMBO J.* 13:5303-9 (1994), U.S. Pat. No. 5,837,821), "Diabodies" (Holliger et al. *Proc Natl Acad Sci* USA 90:6444-6448 (1993)), or "Janusins" (Traunecker et al. *EMBO J.* 10:3655-3659 (1991) and Traunecker et al. *Int J Cancer Suppl* 7:51-52 (1992)) may also be prepared.

Nucleic Acids and Polypeptides

In another embodiment, the present invention relates to polynucleotide and polypeptide sequences that encode for or represent the antibody molecules described herein. Such polynucleotides encode for both the variable and constant regions of each of the heavy and light chains, although other combinations are also contemplated by the present invention in accordance with the compositions described herein. The present invention also contemplates oligonucleotide fragments derived from the disclosed polynucleotides and nucleic acid sequences complementary to these polynucleotides.

The polynucleotides can be in the form of RNA or DNA. Polynucleotides in the form of DNA, cDNA, genomic DNA, nucleic acid analogs and synthetic DNA are within the scope of the present invention. The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence which coding sequence, as a result of the redundancy or degeneracy of the genetic code, encodes the same polypeptide as the DNA provided herein.

In embodiments provided, polynucleotides encode at least one heavy chain variable region and at least one light chain variable region of the present invention, e.g., as summarized in Table 4.

The present invention also includes variant polynucleotides containing modifications such as polynucleotide deletions, substitutions or additions, and any polypeptide modification resulting from the variant polynucleotide sequence. A polynucleotide of the present invention may also have a coding sequence that is a variant of the coding sequence provided herein. For example, a variant polynucleotide can have at least 50%, 60%, 70%, 75%, 80%, 85%, 90%, 95% or 97% identity with a polynucleotide listed in Table 4. In embodiments, the variant polynucleotide encodes for an anti-GCC antibody molecule.

The present invention further relates to polypeptides that represent the antibodies of the present invention as well as fragments, analogs and derivatives of such polypeptides. The polypeptides of the present invention may be recombinant polypeptides, naturally produced polypeptides or synthetic polypeptides. The fragment, derivative or analogs of the polypeptides of the present invention may be one in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence that is employed for purification of the polypeptide or a proprotein sequence. Such fragments, derivatives and analogs are within the scope of the present invention. In various aspects, the polypeptides of the invention may be partially purified, or purified product.

A polypeptide of the present invention can have an amino acid sequence that is identical to that of the antibodies described herein, e.g., summarized in Tables 2 or 3, or that is different by minor variations due to one or more amino acid substitutions. The variation may be a "conservative change" typically in the range of about 1 to 5 amino acids, wherein the substituted amino acid has similar structural or chemical properties, e.g., replacement of leucine with isoleucine or threonine with serine; replacement of lysine with arginine or histidine. In contrast, variations may include nonconservative changes, e.g., replacement of a glycine with a tryptophan. Similar minor variations may also include amino acid deletions or insertions or both. Guidance in determining which and how many amino acid residues may be substituted, inserted, or deleted without changing biological or immunological activity may be found using computer programs known in the art, for example DNASTAR software (DNASTAR, Inc., Madison, Wis.).

In another aspect, the invention features, isolated and/or recombinant nucleic acids encoding anti-GCC antibody molecules. In embodiments, the nucleic acids encode one or more of an antibody molecule, a heavy chain, a light chain, a light chain variable region, a heavy chain variable region, portions of the heavy chains and light chains of the antibody molecules described herein (e.g., a light chain variable region fragment which when paired with a full length heavy chain variable region is antigen binding, or a heavy chain variable region fragment which when paired with a full length light chain variable region is antigen binding), and CDRs. Embodiments include such nucleic acids disposed in vectors, e.g., expression vectors. Still further, the invention encompasses antibody molecules produced by host cells, e.g., expressing the antibody molecules encoded by such plasmids In an embodiment, is provided a vector, e.g., an expression vector, comprising one or both of:

sequences encoding a light chain variable region, e.g., sequences listed in Table 4, an antigen binding fragment thereof, or one, two or three CDRs from a light chain (and optionally a framework region), described herein, e.g., in Table 6; and sequences encoding a heavy chain variable region, e.g., sequences listed in Table 4, an antigen binding fragment thereof, or one, two or three CDRs from a heavy chain (and optionally a framework region), described herein, e.g., in Table 6.

In embodiments provided, polynucleotides encode at least one heavy chain variable region or at least one light chain variable region of the antibodies of the present invention. In embodiments provided, polypeptides can encode at least one heavy chain variable region and one light chain variable region of the antibodies of the present invention.

In an embodiment the anti-GCC antibody molecule comprises one or both of:

(a) a light chain variable region, or an antigen binding fragment thereof, encoded by a nucleic acid that hybridizes under selected stringency conditions with, (i) the complement of an anti-GCC antibody molecule-encoding-nucleic acid sequence described herein, e.g., in Table 4, or (ii) any nucleic acid sequence that encodes a light chain of an anti-GCC antibody molecule of the invention, e.g., one of the above-referenced rabbit hybridoma antibodies summarized in Tables 1 and 2; and (b) a heavy chain variable region, or an antigen binding fragment thereof, encoded by a nucleic acid that hybridizes under selected stringency conditions with, (i) the complement of an anti-GCC antibody molecule-encoding-nucleic acid sequence described herein, e.g., in Table 4, or (ii) any nucleic acid sequence that encodes a heavy chain of an anti-GCC antibody molecule of the invention, e.g., one of the above-referenced rabbit hybridoma antibodies summarized in Tables 1 and 2.

In an embodiment selected stringency conditions are high stringency or very high stringency conditions, e.g., as those conditions are described herein.

The present invention also provides vectors that include the polynucleotides of the present invention, host cells which are genetically engineered with vectors of the present invention and the production of the antibodies of the present invention by recombinant techniques.

The appropriate DNA sequence may be inserted into the vector by a variety of procedures. In general, the DNA sequence is inserted into appropriate restriction endonuclease sites by procedures known in the art. The polynucleotide sequence in the expression vector is operatively linked to an appropriate expression control sequence (i.e. promoter) to direct mRNA synthesis. Examples of such promoters include, but are not limited to, the Rous sarcoma virus LTR or the early or late SV40 promoter, the $E.\ coli$ lac or trp, the phage lambda $P_L$ promoter and other promoters known to control expression of genes in prokaryotic (e.g., tac, T3, T7 promoters for $E.\ coli$) or eukaryotic (e.g., cytomegalovirus promoter, adenovirus late promoter, EF-1a promoter) cells or their viruses. The expression vector also contains a ribosome binding site for translation initiation and a transcription terminator. The vector may also include appropriate sequences for amplifying expression. For example, the vector can contain enhancers, which are transcription-stimulating DNA sequences of viral origin, such as those derived form simian virus such as SV40, polyoma virus, cytomegalovirus, bovine papilloma virus or Moloney sarcoma virus, or genomic, origin. The vector preferably also contains an origin of replication. The vector can be constructed to contain an exogenous origin of replication or, such an origin of replication can be derived from SV40 or another viral source, or by the host cell chromosomal replication mechanism.

In addition, the vectors optionally contain a marker gene for selection of transfected host cells such as dihydrofolate reductase marker genes to permit selection with methotrexate in a variety of hosts, or antibiotics, such as β-lactamase gene (ampicillin resistance), Tet gene (for tetracycline resistance) used in prokaryotic cells or neomycin, GA418 (geneticin, a neomycin-derivative) gpt (mycophenolic acid), ampicillin, or hygromycin resistance genes, or genes which complement a genetic lesion of the host cells such as the absence of thymidine kinase, hypoxanthine phosphoribosyl transferase, dihydrofolate reductase, etc. Genes encoding the gene product of auxotrophic markers of the host (e.g., LEU2, URA3, HIS3) are often used as selectable markers in yeast.

In order to obtain the antibodies of the present invention, one or more polynucleotide sequences that encode for the light and heavy chain variable regions and light and heavy chain constant regions of the antibodies of the present invention should be incorporated into a vector. Polynucleotide sequences encoding the light and heavy chains of the antibodies of the present invention can be incorporated into one or multiple vectors and then incorporated into the host cells.

Suitable expression vectors for expression in mammalian cells include, for example, pCDM8, pcDNA1.1/amp, pcDNA3.1, pRc/RSV, pEF-1 (Invitrogen Life Technologies, Carlsbad, Calif.), pCMV-SCRIPT, pFB, pSG5, pXT1 (Stratagene, La Jolla, Calif.), pCDEF3 (Goldman, L. A., et al., *Biotechniques*, 21:1013-1015 (1996)), pSVSPORT (GIBCO division of Invitrogen Life Technologies, Carlsbad, Calif.), pEF-Bos (Mizushima, S., et al., *Nucleic Acids Res.*, 18:5322 (1990)), Bicistronic GPEX® Retrovector (Gala Biotech, Middleton, Wis.) and the like. Expression vectors which are suitable for use in various expression hosts, such as prokaryotic cells (*E. coli*), insect cells (*Drosophila* Schnieder S2 cells, Sf9) and yeast (*P. methanolica. P. pasloris, S. cerevisiae*) are also available. Exemplary vectors are pLKTOK58 (wild type IgG1 Fe sequence) and pLKTOK59 (mutated IgG1 Fc sequence) (see U.S. Patent Application publication no. 20060147445).

As will be appreciated, antibodies in accordance with the present invention can be expressed in cell lines other than hybridoma cell lines. Sequences encoding the cDNAs or genomic clones for the particular antibodies can be used for a suitable mammalian or nonmammalian host cells. Transformation can be by any known method for introducing polynucleotides into a host cell, including, for example packaging the polynucleotide in a virus (or into a viral vector) and transducing a host cell with the virus (or vector) or by transfection procedures known in the art, for introducing heterologous polynucleotides into mammalian cells, e.g., dextran-mediated transfection, calcium phosphate precipitation, polybrene mediated transfection, protoplast fusion, electroporation, encapsulation of the polynucleotide(s) into liposomes and direct microinjection of the DNA molecule. The transformation procedure used depends upon the host to be transformed. Methods for introduction of heterologous polynucleotides into mammalian cells are known in the art and include, but are not limited to, dextran-mediated transfection, calcium phosphate precipitation, polybrene mediated transfection, protoplast fusion, electroporation, particle bombardment, encapsulation of the polynucleotide(s) in liposomes, peptide conjugates, dendrimers, and direct microinjection of the DNA into nuclei.

In another aspect, the invention features, a host cell comprising a nucleic acid described herein. In embodiments the cell expresses an antibody molecule, or component thereof, described herein. Still further embodiment provides a method of producing an antibody molecule, e.g., an anti-GCC antibody molecule described herein, e.g. a rabbit antibody molecule, or a humanized version thereof, comprising maintaining the host cell under conditions appropriate for expression, whereby immunoglobulin chain(s) are expressed and an antibody molecule is produced. An additional embodiment provides a host cell comprising any of the foregoing expression vectors encoding heavy and light chain antibody sequences. The host cell can be a eukaryotic cell, e.g., a mammalian cell (e.g., a non-human mammalian host cell), an insect cell, a yeast cell, or a prokaryotic cell, e.g., *E. coli*. For example, the mammalian cell can be a cultured cell or a cell line. Exemplary mammalian cells include lymphocytic cell lines (e.g., NS0), Chinese hamster ovary cells (CHO), COS cells. In a particular embodiment, the cultured host cell is a CHO cell comprising nucleic acid sequences encoding a MIL-44-148-2 antibody molecule. In another embodiment, the host cell is Hybridoma MIL-44-148-2 (PTA-8132). Additionally cells include oocyte cells, and cells from a transgenic animal, e.g., mammary epithelial cell. For example, nucleic acids encoding an antibody molecule described herein can be expressed in a transgenic nonhuman animal.

Mammalian cell lines available as hosts for expression are known in the art and include many immortalized cell lines available from the American Type Culture Collection (ATCC), including but not limited to Chinese hamster ovary (CHO) cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. Site directed mutagenesis of the antibody CH2 domain to eliminate glycosylation may be preferred in order to prevent changes in either the immunogenicity, pharmacokinetic, and/or effector functions resulting from non-human glycosylation. The expression methods are selected by determining which system generates the highest expression levels and produce antibodies with constitutive GCC binding properties.

A still further embodiment provides a method of producing an anti-GCC antibody molecule, e.g., a rabbit antibody molecule or a humanized version thereof, comprising maintaining the host cell comprising nucleic acids described herein, e.g., one or more nucleic acid sequence listed in Table 4 or 6, under conditions appropriate for expression of an immunoglobulin, whereby immunoglobulin chains, are expressed and an antibody molecule, e.g., a rabbit antibody molecule, or a humanized version thereof, that binds GCC, or a fragment or variant thereof, is produced. For example, methods of expression of antibody molecules include the use of host cells wherein a first recombinant nucleic acid molecule encoding an antibody molecule, e.g., a rabbit antibody light chain or a humanized version thereof, and a second recombinant nucleic acid molecule encoding an antibody molecule, e.g., a rabbit antibody heavy chain or a humanized version thereof, are comprised in a single expression vector. In other embodiments, they are in separate vectors. The method can further comprise the step of isolating or recovering the antibody, antigen-binding fragment of an antibody, antibody chain or antigen-binding fragment of an antibody chain, if desired.

For example, a nucleic acid molecule (i.e., one or more nucleic acid molecules) encoding the heavy and light chains of a rabbit (or humanized) antibody that binds a GCC protein, or an expression construct (i.e., one or more constructs) comprising such nucleic acid molecule(s), can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g., in the presence of an inducer, in a suitable non-human animal, in suitable culture media supplemented with appropriate salts, growth factors, antibiotics, nutritional supplements, etc.), whereby the encoded polypeptide(s) are produced. If desired, the encoded protein can be isolated or recovered (e.g., from the animal, the host cell, medium, milk). This process encompasses expression in a host cell of a transgenic non-human animal (see, e.g., WO 92/03918, GenPharm International) or plant.

Further, expression of antibodies of the invention (or other moieties therefrom) from production cell lines can be enhanced using a number of known techniques. For example, the glutamine synthetase and DHFR gene expression systems are common approaches for enhancing expression under certain conditions. High expressing cell clones can be identified using conventional techniques, such as limited dilution cloning, Microdrop technology, or any other methods known in the art. The GS system is discussed in whole or part in connection with European Patent Nos. 0 216 846, 0 256 055, and 0 323 997 and European Patent Application No. 89303964.4.

In an exemplary system for recombinant expression of a modified antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Antibodies of the invention can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

The antibodies, antigen-binding fragments, antibody chains and antigen-binding portions thereof described herein also can be produced in a suitable in vitro expression system, by chemical synthesis or by any other suitable method.

Fusion Proteins and Immunoconjugates

The anti-GCC antibodies described herein can be functionally linked by any suitable method (e.g., chemical coupling, genetic fusion, noncovalent association or otherwise) to one or more non-antibody molecular entities.

Fusion proteins can be produced in which an anti-GCC antibody molecule as described herein and a non-antibody moiety are components of a single continuous polypeptide chain. The non-antibody moiety can be located N-terminally, C-terminally, or internally, with respect to the antibody moiety. For example, some embodiments can be produced by the insertion of a nucleic acid encoding immunoglobulin sequences into a suitable expression vector, such as a pET vector (e.g., pET-15b, Novagen), a phage vector (e.g., pCNA-TAB 5 E, Pharmacia), or other vector, e.g., pRIT2T Protein A fusion vector, Pharmacia). The resulting construct can be expressed to produce antibody chains that comprise a non-antibody moiety (e.g., Histidine tag, E tag, or Protein A IgG binding domain). Fusion proteins can be isolated or recovered using any suitable technique, such as chromatography using a suitable affinity matrix (see, e.g., *Current Protocols in Molecular Biology* (Ausubel, F. M et al., eds., Vol. 2, Suppl. 26, pp. 16.4.1-16.7.8 (1991)).

The invention provides anti-GCC antibody molecules which are directed to and, in embodiments, are internalized into cells. They are capable of delivering therapeutic agents or detectable agents to or into cells expressing GCC, but not to or into cells where the target is not expressed. Thus, the invention also provides anti-GCC immunoconjugates comprising an anti-GCC antibody molecule as described herein, which is conjugated to a therapeutic agent or a detectable agent. In embodiments, the affinity for GCC of an anti-GCC immunoconjugate is at least 10, 25, 50, 75, 80, 90, or 95% of that for the unconjugated antibody. This can be determined using cell surface GCC or isolated GCC. In an embodiment the anti-GCC antibody molecule, e.g., an immunoconjugate, has an LD50, as determined by an assay described herein, of less than 1,000, 500, 250, 100, or 50 pM.

The anti-GCC antibody molecule can be modified to act as an immunoconjugate utilizing techniques that are known in the art. See e.g., *Vitetta Immunol Today* 14:252 (1993). See also U.S. Pat. No. 5,194,594. The preparation of radiolabeled antibodies can also be readily prepared utilizing techniques that are known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (U.S. Re. Pat. No. 35,500), 5,648,471, and 5,697,902.

In some embodiments, the antibody molecule and non-antibody moiety are connected by means of a linker In such embodiments, the immunoconjugate is represented by formula (I):

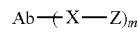

$$Ab\text{—}(X\text{—}Z)_m$$

wherein,

Ab is an anti-GCC antibody molecule described herein;

X is a moiety which connects Ab and Z, e.g., the residue of a linker described herein after covalent linkage to one or both of Ab and Z;

Z is a therapeutic agent or label; and m ranges from about 1 to about 15.

The variable m represents the number of —X—Z moieties per antibody molecule in an immunoconjugate of formula (I). In various embodiments, m ranges from 1 to 15, 1 to 10, 1 to 9, 1 to 8, 1 to 7, 1 to 6, 1 to 5, 1 to 4, 1 to 3, or 1 to 2. In some embodiments, m ranges from 2 to 10, 2 to 9, 2 to 8, 2 to 7, 2 to 6, 2 to 5, 2 to 4 or 2 to 3. In other embodiments, m is 1, 2, 3, 4, 5 or 6. In compositions comprising a plurality of immunoconjugates of formula (I), m is the average number of —X—Z moieties per Ab, also referred to as the average drug loading. Average drug loading may range from 1 to about 15-X—Z moieties per Ab. In some embodiments, when m represents the average drug loading, m is about 1, about 2, about 3, about 4, about 5, about 6, about 7, or about 8. In exemplary embodiments, m is from about 2 to about 8. In one embodiment, m is about 8. In another embodiment, m is about 4. In another embodiment, m is about 2.

The average number of —X—Z moieties per Ab may be characterized by conventional means such as mass spectroscopy, ELISA assay, and HPLC. The quantitative distribution of immunoconjugates in terms of m may also be determined. In some instances, separation, purification, and characterization of homogeneous immunoconjugates where m is a certain value, as distinguished from immunoconjugates with other drug loadings, may be achieved by means such as reverse phase HPLC or electrophoresis.

The immunoconjugates of formula (I) may exist as mixtures, wherein each component of the mixture has a different m value. For example, an immunoconjugate of formula (I) may exist as a mixture of two separate immunoconjugate components: one immunoconjugate component wherein m is 7, and the other immunoconjugate component wherein m is 8.

In one embodiment, the immunoconjugate of formula (I) exists as a mixture of three separate immunoconjugates wherein m for the three separate immunoconjugates is 1, 2, and 3, respectively; 3, 4, and 5, respectively; 5, 6, and 7, respectively; 7, 8, and 9, respectively; 9, 10, and 11, respectively; 11, 12, and 13, respectively; or 13, 14, and 15, respectively.

A variety of suitable linkers (e.g., heterobifunctional reagents for connecting an antibody molecule to a therapeutic agent or label) and methods for preparing immunoconjugates are known in the art. (See, for example, Chari et al., Cancer Research 52:127-131 (1992).) The linker can be cleavable, e.g., under physiological conditions, e.g., under intracellular conditions, such that cleavage of the linker releases the drug (i.e., therapeutic agent or label) in the intracellular environment. In other embodiments, the linker is not cleavable, and the drug is released, for example, by antibody degradation.

The linker can be bonded to a chemically reactive group on the antibody moiety, e.g., to a free amino, imino, hydroxyl, thiol or carboxyl group (e.g., to the N- or C-terminus, to the epsilon amino group of one or more lysine residues, the free carboxylic acid group of one or more glutamic acid or aspartic acid residues, or to the sulfhydryl group of one or more cysteinyl residues). The site to which the linker is bound can be a natural residue in the amino acid sequence of the antibody moiety or it can be introduced into the antibody moiety, e.g., by DNA recombinant technology (e.g., by introducing a cysteine or protease cleavage site in the amino acid sequence) or by protein biochemistry (e.g., reduction, pH adjustment or proteolysis).

One of the most commonly used non-specific methods of covalent attachment is the carbodiimide reaction to link a carboxy (or amino) group of a compound to amino (or carboxy) groups of the antibody molecule. Additionally, bifunctional agents such as dialdehydes or imidoesters have been used to link the amino group of a compound to amino groups of an antibody molecule. Also available for attachment of drug (i.e., therapeutic agent or label) to antibody molecules is the Schiff base reaction. This method involves the periodate oxidation of a drug that contains glycol or hydroxy groups, thus forming an aldehyde which is then reacted with the antibody molecule. Attachment occurs via formation of a Schiff base with amino groups of the antibody molecule. Isothiocyanates can also be used as coupling agents for covalently attaching drugs to antibody molecule. Other techniques are known to the skilled artisan and within the scope of the present invention.

In certain embodiments, an intermediate, which is the precursor of the linker (X), is reacted with the drug (Z) under appropriate conditions. In certain embodiments, reactive groups are used on the drug and/or the intermediate. The product of the reaction between the drug (i.e., therapeutic agent or label) and the intermediate, or the derivatized drug, is subsequently reacted with the antibody molecule under appropriate conditions.

The immunoconjugate can be purified from reactants by employing methodologies well known to those of skill in the art, e.g., column chromatography (e.g., affinity chromatography, ion exchange chromatography, gel filtration, hydrophobic interaction chromatography), dialysis, diafiltration or precipitation. The immunoconjugate can be evaluated by employing methodologies well known to those skilled in the art, e.g., SDS-PAGE, mass spectroscopy, or capillary electrophoresis.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug (i.e., therapeutic agent or label) inside target cells (see, e.g., Dubowchik and Walker, 1999, Pharm. Therapeutics 83:67-123). Most typical are peptidyl linkers that are cleavable by enzymes that are present in GCC-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO:319)). Other examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the drug (i.e., therapeutic agent or label) is that the drug is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg Med. Chem. 3(10):1299-1304), or a 3'-N-amide analog (Lau et al., 1995, Bioorg-Med-Chem. 3(10):1305-12).

In yet other embodiments, the linker unit is not cleavable and the drug (i.e., therapeutic agent or label) is released by antibody degradation. (See for example U.S. Publication No. 20050238649 incorporated by reference herein in its entirety and for all purposes).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of immunoconjugate, are cleaved when the immunoconjugate presents in an extracellular environment (e.g., in plasma). Whether a linker is not substantially sensitive to the extracellular environment can be determined, for example, by incubating with plasma the immunoconjugate for a predetermined time period (e.g., 2, 4, 8, 16, or 24 hours) and then quantifying the amount of free drug present in the plasma.

In other, non-mutually exclusive embodiments, the linker promotes cellular internalization. In certain embodiments, the linker promotes cellular internalization when conjugated to the therapeutic agent or label (Z). In yet other embodiments, the linker promotes cellular internalization when conjugated to both the Z moiety and the anti-GCC antibody molecule.

A variety of exemplary linkers that can be used with the present compositions and methods are described in WO 2004-010957, U.S. Publication No. 20060074008, U.S. Publication No. 20050238649, and U.S. Publication No. 20060024317 (each of which is incorporated by reference herein in its entirety and for all purposes).

Examples of linkers capable of being used to couple an antibody molecule to a therapeutic agent or label include, for example, maleimidocaproyl (mc); maleimidocaproyl-p-aminobenzylcarbamate; maleimidocaproyl-peptide-aminobenzylcarbamate linkers, e.g., maleimidocaproyl-L-phenylalanine-L-lysine-p-aminobenzylcarbamate and maleimidocaproyl-L-valine-L-citrulline-p-aminobenzylcarbamate (vc); N-succinimidyl 3-(2-pyridyldithio)proprionate (also known as N-succinimidyl 4-(2-pyridyldithio)pentanoate or SPP); 4-succinimidyl-oxycarbonyl-2-methyl-2-(2-pyridyldithio)-toluene (SMPT); N-succinimidyl 3-(2-pyridyldithio)propionate (SPDP); N-succinimidyl 4-(2-pyridyldithio)butyrate (SPDB); 2-iminothiolane; S-acetylsuccinic anhydride; disulfide benzyl carbamate; carbonate; hydrazone linkers; N-(α-Maleimidoacetoxy) succinimide ester; N-[4-(p-Azidosalicylamido) butyl]-3'-(2'-pyridyldithio)propionamide (AMAS); N-[β-Maleimidopropyloxy]succinimide ester (BMPS); [N-ε-Maleimidocaproyloxy]succinimide ester (EMCS); N-[γ-Maleimidobutyryloxy]succinimide ester (GMBS); Succinimidyl-4-[N-Maleimidomethyl]cyclohexane-1-carboxy-[6-amidocaproate](LC-SMCC); Succinimidyl 6-(3-[2-pyridyldithio]-propionamido)hexanoate (LC-SPDP); m-Maleimidobenzoyl-N-hydroxysuccinimide ester (MBS); N-Succinimidyl[4-iodoacetyl]aminobenzoate (SIAB); Succinimidyl 4-[N-maleimidomethyl]cyclohexane-1-carboxylate (SMCC); N-Succinimidyl 3-[2-pyridyldithio]-propionamido (SPDP); [N-εΩ-Maleimidocaproyloxy] sulfosuccinimide ester (Sulfo-EMCS); N-[γ-Maleimidobutyryloxy]sulfosuccinimide ester (Sulfo-GMBS); 4-Sulfosuccinimidyl-6-methyl-α-(2-pyridyldithio)toluamido]hexanoate) (Sulfo-LC-SMPT); Sulfosuccinimidyl 6-(3'-[2-pyridyldithio]-propionamido) hexanoate (Sulfo-LC-SPDP); m-Maleimidobenzoyl-N-hydroxysulfosuccinimide ester (Sulfo-MBS); N-Sulfosuccinimidyl[4-iodoacetyl]aminobenzoate (Sulfo-SIAB); Sulfosuccinimidyl 4-[N-maleimidomethyl]cyclohexane-1-carboxylate (Sulfo-SMCC); Sulfosuccinimidyl 4-[p-maleimidophenyl]butyrate (Sulfo-SMPB); ethylene glycol-bis (succinic acid N-hydroxysuccinimide ester) (EGS); disuccinimidyl tartrate (DST); 1,4,7,10-tetraazacyclododecane-1,4,7,10-tetraacetic acid (DOTA); diethylenetriaminepentaacetic acid (DTPA); and thiourea linkers.

In some embodiments, the therapeutic agent is a cytostatic or cytotoxic agent. Examples include, without limitation, antimetabolites (e.g., azathioprine, 6-mercaptopurine, 6-thioguanine, fludarabine, pentostatin, cladribine, 5-fluorouracil (5FU), floxuridine (FUDR), cytosine arabinoside (cytarabine), methotrexate, trimethoprim, pyrimethamine, pemetrexed); alkylating agents (e.g., cyclophosphamide, mechlorethamine, uramustine, melphalan, chlorambucil, thiotepa/chlorambucil, ifosfamide, carmustine, lomustine, streptozocin, busulfan, dibromomannitol, cisplatin, carboplatin, nedaplatin, oxaliplatin, satraplatin, triplatin tetranitrate, procarbazine, altretamine, dacarbazine, mitozolomide, temozolomide); anthracyclines (e.g., daunorubicin, doxorubicin, epirubicin, idarubicin, valrubicin); antibiotics (e.g., dactinomycin, bleomycin, mithramycin, anthramycin, streptozotocin, gramicidin D. mitomycins (e.g., mitomycin C), duocarmycins (e.g., CC-1065), calicheamicins); antimitotic agents (including, e.g., maytansinoids, auristatins, dolastatins, cryptophycins, vinca alkaloids (e.g., vincristine, vinblastine, vindesine, vinorelbine), taxanes (e.g., paclitaxel, docetaxel, or a novel taxane (see, e.g., International Patent Publication No. WO 01/38318, published May 31, 2001)), and colchicines; topoisomerase inhibitors (e.g., irinotecan, topotecan, amsacrine, etoposide, teniposide, mitoxantrone); and proteasome inhibitors (e.g., peptidyl boronic acids).

In some embodiments, the therapeutic agent is a maytansinoid. Maytansinoid compounds and methods for their conjugation to antibodies are described, for example, in Chari et al., *Cancer Res.*, 52: 127-131 (1992); Widdison et al., *J. Med. Chem.* 49: 4392-4408 (2006); and U.S. Pat. Nos. 5,208,020 and 6,333,410. Examples of maytansinoids include maytansine analogues having a modified aromatic ring (e.g., C-19-dechloro, C-20-demethoxy, C-20-acyloxy) and those having modifications at other positions (e.g., C-9-CH, C-14-alkoxymethyl, C-14-hydroxymethyl or acyloxymethyl, C-15-hydroxy/acyloxy, C-15-methoxy, C-18-N-demethyl, 4,5-deoxy). In certain embodiments, the maytansinoid is N.sup.2'-deacetyl-N.sup.2'-(4-mercapto-1-oxopentyl)maytansine (DM3), N.sup.2'-deacetyl-N.sup.2'-(3-mercapto-1-oxopropyl)-maytansine (DM1), or N.sup.2'-deacetyl-N.sup.2'-(4-mercapto-4-methyl-1-oxopentyl)maytansine (DM4).

Maytansinoid compounds that comprise a sulfhydryl group can be coupled to antibodies using a heterobifunctional linker that is connected to the maytansinoid compound by way of a thioether or disulfide linkage. In some such embodiments, the linker is coupled to an amino group on the antibody (e.g., a terminal amino group or the epsilon amino group of a lysine residue. In some embodiments, the heterobifunctional linker that is used to couple a maytansinoid compounds to an antibody is N-succinimidyl 3-(2-pyridyldithio)proprionate (also known as N-succinimidyl 4-(2-pyridyldithio)pentanoate, or SPP), 4-succinimidyl-oxycarbonyl-2-methyl-2-(2-pyridyldithio)-toluene (SMPT), N-succinimidyl 4[N-maleimidomethyl]cyclohexane-1-carboxylate (SMCC), N-succinimidyl 3-(2-pyridyldithio)propionate (SPDP); N-succinimidyl 4-(2-pyridyldithio)butyrate (SPDB), 2-iminothiolane, or S-acetylsuccinic anhydride.

In some other embodiments the therapeutic agent is a dolastatin. In some embodiments, the therapeutic agent is an auristatin, such as auristatin E (also known in the art as a derivative of dolastatin-10) or a derivative thereof. Auristatin compounds and methods for their conjugation to antibodies are described, for example, in Doronina et al., *Nature Biotech.*, 21: 778-784 (2003); Hamblett et al, *Clin. Cancer Res.*, 10: 7063-7070 (2004); Carter and Senter, *Cancer J.*, 14 154-169 (2008); U.S. Pat. Nos. 7,498,298, 7,091,186, 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414; U.S. Patent Publication Nos. 20090010945, 20060074008, 20080300192, 20050009751, 20050238649, and 20030083236; and International Patent Publication Nos. WO 04/010957 and WO 02/088172, each of which is incorporated by reference herein in its entirety and for all purposes.

The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include auristatin phenylalanine phenylenediamine (AFP), monomethyl auristatin E (MMAE), and monomethyl auristatin F (MMAF)

Anti-GCC Antibody Sequences

Rabbit monoclonal anti-GCC antibodies were generated by several methods, as is discussed in more detail in the Examples. Briefly, rabbit monoclonal antibodies MIL-44-148-2 and MIL-44-67-4 were generated by traditional immunization technology in rabbits. True rabbit-rabbit hybridomas were generated at Epitomics (Burlingame, Calif.) by fusing isolated B-cells from an immunized rabbit with Epitomics' proprietary fusion partner cell line (see U.S. Pat. Nos. 7,402,409; 7,429,487; 7,462,697; 7,575,896; 7,732,168; and 8,062,867). Specificity of the antibodies against GCC was tested by ELISA and flow cytometry (FCM).

Table 1 below summarizes the rabbit monoclonal anti-GCC antibodies of the invention generated using the hGCC (ECD)/mIgG2a FcR-mutII immunogen.

The sequences of the light and heavy chain variable regions were determined Table 2 below is a summary of the SEQ ID NOs for the variable regions of several antibodies. The amino acid and nucleic acid sequences for the variable regions of each of the heavy and light chains for rabbit anti-GCC antibodies are shown in Tables 3 and 4, respectively.

The amino acid and nucleic acid sequences for each of the CDRs of the heavy and light chains for anti-GCC antibodies are shown in Tables 5 and 6, respectively.

Sequencing of the CDRs allowed determination of the abundance of residues that might serve as toxin conjugation sites. For example, an unpaired free cysteine in the antigen binding region could be a site for auristatin conjugation and a lysine could be a site for maytansine conjugation. Toxin conjugation to an amino acid of the CDR would raise the concern of altering the binding affinity of the antibody to GCC. Thus, in embodiments the CDRs lack an amino acid which can be conjugated to a therapeutic agent.

TABLE 1

Summary of SEQ ID NOs for heavy and light chains of anti-GCC rabbit mAbs

| mAb | IgG Chain | Nucleic Acid SEQ ID NO | Amino Acid SEQ ID NO |
| --- | --- | --- | --- |
| MIL-44-148-2 H2 | Heavy | 4 | 42 |
| MIL-44-148-2 L5 | Light | 5 | 43 |
| MIL-44-67-4 H2 | Heavy | 6 | 44 |
| MIL-44-67-4 L4 | Light | 7 | 45 |

```
MIL-44-148-2 H2 Nucleic Acid                                      (SEQ ID NO: 4)
ATGGAGACTGGGCTGCGCTGGCTTCTCCTGGTCGCTGTGCTCAAAGGTGTCCAGTGTCAGTCAGTGAAGGAGTCCGG

GGGAGGCCTCTTCAAGCCAACGGATACCCTGACACTCACCTGCACCGTCTCTGGATTCTCCCTCAGTAGTCATAGAA

TGAACTGGGTCCGCCAGACTCCAGGGAAGGGGCTGGAATGGATCGCAATCATTACTCATAATAGTATCACATACTAC

GCGAGCTGGGCGAAAAGCCGATCCACCATCACCAGAAACACCAGCGAGAACACGGTGACTCTGAAAATGACCAGTCT

GACAGCCGCGGACACGGCCACTTATTTCTGTGCCAGAGAGGATAGTATGGGGTATTATTTTGACTTGTGGGGCCCAG

GCACCCTGGTCACCATCTCCTCA

GGGCAACCTAAGGCTCCATCAGTCTTCCCACTGGCCCCCTGCTGCGGGACACACCCAGCTCCACGGTGACCCTGGG

CTGCCTGGTCAAAGGGTACCTCCCGGAGCCAGTGACCGTGACCTGGAACTCGGGCACCCTCACCAATGGGGTACGCA

CCTTCCCGTCCGTCCGGCAGTCCTCAGGCCTCTACTCGCTGAGCAGCGTGGTGAGCGTGACCTCAAGCAGCCAGCCC

GTCACCTGCAACGTGGCCCACCCAGCCACCAACACCAAAGTGGACAAGACCGTTGCGCCCTCGACATGCAGCAAGCC

CACGTGCCCACCCCTGAACTCCTGGGGGGACCGTCTGTCTTCATCTTCCCCCCAAAACCCAAGGACACCCTCATGA

TCTCACGCACCCCCGAGGTCACATGCGTGGTGGTGGACGTGAGCCAGGATGACCCCGAGGTGCAGTTCACATGGTAC

ATAAACAACGAGCAGGTGCGCACCGCCCGGCCGCCGCTACGGGAGCAGCAGTTCAACAGCACGATCCGCGTGGTCAG

CACCCTCCCCATCGCGCACCAGGACTGGCTGAGGGGCAAGGAGTTCAAGTGCAAAGTCCACAACAAGGCACTCCCGG

CCCCCATCGAGAAACCATCTCCAAAGCCAGAGGGCAGCCCCTGGAGCCGAAGGTCTACACCATGGGCCCTCCCCGG

GAGGAGCTGAGCAGCAGGTCGGTCAGCCTGACCTGCATGATCAACGGCTTCTACCCTTCCGACATCTCGGTGGAGTG

GGAGAAGAACGGGAAGGCAGAGGACAACTACAAGACCACGCCGGCCGTGCTGGACAGCGACGGCTCCTACTTCCTCT
```

-continued

ACAGCAAGCTCTCAGTGCCCACGAGTGAGTGGCAGCGGGGCGACGTCTTCACCTGCTCCGTGATGCACGAGGCCTTG

CACAACCACTACACGCAGAAGTCCATCTCCCGCTCTCCGGGTAAATGA

MIL-44-148-2 H2 Amino Acid                                            (SEQ ID NO: 42)
METGLRWLLLVAVLKGVQCQSVKESGGGLFKPTDTLTLTCTVSGFSLSSHRMNWVRQTPGKGLEWIAIITHNSITYY

ASWAKSRSTITRNTSENTVTLKMTSLTAADTATYFCAREDSMGYYFDLWGPGTLVTISSGQPKAPSVFPLAPCCGDT

PSSTVTLGCLVKGYLPEPVTVTWNSGTLTNGVRTFPSVRQSSGLYSLSSVVSVTSSSQPVTCNVAHPATNTKVDKTV

APSTCSKPTCPPPELLGGPSVFIFPPKPKDTLMISRTPEVTCVVVDVSQDDPEVQFTWYINNEQVRTARPPLREQQF

NSTIRVVSTLPIAHQDWLRGKEFKCKVHNKALPAPIEKTISKARGQPLEPKVYTMGPPREELSSRSVSLTCMINGFY

PSDISVEWEKNGKAEDNYKTTPAVLDSDGSYFLYSKLSVPTSEWQRGDVFTCSVMHEALHNHYTQKSISRSPGK

MIL-44-148-2 L5 Nucleic Acid                                          (SEQ ID NO: 5)
ATGGACACGAGGGCCCCCACTCAGCTGCTGGGCTCCTGCTGCTCTGGCTCCCAGGTGCCAGATGTGCCTATGATAT

GACCCAGACTCCAGCCTCTGTGGAGGTAGCTGTGGGAGGCACAGTCACCATCAAGTGCCAGGCCAGTCAGAGCATTA

GTAACTGGTTAGCCTGGTATCAGCAGAAACCAGGGCAGTCTCCCAAGCCCCTGATCTACAGGGCATCCACTCTGGCA

TCTGGGGTCTCATCGCGGTTCAGAGGCAGTGGATCTGGGACACAGTTCACTCTCACCATCAGTGGCGTGGAGTGTGC

CGATGCTGCCACTTACTACTGTCAGCAGACTTATACTAATAATCATCTTGATAATGGTTTCGGCGGAGGGACCGAGG

TGGTGGTCAAA

GGTGATCCAGTTGCACCTACTGTCCTCATCTTCCCACCAGCTGCTGATCAGGTGGCAACTGGAACAGTCACCATCGT

GTGTGTGGCGAATAAATACTTTCCCGATGTCACCGTCACCTGGGAGGTGGATGGCACCACCCAAACAACTGGCATCG

AGAACAGTAAAACACCGCAGAATTCTGCAGATTGTACCTACAACCTCAGCAGCACTCTGACACTGACCAGCACACAG

TACAACAGCCACAAAGAGTACACCTGCAGGGTGACCCAGGGCACGACCTCAGTCGTCCAGAGCTTCAATAGGGGTGA

CTGTTAG

MIL-44-148-2 L5 Amino Acid                                            (SEQ ID NO: 43)
MDTRAPTQLLGLLLLWLPGARCAYDMTQTPASVEVAVGGTVTIKCQASQSISNWLAWYQQKPGQSPKPLIYRASTLA

SGVSSRFRGSGSGTQFTLTISGVECADAATYYCQQTYTNNHLDNGFGGGTEVVVKGDPVAPTVLIFPPAADQVATGT

VTIVCVANKYFPDVTVTWEVDGTTQTTGIENSKTPQNSADCTYNLSSTLTLTSTQYNSHKEYTCRVTQGTTSVVQSF

NRGDC

MIL-44-67-4 H2 Nucleic Acid                                           (SEQ ID NO: 6)
ATGGAGACTGGGCTGCGCTGGCTTCTCCTGGTCGCTGTGCTCAAAGGTGTCCAGTGTCAGTCGGTGGAGGAGTCCGG

GGGTCGCCTGGTCACGCCTGGGACACCCCTGACACTCACCTGCACAGCCTCTGGATCCGACATCAGTAACTATGCAA

TATCCTGGGTCCGCCAGGCTCCAGGGAAGGGGCTGGAATTCATCGGATATATTAGTTATGGTAAAAGTATATACTAC

GCGAGCTGGGCGAAAGGCCGGTTCGCCATCTCCAAAACCTCGTCGACCACGGTGGATCTGGAAATCACCAGTCCGAC

AACCGAGGACACGGCCACCTATTTTTGTGCCAGAGAGGATAGTGCTACTTATAGTCCTAACTTGTGGGGCCCAGGCA

CCCTGGTCACCGTCTCCTCA

GGGCAACCTAAGGCTCCATCAGTCTTCCCACTGGCCCCCTGCTGCGGGGACACACCCAGCTCCACGGTGACCCTGGG

CTGCCTGGTCAAAGGGTACCTCCCGGAGCCAGTGACCGTGACCTGGAACTCGGGCACCCTCACCAATGGGGTACGCA

CCTTCCCGTCCGTCCGGCAGTCCTCAGGCCTCTACTCGCTGAGCAGCGTGGTGAGCGTGACCTCAAGCAGCCAGCCC

-continued

```
GTCACCTGCAACGTGGCCCACCCAGCCACCAACACCAAAGTGGACAAGACCGTTGCGCCCTCGACATGCAGCAAGCC

CACGTGCCCACCCCCTGAACTCCTGGGGGACCGTCTGTCTTCATCTTCCCCCCAAAACCCAAGGACACCCTCATGA

TCTCACGCACCCCCGAGGTCACATGCGTGGTGGTGGACGTGAGCCAGGATGACCCCGAGGTGCAGTTCACATGGTAC

ATAAACAACGAGCAGGTGCGCACCGCCCGGCCGCCGCTACGGGAGCAGCAGTTCAACAGCACGATCCGCGTGGTCAG

CACCCTCCCCATCGCGCACCAGGACTGGCTGAGGGGCAAGGAGTTCAAGTGCAAAGTCCACAACAAGGCACTCCCGG

CCCCCATCGAGAAAACCATCTCCAAAGCCAGAGGGCAGCCCCTGGAGCCGAAGGTCTACACCATGGGCCCTCCCCGG

GAGGAGCTGAGCAGCAGGTCGGTCAGCCTGACCTGCATGATCAACGGCTTCTACCCTTCCGACATCTCGGTGGAGTG

GGAGAAGAACGGGAAGGCAGAGGACAACTACAAGACCACGCCGGCCGTGCTGGACAGCGACGGCTCCTACTTCCTCT

ACAGCAAGCTCTCAGTGCCCACGAGTGAGTGGCAGCGGGGCGACGTCTTCACCTGCTCCGTGATGCACGAGGCCTTG

CACAACCACTACACGCAGAAGTCCATCTCCCGCTCTCCGGGTAAATGA

MIL-44-67-4 H2 Amino Acid                                  (SEQ ID NO: 44)
METGLRWLLLVAVLKGVQCQSVEESGGRLVTPGTPLTLTCTASGSDISNYAISWVRQAPGKGLEFIGYISYGKSIYY

ASWAKGRFAISKTSSTTVDLEITSPTTEDTATYFCAREDSATYSPNLWGPGTLVTVSSGQPKAPSVFPLAPCCGDTP

SSTVTLGCLVKGYLPEPVTVTWNSGTLTNGVRTFPSVRQSSGLYSLSSVVSVTSSSQPVTCNVAHPATNTKVDKTVA

PSTCSKPTCPPPELLGGPSVFIFPPKPKDTLMISRTPEVTCVVVDVSQDDPEVQFTWYINNEQVRTARPPLREQQFN

STIRVVSTLPIAHQDWLRGKEFKCKVHNKALPAPIEKTISKARGQPLEPKVYTMGPPREELSSRSVSLTCMINGFYP

SDISVEWEKNGKAEDNYKTTPAVLDSDGSYFLYSKLSVPTSEWQRGDVFTCSVMHEALHNHYTQKSISRSPGK

MIL-44-67-4 L4 Nucleic acid                                (SEQ ID NO: 7)
ATGGACACGAGGGCCCCCACTCAGCTGCTGGGGCTCCTGCTGCTCTGGCTCCCAGGTGCCAGATGTGCCTATGATAT

GACCCAGACTCCAGCCTCTGTGGAGGTAGCTGTGGGAGGCACAGTCACCATCAAGTGCCAGGCCAGTCAGAGTATTA

ACACCTACTTAGCCTGGTATCAGCAGAAACCAGGGCAGCGTCCCAAGCTCCTGATCTACAGGGCATCCACTCTGGCA

TCTGGGGTCTCATCGCGGTTCAAAGGCAGTGGATCTGGGACAGAGTTCACTCTCACCATCAGCGGCGTGGAGTGTGC

CGATGCTGCCACTTACTACTGTCAACAGGGTTATAGTTATAATAATCTTGATCGTGCTTTCGGCGGAGGGACCGAGG

TGGTGGTCACA

GGTGATCCAGTTGCACCTACTGTCCTCATCTTCCCACCAGCTGCTGATCAGGTGGCAACTGGAACAGTCACCATCGT

GTGTGTGGCGAATAAATACTTTCCCGATGTCACCGTCACCTGGGAGGTGGATGGCACCACCCAAACAACTGGCATCG

AGAACAGTAAAACACCGCAGAATTCTGCAGATTGTACCTACAACCTCAGCAGCACTCTGACACTGACCAGCACACAG

TACAACAGCCACAAAGAGTACACCTGCAAGGTGACCCAGGGCACGACCTCAGTCGTCCAGAGCTTCAATAGGGGTGA

CTGTTAG

MIL-44-67-4 L4 Amino acid                                  (SEQ ID NO: 45)
MDTRAPTQLLGLLLLWLPGARCAYDMTQTPASVEVAVGGTVTIKCQASQSINTYLAWYQQKPGQRPKLLIYRASTLA

SGVSSRFKGSGSGTEFTLTISGVECADAATYYCQQGYSYNNLDRAFGGGTEVVVTGDPVAPTVLIFPPAADQVATGT

VTIVCVANKYFPDVTVTWEVDGTTQTTGIENSKTPQNSADCTYNLSSTLTLTSTQYNSHKEYTCKVTQGTTSVVQSF

NRGDC
```

TABLE 2

Summary of SEQ ID NOs for variable regions of anti-GCC rabbit mAbs

| mAb | IgG Chain | Nucleic Acid SEQ ID NO | Amino Acid SEQ ID NO |
|---|---|---|---|
| MIL-44-148-2 H2 | Heavy | 10 | 11 |
| MIL-44-148-2 L5 | Light | 12 | 13 |
| MIL-44-67-4 H2 | Heavy | 14 | 15 |
| MIL-44-67-4 L4 | Light | 16 | 17 |

TABLE 3

Amino Acid Sequences of mAb variable regions of anti-GCC rabbit mAbs

| mAb | IgG Chain | SEQ ID NO: | Nucleic Acid Sequence |
|---|---|---|---|
| MIL-44-148-2 | Heavy | 11 | QSVEESGGGLFKPTDTLTLTCTVSGFSLSSHRMNWVRQTPGKGLEWIA IITHNSITYYASWAKSRSTITRNTSENTVTLKMTSLTAADTATYFCAR EDSMGYYFDLWGPGTLVTISS |
| MIL-44-148-2 | Light | 13 | AYDMTQTPASVEVAVGGTVTIKCQASQSISNWLAWYQQ KPGQSPKPLIYRASTLASGVSSRFRGSGSGTQFTLTISGVECADAATYYC QQTYTNNHLDNGFGGGTEVVVK |
| MIL-44-67-4 | Heavy | 15 | QSVEESGGRLVTPGTPLTLTCTASGSDISNYAISWVRQAPG KGLEFIGYISYGKSIYYASWAKGRFAISKTSSTTVDLEITSPTTEDTATYFCAR EDSATYSPNLWGPGTLVTVSS |
| MIL-44-67-4 | Light | 17 | AYDMTQTPASVEVAVGGTVTIKCQASQSINTYLAWYQQ KPGQRPKLLIYRASTLASGVSSRFKGSGSGTEFTLTISGVECADAATYYC QQGYSYNNLDRAFGGGTEVVVT |

TABLE 4

Nucleic Acid Sequences of mAb variable regions of anti-GCC rabbit mAbs

| mAb | IgG Chain | SEQ ID NO: | Nucleic Acid Sequence |
|---|---|---|---|
| MIL-44-148-2 | Heavy | 10 | CAGTCAGTGAAGGAGTCCGGGGGAGGCCTCTTCAAGCCAACGGATACCCTGACACT CACCTGCACCGTCTCTGGATTCTCCCTCAGTAGTCATAGAATGAACTGGGTCCGCC AGACTCCAGGGAAGGGGCTGGAATGGATCGCAATCATTACTCATAATAGTATCACA TACTACGCGAGCTGGGCGAAAAGCCGATCCACCATCACCAGAAACACCAGCGAGAA CACGGTGACTCTGAAAATGACCAGTCTGACAGCCGCGGACACGGCCACTTATTTCT GTGCCAGAGAGGATAGTATGGGGTATTATTTTGACTTGTGGGGCCCAGGCACCCTG GTCACCATCTCCTCA |
| MIL-44-148-2 | Light | 12 | GCCTATGATATGACCCAGACTCCAGCCTCTGTGGAGGTAGCTGTGGGAGGCACAGT CACCATCAAGTGCCAGGCCAGTCAGAGCATTAGTAACTGGTTAGCCTGGTATCAGC AGAAACCAGGGCAGTCTCCCAAGCCCCTGATCTACAGGGCATCCACTCTCGGCATCT GGGGTCTCATCGCGGTTCAGAGGCAGTGGATCTGGGACACAGTTCACTCTCACCAT CAGTGGCGTGGAGTGTGCCGATGCTGCCACTTACTACTGTCAGCAGACTTATACTA ATAATCATCTTGATAATGGTTTCGGCGGAGGGACCGAGGTGGTGGTCAAA |
| MIL-44-67-4 | Heavy | 14 | CAGTCGGTGGAGGAGTCCGGGGGTCGCCTGGTCACGCCTGGGACACCCCTGACACT CACCTGCACAGCCTCTGGATCCGACATCAGTAACTATGCCAATATCCTGGGTCCGCC AGGCTCCAGGGAAGGGGCTGGAATTCATCGGATATATTAGTTATGGTAAAAGTATA TACTACGCGAGCTGGGCGAAAGGCCGGTTCGCCATCTCCAAAACCTCGTCGACCAC GGTGGATCTGGAAATCACCAGTCCGACAACCGAGGACACGGCCACCTATTTTTGTG CCAGAGAGGATAGTGCTACTTATAGTCCTAACTTGTGGGGCCCAGGCACCCTGGCT ACCGTCTCCTCA |
| MIL-44-67-4 | Light | 16 | GCCTATGATATGACCCAGACTCCAGCCTCTGTGGAGGTAGCTGTGGGAGGCACAGT CACCATCAAGTGCCAGGCCAGTCAGAGTATTAACACCTACTTAGCCTGGTATCAGC AGAAACCAGGGCAGCGTCGCAAGCTCCTGATCTACAGGGCATCCACTCTGGCATCT GGGGTGTCATCGCGGTTCAAAGGCAGTGGATCTGCGACAGAGTTCACTCTCACCAT CAGCGGCGTGGAGTGTGCCGATGCTGCCACTTACTACTGTCAACAGGGTTATAGTT ATAATAATCTTGATCGTCTTTCGGCGGAGGGACCGAGGTGGTGGTCACA |

TABLE 5

Amino Acid Sequences of CDRs of anti-GCC rabbit mAbs

| mAb | IgG | SEQ ID NO: | Amino Acid Sequence |
|---|---|---|---|
| MIL-44-148-2-H2 | VH CDR1 | 21 | SHRMN |
| MIL-44-148-2-H2 | VH CDR2 | 22 | IITHNSITYYASWAKS |
| MIL-44-148-2-H2 | VH CDR3 | 23 | EDSMGYYFDL |
| MIL-44-148-2-L5 | VK CDR1 | 27 | QASQSISNWLA |
| MIL-44-148-2-L5 | VK CDR2 | 28 | RASTLAS |
| MIL-44-148-2-L5 | VK CDR3 | 29 | QQTYTNNHLDNG |

TABLE 5-continued

Amino Acid Sequences of CDRs of anti-GCC rabbit mAbs

| mAb | IgG | SEQ ID NO: | Amino Acid Sequence |
|---|---|---|---|
| MIL-44-67-4 H2 | VH CDR1 | 33 | NYAIS |
| MIL-44-67-4 H2 | VH CDR2 | 34 | YISYGKSIYYASWAKG |
| MIL-44-67-4 H2 | VH CDR3 | 35 | EDSATYSPNL |
| MIL-44-67-4 L4 | VK CDR1 | 39 | QASQSINTYLA |
| MIL-44-67-4 L4 | VK CDR2 | 40 | RASTLAS |
| MIL-44-67-4 L4 | VK CDR3 | 41 | QQGYSYNNLDRA |

TABLE 6

Nucleic Acid Sequences of CDRs of anti-GCC rabbit mAbs

| mAb | IgG | SEQ ID NO: | Nucleic Acid Sequence |
|---|---|---|---|
| MIL-44-148-2-H2 | VH CDR1 | 18 | AGTCATAGAATGAAC |
| MIL-44-148-2-H2 | VH CDR2 | 19 | ATCATTACTCATAATAGTATCACA TACTACGCGAGCTGGGCGAAAAGC |
| MIL-44-148-2-H2 | VH CDR3 | 20 | GAGGATAGTATGGGGTATTAT TTTGACTTG |
| MIL-44-148-2-L5 | VK CDR1 | 24 | CAGGCCAGTCAGAGCATTAGTA ACTGGTTAGCC |
| MIL-44-148-2-L5 | VK CDR2 | 25 | AGGGCATCCACTCTGGCATCT |
| MIL-44-148-2-L5 | VK CDR3 | 26 | CAGCAGACTTATACTAATAATCA TCTTGATAATGGT |
| MIL-44-67-4 H2 | VH CDR1 | 30 | AACTATGCAATATCC |
| MFL-44-67-4 H2 | VH CDR2 | 31 | TATATTAGTTATGGTAAAAGTATAT ACTACGCGAGCTGGGCGAAAGGC |
| MIL-44-67-4 H2 | VH CDR3 | 32 | AGTCCTAACTTG |
| MIL-44-67-4 L4 | VK CDR1 | 36 | CAGGCCAGTCAGAGTATTA ACACCTACTTAGCC |
| MIL-44-67-4 L4 | VK CDR2 | 37 | AGGGCATCCACTCTGGCATCT |
| MIL-44-67-4 L4 | VK CDR3 | 38 | CAACAGGGTTATAGTTATA ATAATCTTGATCGTGCT |

Uses

The rabbit monoclonal anti-GCC antibody molecules described herein have in vitro and in vivo diagnostic, prognostic, imaging, therapeutic and prophylactic utilities. For example, these antibody molecules can be administered to cells in culture, e.g. in vitro or ex vivo, or administered in a subject, e.g., in vivo, to treat, prevent, and/or diagnose a variety of disorders. In certain embodiments, for therapeutic applications, the rabbit monoclonal anti-GCC antibody molecules of the invention are humanized, using one or more techniques described above herein.

The antibody molecules, immunoconjugates, and fusion proteins described herein can be used to modulate an activity or function of a GCC protein, such as ligand binding (e.g., binding of ST or guanylin), GCC-mediated signal transduction, maintenance of intestinal fluid, electrolyte homeostasis, intracellular calcium release (calcium flux), cell differentiation, cell proliferation, or cell activation.

In one aspect, the invention features a method of killing, inhibiting or modulating the growth of, or interfering with the metabolism of, a GCC-expressing cell. In one embodiment, the invention provides a method of inhibiting GCC-mediated cell signaling or a method of killing a cell. The method may be used with any cell or tissue which expresses GCC, such as a cancerous cell. Examples of cancerous cells which express GCC include, but are not limited to, a cell from a cancer of the gastrointestinal system (e.g., a cancer of the colon, stomach (gastric), or esophagus), gastrointestinal or bronchopulmonary neuroendocrine tumors, pancreatic cancer, lung cancer (e.g., squamous or adenocarcinoma), liver cancer, neuroectodermal tumors (e.g., phaechromocytomas, paragangliomas), or any metastatic lesions thereof. Nonlimiting examples of GCC-expressing cells include T84 human colonic adenocarcinoma cells, fresh or frozen colonic tumor cells, and cells comprising a recombinant nucleic acid encoding GCC or a portion thereof.

Methods of the invention include the steps of contacting the cell with an anti-GCC antibody molecule or immunoconjugate thereof, as described herein, in an effective amount, i.e., amount sufficient to inhibit GCC-mediated cell signaling or an amount sufficient to kill the cell. The method can be used on cells in culture, e.g. in vitro, in vivo, ex vivo, or in situ. For example, cells that express GCC (e.g., cells collected by biopsy of a tumor or metastatic lesion; cells from an established cancer cell line; or recombinant cells), can be cultured in vitro in culture medium and the contacting step can be effected by adding the anti-GCC antibody molecule or immunoconjugate to the culture medium. In methods of killing a cell, the method comprises using a naked anti-GCC antibody molecule, or an immunoconjugate comprising an anti-GCC antibody molecule and a cytotoxic agent. The method will result in killing of cells expressing GCC, including in particular tumor cells expressing GCC (e.g., colonic tumor cells).

The rabbit monoclonal antibodies of the invention, or humanized versions thereof, can be tested for cellular internalization after binding to GCC using immunofluorescence microscopy techniques well known to those skilled in the art. Such antibodies that are confirmed to internalize would be useful when linked to a cytotoxic moiety for therapeutic purposes, or to a moiety for cell imaging. Antibodies which do not internalize can still be used for diagnostic purposes or for therapeutic methods using naked antibody designed to elicit an antibody-dependent cell-mediated cytotoxic response, or perhaps for liposome delivery methods.

Anti-GCC antibody molecules of the present invention bind to extracellular domains of GCC or portions thereof in cells expressing the antigen. As a result, when practicing the methods of the present invention to kill, suppress, or detect cancerous cells, the antibodies or antigen binding fragments, bind to all such cells, not only to cells which are fixed or cells whose intracellular antigenic domains are otherwise exposed to the extracellular environment. Consequently, binding of the antibodies or antigen binding fragments, is concentrated in areas where there are cells expressing GCC, irrespective of whether these cells are fixed or unfixed, viable or necrotic. For example, when using an antibody molecule of the invention for a detection technique which identifies GCC expression by a dead or permeabilized cell, e.g., immunohistochemistry, the anti-GCC antibody molecule can bind to GCC which is not on the surface, e.g., is in the synthetic process (e.g., in the endoplasmic reticulum or Golgi apparatus). Additionally or alternatively, the anti-GCC antibody molecules, bind to and are internalized with GCC upon binding cells expressing the antigen. Various viewing or imaging techniques can distinguish and/or quantify the binding which is contributed by intracellular GCC.

The method also can be performed on cells present in a subject, as part of an in vivo protocol. In one embodiment, the subject is a human subject. Alternatively, the subject can be a mammal expressing a GCC antigen with which an anti-GCC antibody molecule disclosed herein cross-reacts. An anti-GCC antibody molecule or immunoconjugate thereof can be administered to a human subject for therapeutic purposes. An anti-GCC antibody molecule or immunoconjugate also can be administered to a non-human mammal expressing the GCC-like antigen with which the antibody cross-reacts (e.g., a primate, pig or mouse) for veterinary purposes or as an animal model of human disease. Animal models may be useful for evaluating the therapeutic efficacy of antibodies of the invention (e.g., testing of dosages and time courses of administration). For in vivo embodiments, the contacting step is effected in a subject and includes administering an anti-GCC antibody molecule or immunoconjugate thereof to the subject under conditions effective to permit both binding of the antibody molecule to the extracellular domain of GCC expressed on the cell, and the treating of the cell.

In one embodiment, the invention provides a method of treating cancer by administering an anti-GCC antibody molecule or an immunoconjugate comprising an anti-GCC antibody molecule and a cytotoxic agent to a patient in need of such treatment. The method can be used for the treatment of any cancerous disorder which includes at least some cells that express the GCC antigen. As used herein, the term "cancer" is meant to include all types of cancerous growths or oncogenic processes, metastatic tissues or malignantly transformed cells, tissues, or organs, irrespective of histopathologic type or stage of invasiveness. The terms "cancer" and "tumor" may be used interchangeably (e.g., when used in the context of treatment methods, "treatment of a cancer" and "treatment of a tumor" have the same meaning).

In embodiments, the treatment is sufficient to reduce or inhibit the growth of the subject's tumor, reduce the number or size of metastatic lesions, reduce tumor load, reduce primary tumor load, reduce invasiveness, prolong survival time, or maintain or improve the quality of life.

Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting colon. Adenocarcinomas include malignancies such as non-small cell carcinoma of the lung. Metastatic lesions of the aforementioned cancers can also be treated or prevented using the methods and compositions of the invention.

In some embodiments, the cancer to be treated is a primary or metastatic cancer of the gastrointestinal system (e.g., colorectal cancer, esophageal cancer, or stomach (gastric) cancer). In some embodiments, the cancer to be treated is primary or metastatic pancreatic cancer. In some embodiments, the cancer to be treated is primary or metastatic ovarian cancer. In some embodiments, the cancer to be treated is primary or metastatic liver cancer. In some embodiments, the cancer to be treated is a primary or metastasized neuroectodermal tumor (e.g., phaechromotcytoma, paraganglioma. In some embodiments, the cancer is a primary or a metastasized bronchopulmonary or a gastrointestinal neuroendocrine tumor.

In one embodiment, the cancer is a colorectal cancer, e.g., colorectal adenocarcinoma, colorectal leiomyosarcoma, colorectal lymphoma, colorectal melanoma, or a colorectal neuroendocrine tumor. In a particular embodiment, the cancer is metastatic colon cancer. In another embodiment, the cancer is a stomach cancer (e.g., gastric adenocarcinoma, lymphoma, or sarcoma), or metastasis thereof. In another embodiment, the cancer is an esophageal cancer (e.g., a squamous cell carcinoma or adenocarcinoma of the esophagus). In another embodiment, the cancer is an ovarian cancer, e.g., ovarian leiomyosarcoma. In another embodiment, the cancer is a non-small cell lung cancer (e.g., squamous cell or adenocarcinoma).

The method can be useful in treating a relevant disorder at any stage or subclassification. For example, method can be used to treat early or late stage colon cancer, or colon cancer of any of stages 0, I, IIA, IIB, IIIA, IIIB, IIIC, and IV.

In some embodiments, the method for treating cancer (e.g., a cancer described herein, e.g., colorectal, esophageal, stomach cancer, pancreatic cancer, etc.) comprises administering to a patient in need of such treatment a naked anti-GCC antibody molecule described herein. In other embodiments, the method comprises administering an immunoconjugate comprising an anti-GCC antibody molecule described herein and a cytotoxic agent such as a maytansanoid or an auristatin, or derivatives thereof. Methods of administering antibody molecules and immunoconjugates are described above. Suitable dosages of the molecules used will depend on the age and weight of the subject and the particular compound used.

In some embodiments, the anti-GCC antibody molecule or immunoconjugate is administered in treatment cycles. A "treatment cycle" consists of a treatment period, during which the anti-GCC antibody molecule or immunoconjugate is administered as described above, followed by a rest period, during which no anti-GCC antibody molecule or immunoconjugate is administered. The treatment cycle can be repeated as necessary to achieve the desired effect.

The anti-GCC antibodies described herein (e.g., naked anti-GCC antibody molecules or immunoconjugates comprising an anti-GCC antibody molecule and a therapeutic agent) may be used in combination with other therapies. For example, the combination therapy can include a composition of the present invention co-formulated with, and/or co-administered with, one or more additional therapeutic agents, e.g., one or more anti-cancer agents, e.g., cytotoxic or cytostatic agents, hormone treatment, vaccines, and/or other immunotherapies. In other embodiments, the anti-GCC antibodies are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the anti-GCC antibody molecule or immunoconjugate thereof is used in combination with a chemotherapeutic agent. Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

The selection of therapeutic agent(s) or treatment modality to be combined with an anti-GCC antibody molecule or immunoconjugate of the invention will depend on the disorder to be treated. The additional agent(s) or treatment modality may include, for example, standard approved therapies for the indication being treated. For example, when the anti-GCC antibody molecule or immunoconjugate thereof is used to treat colon cancer, it may be used in combination with, e.g., surgery; radiation therapy; 5-fluorouracil (5-FU), capecitibine, leucovorin, irinotecan, oxaliplatin, bevacizumab, cetuximab, panitumum, or combinations thereof (e.g., oxaliplatin/capecitibine (XELOX), 5-fluorouricil/leucovorin/-oxaliplatin (FOLFOX), 5-fluorouricil/leucovorin/irinotecan (FOLFIRI), FOLFOX plus bevacizumab, or FOLFIRI plus bevacizumab).

In another aspect, the invention features the use of an anti-GCC antibody molecule or immunoconjugate as described herein in the manufacture of a medicament. In an embodiment, the medicament is for treating cancer, e.g., a gastrointestinal cancer. In some embodiments, the medicament comprises an anti-GCC antibody molecule having features summarized in Tables 1-6. In some embodiments, the medicament comprises a MIL-44-148-2 or a MIL-44-67-4 antibody molecule, or humanized versions thereof.

Anti-GCC antibodies and immunoconjugates described herein can also be used to detect the presence of GCC, e.g., to detect the presence of GCC in a biological sample (e.g., a biological sample obtained from a subject), or to detect the presence or distribution of GCC in a subject (i.e., in vivo detection). The term "detecting" as used herein encompasses quantitative or qualitative detection. Detecting GCC or GCC protein, as used herein, means detecting intact GCC protein or detecting a portion of the GCC protein that comprises the epitope to which the anti-GCC antibody molecule binds.

Accordingly, in another aspect, the invention features, a method of detecting GCC protein, e.g., detecting a GCC expressing cell or tissue, e.g., a tumor cell, or a tumor having cells, that express GCC. The method comprises: contacting a material, e.g., a cell or tissue, e.g., a sample of a tumor which expresses GCC, with an anti-GCC antibody molecule, e.g., an anti-GCC antibody molecule described herein, under conditions which allow formation of a complex between the anti-GCC antibody molecule and GCC protein; and detecting formation of a complex between antibody molecule and GCC protein, to thereby detect the presence of GCC protein, e.g., to detect a GCC expressing cell or tumor.

In an embodiment the anti-GCC antibody molecule is an immunoconjugate comprising a detectable label.

In certain embodiments, the tissues include normal and/or cancerous tissues that express GCC at higher levels relative to other tissues, for example other tissue such as B cells and/or B cell associated tissues.

Methods of detection described herein, whether in vitro or in vivo, can be used to evaluate a subject. In an embodiment the method is performed in vivo, and can be used, e.g., for imaging, staging, evaluation or diagnosis of a patient. In certain embodiments, the disorder is a cell proliferative disorder, such as a cancer or a tumor, e.g., colon cancer.

Thus, in another aspect, the invention provides, a method for detecting the presence of GCC protein in vitro (e.g., in a biological sample, such as a tissue biopsy, e.g., from a tumor tissue, from a subject) or in vivo (e.g., by in vivo imaging in a subject). The method comprises: (i) contacting a sample with an anti-GCC antibody molecule or immunoconjugate thereof, or administering to a subject, an anti-GCC antibody molecule or immunoconjugate thereof; and (ii) detecting formation of a complex between the anti-GCC antibody molecule and GCC protein. Complex formation is indicative of the presence or level of GCC.

In embodiments the level of complex detected in the sample or subject is compared with a reference value, e.g., a value for complex formation or level of GCC. In an embodiment a level of GCC which exceeds a reference value is indicative of a GCC-mediated disorder.

In an embodiment the method comprises contacting a reference sample, e.g., a control sample (e.g., a control biological sample, such as plasma, tissue, biopsy) or a control subject) with an anti-GCC antibody molecule or immunoconjugate thereof and comparing the level of complex detected therein with the level detected in the sample or subject.

In certain embodiments, a test cell or tissue is obtained from an individual suspected of having a disorder associated with increased expression of GCC. In certain embodiments, a test cell or tissue is obtained from an individual suspected of having a disorder associated with GCC expression in a location other than the apical surface of intestinal epithelial cells (e.g., cytoplasmic GCC expression in intestinal epithelial cells, or GCC expression in non-intestinal cells or tissue).

In an embodiment the level of GCC, in a sample from the subject, or in the subject, is compared with a reference level, e.g., the level of GCC in a control material, e.g., a normal cell of the same tissue origin as the subject's cell or a cell having GCC at levels comparable to such a normal cell. The method can comprise, e.g., responsive to the detected level of GCC, providing a diagnosis, a prognosis, an evaluation of the efficacy of treatment, or the staging of a disorder. A higher level of GCC in the sample or subject, as compared to the control material, indicates the presence of a disorder associated with increased expression of GCC. A higher level of GCC in the sample or subject, as compared to the control material, can also indicate the relative lack of efficacy of a treatment, a relatively poorer prognosis, or a later stage of disease. The level of GCC can also be used to evaluate or select future treatment, e.g., the need for more or less aggressive treatment, or the need to switch from one treatment regimen to another.

The level of GCC can also be used to select or evaluate patients. E.g., in embodiments patients whose tumor cells express high amounts of GCC on their surfaces would be considered good candidates for treatment with toxin-conjugated anti-GCC antibody molecules, such as an immunoconjugate as described herein, or the toxin-conjugated antibodies as described in U.S. Published Patent Application No. 20110110936, the contents of which are incorporated by reference herein in its entirety. In embodiments patients whose tumor cells express low amounts of GCC on their surfaces would not be as good candidates for this or might be candidates for combining the anti-GCC antibody molecule with an additional treatment method, or be candidates for naked antibody therapy. In another example, the dose of the toxin-conjugated anti-GCC antibody molecule could be adjusted to reflect the number of GCC molecules expressed on the surfaces of tumor cells. Patients with high numbers of GCC molecules on their tumor cell surfaces might be treated with lower doses than patients with low numbers of GCC molecules. Detecting the presence of GCC-expressing tumor cells in vivo can allow identification of tissues into which the primary GCC-expressing tumor has metastasized. Knowledge of which tissues have metastases can lead to targeted application of tumor therapy.

As discussed above, the antibody molecules described herein permit assessment of the presence of a GCC protein in normal versus neoplastic tissues, through which the presence or severity of disease, disease progress and/or the efficacy of therapy can be assessed. For example, therapy can be monitored and efficacy assessed. In one example, a GCC protein can be detected and/or measured in a first sample obtained from a subject having an inflammatory disease and therapy can be initiated. Later, a second sample can be obtained from the subject and GCC protein in the sample can be detected and/or measured. A decrease in the quantity of GCC protein detected or measured in the second sample can be indicative of therapeutic efficacy.

Exemplary cell proliferative disorders that may be evaluated, e.g., diagnosed, using an antibody disclosed herein include a proliferative disorder including, but not limited to, colon cancer, stomach (gastric) cancer, esophageal cancer, pancreatic cancer, lung cancer, liver cancer, and ovarian cancer.

In certain embodiments, a method, such as those described above, comprises detecting binding of an anti-GCC antibody to GCC expressed on the surface of a cell or in a membrane preparation obtained from a cell expressing GCC on its surface. In certain embodiments, the method comprises contacting a cell with an anti-GCC antibody under conditions permissive for binding of the anti-GCC antibody to GCC, and detecting whether a complex is formed between the anti-GCC antibody and GCC on the cell surface. An exemplary assay for detecting binding of an anti-GCC antibody to GCC expressed on the surface of a cell is a "FACS" assay.

In certain embodiments, in vitro methods for detecting the presence of GCC protein allow for the detection of both cell surface level and internal GCC expression. For example, immunohistochemistry (IHC) using an anti-GCC antibody of the invention allows for the detection of cell surface level expression and internal expression (e.g. expression within a cell or tissue, such as a tumor) of GCC in biological sample. In contrast, in vivo administration of an immunoconjugate of the invention (e.g., a labeled anti-GCC antibody of the invention) detects GCC expression on a cell or tissue surface.

Without intending to be bound by any theory, vascularization may be required for a targeted GCC therapeutic to access a GCC expressing tumor, particularly in instances where the targeted GCC therapeutic is administered intravenously. Thus, in certain embodiments of in vitro detection methods of the invention, it may be useful to evaluate or characterize tumor vasculature in addition to or in conjunction with the detection of GCC protein. For example, a tissue sample can be stained with an agent that identifies a vascular endothelial cell, such as an anti-CD-31 antibody molecule or an anti-von Willebrand Factor antibody molecule, and an anti-GCC antibody of the invention to simultaneously or contemporaneously characterize GCC expression and tissue vascularization. In certain aspects of the invention, such simultaneously or contemporaneous characterization of GCC expression and vasculature is useful as a patient selection tool for a targeted GCC therapeutic.

In another aspect, cell surface expression of GCC may be required for a targeted GCC therapeutic to affect the killing of a GCC expressing tumor cell. For example, some tumor cells may be expressing GCC, but not on the cell surface. If a therapeutic depends on cell surface GCC expression, such a therapeutic may not be able to kill a cell where GCC is primarily intracellular. Thus, in some embodiments of the invention, the diagnostic or prognostic assay can further include analysis and/or quantification of cellular location of GCC, e.g. a method which can distinguish and/or quantify cell surface expression from intracellular expression. Without intending to be bound by any theory, a patient whose tumor primarily has intracellular GCC expression, may not be a good candidate for an anti-GCC antibody molecule which binds to the extracellular domain of GCC. Alternatively, such an analytical result may prompt initial treatment with an agent which induces cell surface expression of GCC (see, e.g., PCT publication No. WO04/071436). Following, or in conjunction with GCC cell surface induction, an anti-GCC antibody molecule which has access to or binds only to extracellularly expressed GCC can be administered.

Exemplary biological samples for methods described herein comprise tissue or body fluid, such as an inflammatory exudate, blood, serum, bowel fluid, stool sample, or a biopsy. In one example, a sample (e.g., tissue and/or body fluid) can be obtained from an individual and a suitable immunological method can be used to detect and/or measure GCC protein expression. Suitable immunological methods for detecting or measuring GCC protein expression include enzyme-linked immunosorbent assays (ELISA), radioimmunoassay, immunohistology, flow cytometry, and the like (collectively referred to as "immunoassays").

One having ordinary skill in the art can readily appreciate the multitude of ways to practice an immunoassay to detect the presence of GCC in a sample. In a particular embodiment, GCC is detected or measured by immunohistochemistry using an anti-GCC antibody of the invention (e.g., MIL-44-148-2). Immunohistochemistry techniques may be used to identify and essentially stain cells with ST receptor. Such "staining" allows for analysis of metastatic migration. Anti-GCC antibodies such as those described herein are contacted with fixed cells and the GCC present in the cells reacts with the antibodies. The antibodies are detectably labeled or detected using labeled second antibody or protein A to stain the cells.

According to some embodiments, immunoassays comprise allowing proteins in the sample to bind a solid phase support such as a plastic surface. Detectable antibodies are then added which selectively bind to GCC. Detection of the detectable antibody indicates the presence of ST receptor protein. The detectable antibody may be a labeled or an unlabelled antibody. Unlabeled antibody may be detected using a second, labeled antibody that specifically binds to the first antibody or a second, unlabelled antibody which can be detected using labeled protein A, a protein that complexes with antibodies. Various immunoassay procedures are described in Immunoassays for the 80's, A. Voller et al., Eds., University Park, 1981, which is incorporated herein by reference.

Simple immunoassays may be performed in which a solid phase support is contacted with the test sample. Any proteins present in the test sample bind the solid phase support and can be detected by a specific, detectable antibody preparation. Such a technique is the essence of the dot blot, Western blot and other such similar assays.

Other immunoassays may be more complicated but actually provide excellent results. Typical and preferred immunometric assays include "forward" assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control. Such "two-site" or "sandwich" assays are described by Wide, Radioimmune Assay Method, Kirkham, Ed., E. & S. Livingstone, Edinburgh, 1970, pp. 199-206, which is incorporated herein by reference.

Other types of immunometric assays are the so-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample.

The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays. The reverse assay may also be adapted in a similar manner for the detection of antibodies in a test sample.

The first component of the immunometric assay may be added to nitrocellulose or other solid phase support which is capable of immobilizing proteins. The first component for determining the presence of ST receptor in a test sample is anti-ST receptor antibody. By "solid phase support" or "support" is intended any material capable of binding proteins.

Well-known solid phase supports include glass, polystyrene, polypropylene, polyethylene, dextran, nylon, amylases, natural and modified celluloses, polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate.

Antibody Labeling and Detection

Anti-GCC antibody molecules used in methods described herein, e.g., in the in vivo and in vitro detection, e.g., diagnostic, staging, or imaging methods, can be directly or indirectly labeled with a detectable substance to facilitate detection of the bound or unbound binding agent. Suitable detectable substances include various biologically active enzymes, ligands, prosthetic groups, fluorescent materials, luminescent materials, chemiluminescent materials, bioluminescent materials, chromophoric materials, electron dense materials, paramagnetic (e.g., nuclear magnetic resonance active) materials, and radioactive materials. In some embodiments, the anti-GCC antibody molecule is coupled to a radioactive ion, e.g., indium ($^{111}$In), iodine ($^{131}$I or $^{125}$I), yttrium ($^{90}$Y), lutetium ($^{177}$Lu), actinium ($^{225}$Ac), bismuth ($^{212}$Bi or $^{213}$Bi), sulfur ($^{35}$S), carbon ($^{14}$C), tritium ($^{3}$H), rhodium ($^{188}$Rh), technetium ($^{99}$mTc), praseodymium, or phosphorous ($^{32}$P); or a positron-emitting radionuclide, e.g., carbon-11 ($^{11}$C) potassium-40 ($^{40}$K), nitrogen-13 ($^{13}$N), oxygen-15 ($^{15}$O), fluorine-18 ($^{18}$F), gallium ($^{68}$Ga), and iodine-121 ($^{121}$I).

Exemplary labels include fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, and 2,3-dihydrophthalazinediones Other exemplary labels include horseradish peroxidase (HRP), alkaline phosphatase, galactosidase, glucoamylase, lysozyme, saccharide oxidases, e.g., glucose oxidase, galactose oxidase, and glucose 6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Fluorophore and chromophore labeled antibody molecules can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescent compounds and chromophores are described by Stryer Science, 162:526 (1968) and Brand, L. et al. *Annual Review of Biochemistry*, 41:843-868 (1972). The antibodies can be labeled with fluorescent chromophore groups by conventional procedures such as those disclosed in U.S. Pat. Nos. 3,940,475, 4,289,747, and 4,376,110.

One group of fluorescers having a number of the desirable properties described above is the xanthene dyes, which include the fluoresceins derived from 3,6-dihydroxy-9-henylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

Labeled antibody molecules can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen Certain other methods can be used to detect binding of anti-GCC antibodies to GCC.

Such methods include, but are not limited to, antigen-binding assays that are known in the art, such as western blots, radioimmunoassays, ELISA (enzyme linked immunosorbent assay), "sandwich" Immunoassays, immunoprecipitation assays, fluorescent immunoassays, protein A immunoassays, and immunohistochemistry (IHC).

Complex formation between the anti-GCC antibody molecule and GCC can be detected by measuring or visualizing either the antibody (or antibody fragment) bound to the GCC antigen or unbound antibody molecule. Conventional detection assays can be used, e.g., western blots, radioimmunoassays, ELISA (enzyme linked immunosorbent assay), "sandwich" immunoassays, immunoprecipitation assays, fluorescent immunoassays, protein A immunoassays, and immunohistochemistry (IHC) or radioimmunoassay (RIA).

Alternative to labeling the anti-GCC antibody molecule, the presence of GCC can be assayed in a sample by a competition immunoassay utilizing standards labeled with a detectable substance and an unlabeled anti-GCC antibody molecule. In this assay, the biological sample, the labeled standards and the GCC binding agent are combined and the amount of labeled standard bound to the unlabeled antibody is determined. The amount of GCC in the sample is inversely proportional to the amount of labeled standard bound to the GCC binding agent.

It is also possible to directly detect GCC to anti-GCC antibody molecule complex formation without further manipulation or labeling of either component (GCC or antibody molecule), for example by utilizing the technique of fluorescence energy transfer (FET, see, for example, Lakowicz et al., U.S. Pat. No. 5,631,169; Stavrianopoulos, et al., U.S. Pat. No. 4,868,103). A fluorophore label on the first, "donor" molecule is selected such that, upon excitation with incident light of appropriate wavelength, its emitted fluorescent energy will be absorbed by a fluorescent label on a second "acceptor" molecule, which in turn is able to fluoresce due to the absorbed energy. Alternately, the "donor" protein molecule may simply utilize the natural fluorescent energy of tryptophan residues. Labels are chosen that emit different wavelengths of light, such that the "acceptor" molecule label may be differentiated from that of the "donor". Since the efficiency of energy transfer between the labels is related to the distance separating the molecules, spatial relationships between the molecules can be assessed. In a situation in which binding occurs between the molecules, the fluorescent emission of the "acceptor" molecule label in the assay should be maximal. An FET binding event can be conveniently measured through standard fluorometric detection means well known in the art (e.g., using a fluorimeter).

In another example, determination of the ability of an antibody molecule to recognize GCC can be accomplished without labeling either assay component (GCC or antibody molecule) by utilizing a technology such as real-time Biomolecular Interaction Analysis (BIA) (see, e.g., Sjolander, S, and Urbaniczky, C., 1991, Anal. Chem. 63:2338-2345 and Szabo et al., 1995, Curr. Opin. Struct. Biol. 5:699-705). As used herein, "BIA" or "surface plasmon resonance" is a technology for studying biospecific interactions in real time, without labeling any of the interactants (e.g., BIACORE™). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In still another embodiment, the invention provides a method for detecting the presence of GCC-expressing tumor tissues in vivo. The method includes (i) administering to a subject (e.g., a patient having a cancer) an anti-GCC antibody or antigen binding fragment thereof, preferably a antibody or antigen binding fragment thereof conjugated to a detectable label or marker; (ii) exposing the subject to a means for detecting said detectable label or marker to the GCC-expressing tissues or cells.

Examples of labels useful for diagnostic imaging in accordance with the present invention are radiolabels such as $^{131}$I, $^{111}$In, $^{99}$mTc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes (e.g., $^{68}$Ga, $^{18}$F) detectable by a single photon emission computed tomography ("SPECT") detector or positron emission tomography ("PET") scanner, chemiluminescers such as luciferin, and enzymatic markers such as peroxidase or phosphatase. Short-range radiation emitters, such as isotopes detectable by short-range detector probes, such as a transrectal probe, can also be employed. The antibody can be labeled with such reagents using techniques known in the art. For example, see Wensel and Meares (1983) Radioimmunoimaging and Radioimmunotherapy, Elsevier, N.Y., for techniques relating to the radiolabeling of antibodies. See also, D. Colcher et al. Meth. Enzymol. 121: 802-816 (1986.

In the case of a radiolabeled antibody, the antibody is administered to the patient, is localized to the tumor bearing the antigen with which the antibody reacts, and is detected or "imaged" in vivo using known techniques such as radio-nuclear scanning using e.g., a gamma camera or emission tomography or computed tomography. See e.g., A. R. Bradwell et al., "Developments in Antibody Imaging", Monoclonal Antibodies for Cancer Detection and Therapy, R. W. Baldwin et al., (eds.), pp 65-85 (Academic Press 1985). Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N, $^{68}$Ga).

In other embodiments, the invention provides methods for determining the dose, e.g., radiation dose, that different tissues are exposed to when a subject, e.g., a human subject, is administered an anti-GCC antibody molecule that is conjugated to a radioactive isotope. The method includes: (i) administering an anti-GCC antibody molecule as described herein, e.g., a anti-GCC antibody molecule, that is labeled with a radioactive isotope to a subject; (ii) measuring the amount of radioactive isotope located in different tissues, e.g., tumor, or blood, at various time points until some or all of the radioactive isotope has been eliminated from the body of the subject; and (iii) calculating the total dose of radiation received by each tissue analyzed. The measurements can be taken at scheduled time points, e.g., day 1, 2, 3, 5, 7, and 12, following administration (at day 0) of the radioactively labeled anti-GCC antibody molecule to the subject. The concentration of radioisotope present in a given tissue, integrated over time, and multiplied by the specific activity of the radioisotope can be used to calculate the dose that a given tissue receives. Pharmacological information generated using anti-GCC antibody molecules labeled with one radioactive isotope, e.g., a gamma-emitter, e.g., $^{111}$In can be used to calculate the expected dose that the same tissue would receive from a different radioactive isotope which cannot be easily measured, e.g., a beta-emitter, e.g., $^{90}$Y.

Kits

Also within the scope of the invention are kits comprising an anti-GCC antibody molecule or immunoconjugate as described herein. Further included are kits comprising liposome compositions comprising an anti-GCC antibody molecule or immunoconjugate. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject. Instructions for use can include instructions for diagnostic applications of the anti-GCC antibody molecule or immunoconjugate to detect GCC, in vitro, e.g., in a sample, e.g., a biopsy or cells from a patient having a cancer, or in vivo. The instructions can include guidance for therapeutic application including suggested dosages and/or modes of administration, e.g., in a patient with a cancer (e.g., a cancer of gastrointestinal origin, such as, for example, colon cancer, stomach cancer, esophageal cancer). Other instructions can include instructions on coupling of the antibody to a chelator, a label or a therapeutic agent, or for purification of a conjugated antibody, e.g., from unreacted conjugation components. As discussed above, the kit can include a label, e.g., any of the labels described herein. As discussed above, the kit can include a therapeutic agent, e.g., a therapeutic agent described herein. In some applications the antibody will be reacted with other components, e.g., a chelator or a label or therapeutic agent, e.g., a radioisotope, e.g., yttrium or lutetium. In such cases the kit can include one or more of a reaction vessel to carry out the reaction or a separation device, e.g., a chromatographic column, for use in separating the finished product from starting materials or reaction intermediates.

The kit can further contain at least one additional reagent, such as a diagnostic or therapeutic agent, e.g., a diagnostic or therapeutic agent as described herein, and/or one or more additional anti-GCC antibody molecules or immunoconjugates, formulated as appropriate, in one or more separate pharmaceutical preparations.

The kit can further contain a radioprotectant. The radiolytic nature of isotopes, e.g., $^{90}$Yttrium ($^{90}$Y) is known. In order to overcome this radiolysis, radioprotectants may be included, e.g., in the reaction buffer, as long as such radioprotectants are benign, meaning that they do not inhibit or otherwise adversely affect the labeling reaction, e.g., of an isotope, such as of $^{90}$Y, to the antibody. The formulation buffer of the present invention may include a radioprotectant such as human serum albumin (HSA) or ascorbate, which minimize radiolysis due to yttrium or other strong radionuclides. Other radioprotectants are known in the art and can also be used in the formulation buffer of the present invention, i.e., free radical scavengers (phenol, sulfites, glutathione, cysteine, gentisic acid, nicotinic acid, ascorbyl palmitate, HOP(:O)H$_2$I glycerol, sodium formaldehyde sulfoxylate, Na$_2$S2O, Na$_2$S$_2$O$_3$, and SO$_2$, etc.).

A provided kit is one useful for radiolabeling a chelator-conjugated protein or peptide with a therapeutic radioisotope for administration to a patient. The kit includes (i) a vial containing chelator-conjugated antibody, (ii) a vial containing formulation buffer for stabilizing and administering the radiolabeled antibody to a patient, and (iii) instructions for performing the radiolabeling procedure. The kit provides for exposing a chelator-conjugated antibody to the radioisotope or a salt thereof for a sufficient amount of time under amiable conditions, e.g., as recommended in the instructions. A radiolabeled antibody having sufficient purity, specific activity and binding specificity is produced. The radiolabeled antibody may be diluted to an appropriate concentration, e.g., in formulation butter, and administered directly to the patient with or without further purification. The chelator-conjugated antibody may be supplied in lyophilized form.

The following examples are illustrative but are not meant to be limiting of the present invention.

EXAMPLES

Example 1

Generation of a Human GCC Extracellular Domain-Mouse Fc (hGCC-ECD-mFc) Fusion Protein The generation of a secreted human (h) guanylyl cyclase (GCC) (hGCC) extracellular domain (ECD)/mouse immunoglobulin (Ig)G2a heavy chain constant (Fc) (with receptor binding region mutation (FcRbr-mutII) fusion protein (i.e., hGCC(ECD)-mIgG2a RcRbr-mutII fusion protein, also referred to herein as pLKTOK108 and MIL-44) for immunization and screening was performed as follows. GCC antigen was prepared by subcloning a portion of the GCC gene encoding a sequenced comprising the following GCC sequence (signal sequence and extracellular domain) into the pLK-TOK4 expression vector:

```
                                              (SEQ ID NO: 46)
MKTLLLDLALWSLLFQPGWLSFSSQVSQNCHNGSYEISVLMMGNSAFAEP

LKNLEDAVNEGLEIVRGRLQNAGLNVTVNATFMYSDGLIHNSGDCRSSTC

EGLDLLRKISNAQRMGCVLIGPSCTYSTFQMYLDTELSYPMISAGSFGLS

CDYKETLTRLMSPARKLMYFLVNFWKTNDLPFKTYSWSTSYVYKNGTETE

DCFWYLNALEASVSYFSHELGFKVVLRQDKEFQDILMDHNRKSNVIIMCG

GPEFLYKLKGDRAVAEDIVIILVDLFNDQYFEDNVTAPDYMKNVLVLTLS

PGNSLLNSSFSRNLSPTKRDFALAYLNGILLFGHMLKIFLENGENITTPK

FAHAFRNLTFEGYDGPVTLDDWGDVDSTMVLLYTSVDTKKYKVLLTYDTH

VNKTYPVDMSPTFTWKNSKL
```

The amino acid sequence GLy-Arg-Gly-Pro-Gln (SEQ ID NO: 66), at positions 427 to 430, was selected to terminate the extracellular GCC fragment. In GCC, this sequence is immediately followed by a Pro that aligns well with a Pro at the position homologous to the Pro that is historically used to initiate human IgG1 Fc fusion proteins.

The mouse IgG2a Fc region of pLKTOK108 was designed to start with the amino acid sequence that functionally is the end of the CH1 domain [Pro-Arg-Valine (Val)-Pro-Isoleucine (Ile)-Threonine (Thr)-Glu-Asparagine (Asn)](SEQ ID NO: 58). Two regions were mutated in the mouse IgG2a constant region. In addition to the leucine (Leu)-Leu-Gly-Gly (SEQ ID NO: 59) to Leu-alanine (Ala)-Gly-Ala (SEQ ID NO: 60) mutations (positions 234 to 237 Lysine [Lys]-Lys-Gly-Gly (SEQ ID NO: 61) to Lys-Ala-Gly-Ala (SEQ ID NO: 62), the second Fc receptor region at positions 318 to 322 was also mutated as follows: glutamic acid (Glu)-Phenylalanine (Phe)-Lys-Cysteine (Cys)-Lys (SEQ ID NO: 63) to Ala-Phe-Lys-Cys-Lys (SEQ ID NO: 64) and then to Phe-Lys-Cys-Lys (SEQ ID NO: 65).

Once the complete fusion protein sequence was designed, flanking restriction enzyme sequences for BamHI and XbaI, as well as the Kozak sequence (CTCACC) and a terminal stop codon were added to complete the fusion protein cDNA. The nucleotide and amino acid sequences of the fusion protein pLKTOK108 (hGCC/mIgG2a FcRmutII) is provided below (the BamHI and XbaI restriction sites are shown in lower case letters in SEQ ID NO: 47):

```
Human GCC-ECD/mouse IgG2a Fc nucleotide sequence   (SEQ ID NO: 47)
cgcggatccctcaccATGAAGACGTTGCTGTTGGACTTGGCTTTGTGGTCACTGCTCTTCCAG

CCCGGGTGGCTGTCCTTTAGTTCCCAGGTGAGTCAGAACTGCCACAATGGCAGCTAT

GAAATCAGCGTCCTGATGATGGGCAACTCAGCCTTTGCAGAGCCCCTGAAAAACTTG

GAAGATGCGGTGAATGAGGGGCTGGAAATAGTGAGAGGACGTCTGCAAAATGCTGG

CCTAAATGTGACTGTGAACGCTACTTTCATGTATTCGGATGGTCTGATTCATAACTCA

GGCGACTGCCGGAGTAGCACCTGTGAAGGCCTCGACCTACTCAGGAAAATTTCAAA

TGCACAACGGATGGGCTGTGTCCTCATAGGGCCCTCATGTACATACTCCACCTTCCA

GATGTACCTTGACACAGAATTGAGCTACCCCATGATCTCAGCTGGAAGTTTTGGATT

GTCATGTGACTATAAAGAAACCTTAACCAGGCTGATGTCTCCAGCTAGAAAGTTGAT

GTACTTCTTGGTTAACTTTTGGAAAACCAACGATCTGCCCTTCAAAACTTATTCCTGG

AGCACTTCGTATGTTTACAAGAATGGTACAGAAACTGAGGACTGTTTCTGGTACCTT

AATGCTCTGGAGGCTAGCGTTTCCTATTTCTCCCACGAACTCGGCTTTAAGGTGGTGT

TAAGACAAGATAAGGAGTTTCAGGATATCTTAATGGACCACAACAGGAAAAGCAAT

GTGATTATTATGTGTGGTGGTCCAGAGTTCCTCTACAAGCTGAAGGGTGACCGAGCA

GTGGCTGAAGACATTGTCATTATTCTAGTGGATCTTTTCAATGACCAGTACTTGGAG

GACAATGTCACAGCCCCTGACTATATGAAAAATGTCCTTGTTCTGACGCTGTCTCCT

GGGAATTCCCTTCTAAATAGCTCTTTCTCCAGGAATCTATCACCAACAAAACGAGAC

TTTGCTCTTGCCTATTTGAATGGAATCCTGCTCTTTGGACATATGCTGAAGATATTTC

TTGAAAATGGAGAAAATATTACCACCCCCAAATTTGCTCATGCTTTCAGGAATCTCA

CTTTTGAAGGGTATGACGGTCCAGTGACCTTGGATGACTGGGGGGATGTTGACAGTA

CCATGGTGCTTCTGTATACCTCTGTGGACACCAAGAAATACAAGGTTCTTTTGACCT

ATGATACCCACGTAAATAAGACCTATCCTGTGGATATGAGCCCCACATTCACTTGGA

AGAACTCTAAACTTCCTAATGATATTACAGGCCGGGGCCCTCAGCCCAGAGTGCCCA

TAACACAGAACCCCTGTCCTCCACTCAAAGAGTGTCCCCCATGCGCAGCTCCAGACC

TCGCAGGTGCACCATCCGTCTTCATCTTCCCTCCAAAGATCAAGGATGTACTCATGA

TCTCCCTGAGCCCCATGGTCACATGTGTGGTGGTGGATGTGAGCGAGGATGACCCAG

ACGTCCAGATCAGCTGGTTTGTGAACAACGTGGAAGTACACACAGCTCAGACACAA

ACCCATAGAGAGGATTACAACAGTACTCTCCGGGTGGTCAGTGCCCTCCCCATCCAG

CACCAGGACTGGATGAGTGGCAAGGCATTCAAATGCAAGGTCAACAACAGAGCCCT

CCCATCCCCCATCGAGAAACCATCTCAAAACCCAGAGGGCCAGTAAGAGCTCCAC

AGGTATATGTCTTGCCTCCACCAGCAGAAGAGATGACTAAGAAAGAGTTCAGTCTG

ACCTGCATGATCACAGGCTTCTTACCTGCCGAAATTGCTGTGGACTGGACCAGCAAT

GGGCGTACAGAGCAAAACTACAAGAACACCGCAACAGTCCTGGACTCTGATGGTTC

TTACTTCATGTACAGCAAGCTCAGAGTACAAAAGAGCACTTGGGAAAGAGGAAGTC
```

```
TTTTCGCCTGCTCAGTGGTCCACGAGGGTCTGCACAATCACCTTACGACTAAGACCA

TCTCCCGGTCTCTGGGTAAATAAtctagagca
```

Human GCC-ECD/mouse IgG2a Fc amino acid sequence (SEQ ID NO: 48):
MKTLLLDLALWSLLFQPGWLSFSSQVSQNCHNGSYEISVLMMGNSAFAEPLKNLEDAV

NEGLEIVRGRLQNAGLNVTVNATFMYSDGLIHNSGDCRSSTCEGLDLLRKISNAQRMGC

VLIGPSCTYSTFQMYLDTELSYPMISAGSFGLSCDYKETLTRLMSPARKLMYFLVNFWK

TNDLPFKTYSWSTSYVYKNGTETEDCFWYLNALEASVSYFSHELGFKVVLRQDKEFQDI

LMDHNRKSNVIIMCGGPEFLYKLKGDRAVAEDIVIILVDLFNDQYLEDNVTAPDYMKN

VLVLTLSPGNSLLNSSFSRNLSPTKRDFALAYLNGILLFGHMLKIFLENGENITTPKFAHA

FRNLTFEGYDGPVTLDDWGDVDSTMVLLYTSVDTKKYKVLLTYDTHVNKTYPVDMSP

TFTWKNSKLPNDITGRGPQPRVPITQNPCPPLKECPPCAAPDLAGAPSVFIFPPKIKDVLMI

SLSPMVTCVVVDVSEDDPDVQISWFVNNVEVHTAQTQTHREDYNSTLRVVSALPIQHQ

DWMSGKAFKCKVNNRALPSPIEKTISKPRGPVRAPQVYVLPPPAEEMTKKEFSLTCMIT

GFLPAEIAVDWTSNGRTEQNYKNTATVLDSDGSYFMYSKLRVQKSTWERGSLFACSVV

HEGLHNHLTTKTISRSLGK

As stated above, the recombinant protein pLKTOK108 combines the extracellular region of human GCC fused to a mouse IgG2a Fc region in which the two mutated Fc receptor binding regions (FcRs) were mutated to prevent Fc receptor binding (mIgG2a FcRmutII). The recombinant DNA insert for pLKTOK108 was created by a three-step PCR process as follows:

The first step created the adapted extracellular human GCC and the adapted mouse IgG2a FcRmutII DNA fragments containing 35 nucleotides of overlapping sequences. These PCR reactions used the templates and primers described in Table 7 and Table 8 with the protocol described in Table 9 to create the two fragments. These DNA fragments were isolated from a 1% agarose gel using a Qiagen Gel Purification kit (Valencia, Calif.). The human GCC template was provided by a protein expression vector containing the sequence for human GCC (Clontech Laboratories, Inc., Mountain View, Calif., USA). The template for the Fc domain was obtained from an expression construct for human 1228 fused to mouse IgG2aFc with two mutated Fc receptor binding regions (FcRmutII), referred to as pLKTOK84, that itself were created using the vector pLKTOK61 (described in U.S. Pat. No. 7,053,202, the contents of which are incorporated by reference herein in its entirety) as a template.

TABLE 8

Primers Used in All PCR Reactions to Create pLKTOK108

| Primer Name | Sequence | SEQ ID NO: |
|---|---|---|
| pGCCFC5 | 5'-CGCGGATCCCTCACCATGAAGACGTTGC-TGTTGGACTTGGC-3' | 49 |
| pGCCFCMuA | 5'-TGGGCACTCTGGGCTGAGGGCCCCGGCC-TGTAATATCATTAG-3' | 50 |
| pGCCFCMuB | 5'-CAGGCCGGGGCCCTCAGCCCAGAGTGCC-CATAACACAGAACCCCTGTCC-3' | 51 |
| pMICOS-4 | 5-TGCTCTAGATTATTTACCCAGAGACCGG-GAGATGGTCTTA | 52 |
| pSMUCH2 | 5'-ACCTGTGGAGCTCTTACTGG-3' | 53 |
| EF5S | 5'-CATTTCAGGTGTCGTGAGGA-3' | 54 |
| SP6 | 5'-ATTTAGGTGACACTATAG-3' | 55 |
| M13f | 5'-GTTTTCCCAGTCACGAC-3' | 56 |
| M13r | 5'-AACAGCTATGACCATG-3' | 57 |

TABLE 7

Templates Used in First Step PCR Assembly Reactions to Create Recombinant DNA for pLKTOK108

| Number | Product | Template | Primer 1 | Primer 2 | Size |
|---|---|---|---|---|---|
| 1A | Extracellular CCC | Human GCC-Vect | pGCCFC5 | pGCCFCMuA | 1300 bp |
| 1B | Mouse IgG2a-FcRmutII | pLKTOK84 | pGCCFCMuB | pMICOS-4 | 700 bp |

TABLE 9

Reaction Protocol Used in First Step PCR Assembly Reactions to Create Recombinant DNA for pLKTOK108

| Reaction Mixture | Machine settings |
| --- | --- |
| 1 uL DNA (1:100 miniprep of template) | 94° C.-2 minutes |
| 0.2 uL 200 mM Primer 1 | |
| 0.2 uL 200 mM Primer 2 | 30 cycles |
| 10 uL 10× PCR buffer | 94° C.-1 minutes |
| 3 uL 50 mM MgCl$_2$ | 55° C.-30 seconds |
| 2 uL 10 mM dNTP mix | 72° C.-2 minutes |
| 83.5 uL H$_2$O | |
| 0.5 uL Taq polymerase | 72° C.-10 minutes |

The second PCR reaction combined the templates in the concentrations listed in Table 10. The reaction protocol listed in Table 11 created a single recombinant fusion protein gene. The product of this reaction was used directly as the template in the third PCR reaction.

TABLE 10

Templates Used in the Second Step PCR Assembly Reactions to Create Recombinant DNA for pLKTOK108

| Number | Template 1 | Template 2 | Concentration |
| --- | --- | --- | --- |
| 2A | Extracellular GCC | Mouse Ig2G2a-FcRmutII | 10 uM (2.5 ul each) |
| 2B | Extracellular GCC | Mouse IgG2a-FcRmutII | 30 uM (7.5 ul each) |

TABLE 11

Reaction Protocol Used in the Second Step PCR Assembly Reactions to Create Recombinant DNA for pLKTOK108

| Reaction Mixture | Machine Settings |
| --- | --- |
| 2.5 or 7.5 uL each DNA | 8 cycles |
| 10 uL 10× PCR buffer | 94° C.-1 minute |
| 3 uL MgCl$_2$ | 30 sec ramp |
| 2 uL dNTP | 72° C.-2 minutes |
| 79.5 or 69.5 uL H$_2$O | 30 sec ramp |
| 0.5 uL Taq | |

The third PCR reaction used the templates and primers described in Table 12 and Table 8 with the protocol described in Table 13 below to create the complete fragments. These DNA fragments were isolated from a 0.7% agarose gel using a Qiagen Gel Purification kit (Appendix F), and a thiamine adenosine (TA) overhang TOPO® TA Cloning Kit (Appendix F). Unique clones were isolated and DNA purified using Qiagen's DNA miniprep kit (Appendix F). The DNA was sequenced with the primers M13f, M13r and pSMUCH2 to identify those with the desired sequence. The intermediate TOPO clone TOK108-15 contained the desired recombinant DNA sequence.

TABLE 12

Templates Used in the Third Step PCR Assembly Reactions to Create Recombinant DNA for pLKTOK108

| Number | Product | Template | Primer 1 | Primer 2 | Size |
| --- | --- | --- | --- | --- | --- |
| 3A | TOK 108 Insert | Reaction 2A (5 ul) | pGCCFC5 | pMICOS-4 | 2028 bp |
| 3B | TOK 108 Insert | Reaction 2B (5 ul) | pGCCFC5 | pMICOS-4 | 2028 bp |

TABLE 13

Reaction Protocol Used in the Third Step PCR Assembly Reaction to Create Recombinant DNA for pLKTOK108

| Reaction Mixture | Machine settings |
| --- | --- |
| 5 uL PCR Reaction 2A or 2B | 94° C.-2 minutes |
| 0.2 uL 200 mM Primer 1 | |
| 0.2 uL 200 mM Primer 2 | 30 cycles |
| 10 uL 10× PCR buffer | 94° C.-1 minute |
| 3 uL 50 mM MgCl2 | 55° C.-30 seconds |
| 2 uL 10 mM dNTP mix | 72° C.-2 minutes |
| 79.5 uL H2O | |
| 0.5 uL Tac polymerase | 72° C.-10 minutes |

To create the expression vector pLKTOK4, pcDNA3.1™ was used as a backbone vector. It contains the neomycin (NEO) gene for resistance to G-418 (Geneticin®) to allow for easy selection under research conditions. The SpeI restriction site was eliminated from pcDNA™3.1 by site-directed mutagenesis. The EF-1α promoter from plasmid pcDEF3 (originally pEF-BOS[4]) was inserted into pcDNA™3.1, thus eliminating the CMV promoter. A circular map for the pLKTOK4 expression vector is depicted in FIG. 1.

Cloning was performed on the final PCR products using a TOPO® TA Cloning kit. After digestion with BamHI and XbaI restriction enzymes, the desired fragment from the TOPO clone was ligated to the expression vector pLKTOK4 that was also digested with BamHI and XbaI. The ligation reaction was used to transform K12 chemically competent E. coli cells and then selected on Luria broth (LB)/ampicillin agar plates. Plasmids from individual E. Coli clones were isolated using QIAGEN's DNA miniprep kit and sequenced with the primers SP6 (SEQ ID NO: 55), EF5S (SEQ ID NO: 54) and pSMUCH2 (SEQ ID NO: 53).

A clone determined to contain the desired recombinant DNA by DNA sequencing and used to make a large quantity of pure plasmid DNA using a QIAGEN Maxiprep kit. This maxiprep DNA was used for transfection into dihydrofolate reductase-deficient Chinese hamster ovary (CHO-DG44) cells.

A serum-free, suspension adapted CHO-DG44 cell line, called S1-CHO-DG44, was used for developing pLKTOK108 production cell lines. Briefly, transfections were done using a Nucleofector® device from Amaxa Biosystems and Nucleofection® kit V using either non-linearized, circular DNA or linearized plasmid DNA treated with Pvu 1 restriction enzyme. Transfected cells were maintained in IS-CHO-V-GS growth media for 48 hours before exchanging into G-418 selection media. The live, transfected cells were fed with fresh G-418 selection media and maintained in culture until confluence (~10 to 14 days). The pLKTOK108 productivity of each transfection pool was assessed using a mouse IgG2a ELISA assay and the cells expanded for making frozen cell banks. The transfection pool with the highest productivity by mouse IgG2a ELISA was identified for limited dilution cloning where cells were plated into 5×96-well tissue culture plates in G-418 Selection Medium (approximately 1 cell in every other well). The 96-well plates were incubated in a 37° C. incubator with 5% CO$_2$ for 2 weeks without feeding. Fifty µL of supernatant from each well that had a single colony was transferred directly into a 96-well assay plate to perform the mouse IgG2a ELISA assay. Twenty three clones with high productivity were identified and expanded sequentially through 24-well cell culture plates and then 6-well cell culture plates. The antibody titer of the supernatant from these clones was measured at 3 different dilutions in the mouse IgG2a ELISA assay.

The best 6 clones based on the mouse IgG2a titer were expanded in G-418 Selection Medium for making frozen cell banks and were adapted to serum-free, suspension Sigma #21 medium. The cell density and viability were determined using the Cedex Automated Cell Culture analyzer, and the protein concentration in the supernatant was measured using the mouse IgG2a ELISA assay. Once the cells reached logarithmic growth phase, they were harvested and frozen at −80° C. overnight and then transferred to a liquid nitrogen cryochamber for storage.

To produce the fusion protein, cells were thawed and plated, and subsequently serially expanded into larger T-flasks and then into shaker flasks at starting densities of $3.0 \times 10^5$ cells/mL and incubated in a humidified incubator set at 37° C., with 5% $CO_2$ in an orbital shaker set at 105 rpm. The final cultures were fed with 10% volume of the Sigma #21 Special Feed Medium on Days 4 and 7, and 5% volume on Day 10. Sigma #21 Feed Medium consists of Sigma #21 Medium supplemented with 40 g/L glucose, 10 g/L L-glutamine, 10 g/L yeast extract, and 10 g/L soy peptone. The shake culture was harvested by centrifugation. The supernatant containing secreted pLKTOK108 protein was filtered through a 0.2-μm low protein binding polyethersulfone (PES) membrane filter unit, with the crude pLKTOK108-containing filtrate ready for purification or stored at −80° C. for future purification.

Initial purification involved circulating filtered supernatants containing pLKTOK108 over Protein A Sepharose column at approximately 4° C. The resin was then washed with PBS pH7.4, and the protein eluted with 0.1M glycine in PBS at pH 3.0 and neutralized with 1M sodium phosphate at pH 6.5. The neutralized eluate was concentrated using a Vivaspin concentrator with a molecular weight cut-off (MWCO) of 30 kDa and loaded onto a Superdex 200 size-exclusion chromatography (SEC) column (Appendix G) that was pre-equilibrated with PBS pH 7.4 buffer in order to separate out aggregates of this protein. Purified pLKTOK108 protein elutes as a single peak, with purity confirmed on SDS-PAGE and Coomassie staining. Fractions containing the hGCC(ECD)/mIgG2a Fc homodimers were pooled. After the concentration of the pooled material was determined by UV absorbance at 280 nm on a NanoDrop™ ND1000 spectrophotometer, the purified pLKTOK108 protein was aliquoted and stored at −80° C.

Example 2

Generation of Rabbit mAbs by Protein Immunization

Rabbit monoclonal antibodies against the hGCC(ECD)-mIgG2a RcRbr-mutII fusion protein (pLKTOK108) were generated using the RabMAb® service provided by Epitomics (Burlingame, Calif.). For the purposes of MAb generation, the hGCC(ECD)-mIgG2a RcRbr-mutII fusion protein (pLKTOK108) fusion protein is referred to herein as MIL-44.

Three rabbits (ML1009, ML1010 and ML1011) were immunized with MIL-44 using conventional immunization techniques. The serum titer against MIL-44 and a non-GCC counterscreen antigen (hMadCAM-mFc) was evaluated using test bleeds. Booster immunizations were given subsequent to the initial immunizations. The rabbit with the highest serum titer, rabbit ML1010, was chosen as a candidate for splenectomy and monoclonal fusion using Epitomics' proprietary fusion partner cell line and methods.

On two separate days (Day 1 and Day 2), two hundred million lymphocyte cells were fused with 100 million fusion partner cells and plated on 20× 96-well plates, respectively. The plates were kept in tissue culture incubators under standard conditions. Cell growth was examined 2-3 weeks after fusion and fusion efficiency computed using the number of wells with growth divided by the total number of wells examined. The fusion efficiency for the fusion on Day 1 was measured at 72% fusion efficiency, whereas the fusion efficiency on Day 2 was 79%. A minimum of two plates were examined for each fusion as follows:

All 40 plates were screened using standard ELISA methods with plates coated with 50 ng of MIL-44/well. A bleed of ML1010 at 1:10K dilution was used as a positive control. 151 clones having an O.D. greater than 0.5 were considered putatively positive and were further expanded into a 24-well plate.

A subsequent confirmatory screen was performed by ELISA using plates coated with 50 ng of MIL-44 or 50 ng of hMadCAM-mFc/well. 143 clones were confirmed positive against MIL-44 and among them 72 were identified as MIL-44 specific, i.e., they were negative against hMadCAM-mFc protein.

Following the multiclone supernatant evaluation, several of the MIL-44 specific multiclones were sub-cloned: including multiclone #148 and #67. Subcloning was done using limited cell dilution method. Several subclone supernatatants were screened by ELISA. The hybridoma cells for subclones #148-2 and #67-4 were selected for freezing/banking and for further screening and analysis as a GCC detection reagent in an immunohistochemistry (IHC) assay, as described in Example 3.

The MIL-44-148-2 and MIL-44-67-4 antibodies were also cloned into pcDNA3.1+ neo (Invitrogen) for production by transient transfection in mammalian cells and for sequencing. The nucleic acid and amino acid sequences for the heavy and light chains for MIL-44-148-2 and MIL-44-67-4 antibodies are provided below. The signal sequence in each IgG chain is shown italicized; the variable region in each IgG chain is shown in bold font; the CDR's are shown underlined.

```
MIL-44-148-2 H2 Nucleic Acid Sequence                           (SEQ ID NO: 4)
ATGGAGACTGGGCTGCGCTGGCTTCTCCTGGTCGCTGTGCTCAAAGGTGTCCAGTGT

CAGTCAGTGAAGGAGTCCGGGGGAGGCCTCTTCAAGCCAACGGATACCCTGACACTCACCTGCA

CCGTCTCTGGATTCTCCCTCAGTAGTCATAGAATGAACTGGGTCCGCCAGACTCCAGGGAAGGG

GCTGGAATGGATCGCAATCATTACTCATAATAGTATCACATACTACGCGAGCTGGGCGAAAAGC

CGATCCACCATCACCAGAAACACCAGCGAGAACACGGTGACTCTGAAAATGACCAGTCTGACAG

CCGCGGACACGGCCACTTATTTCTGTGCCAGAGAGGATAGTATGGGGTATTATTTTGACTTGTG

GGGCCCAGGCACCCTGGTCACCATCTCCTCA
```

-continued

```
GGGCAACCTAAGGCTCCATCAGTCTTCCCACTGGCCCCCTGCTGCGGGGACACACCCAGCTCCA

CGGTGACCCTGGGCTGCCTGGTCAAAGGGTACCTCCCGGAGCCAGTGACCGTGACCTGGAACTC

GGGCACCCTCACCAATGGGGTACGCACCTTCCCGTCCGTCCGGCAGTCCTCAGGCCTCTACTCG

CTGAGCAGCGTGGTGAGCGTGACCTCAAGCAGCCAGCCCGTCACCTGCAACGTGGCCCACCCAG

CCACCAACACCAAAGTGGACAAGACCGTTGCGCCCTCGACATGCAGCAAGCCCACGTGCCCACC

CCCTGAACTCCTGGGGGGACCGTCTGTCTTCATCTTCCCCCCAAAACCCAAGGACACCCTCATG

ATCTCACGCACCCCCGAGGTCACATGCGTGGTGGTGGACGTGAGCCAGGATGACCCCGAGGTGC

AGTTCACATGGTACATAAACAACGAGCAGGTGCGCACCGCCCGGCCGCCGCTACGGGAGCAGCA

GTTCAACAGCACGATCCGCGTGGTCAGCACCCTCCCCATCGCGCACCAGGACTGGCTGAGGGGC

AAGGAGTTCAAGTGCAAAGTCCACAACAAGGCACTCCCGGCCCCCATCGAGAAAACCATCTCCA

AAGCCAGAGGGCAGCCCCTGGAGCCGAAGGTCTACACCATGGGCCCTCCCCGGGAGGAGCTGAG

CAGCAGGTCGGTCAGCCTGACCTGCATGATCAACGGCTTCTACCCTTCCGACATCTCGGTGGAG

TGGGAGAAGAACGGGAAGGCAGAGGACAACTACAAGACCACGCCGGCCGTGCTGGACAGCGACG

GCTCCTACTTCCTCTACAGCAAGCTCTCAGTGCCCACGAGTGAGTGGCAGCGGGGCGACGTCTT

CACCTGCTCCGTGATGCACGAGGCCTTGCACAACCACTACACGCAGAAGTCCATCTCCCGCTCT

CCGGGTAAATGA
```

```
MIL-44-148-2 H2 Amino Acid Sequence           (SEQ ID NO: 42)
METGLRWLLLVAVLKGVQCQSVKESGGGLFKPTDTLTLTCTVSGFSLSSHRMNWVRQTPGKGLE

WIAIITHNSITYYASWAKSRSTITRNTSENTVTLKMTSLTAADTATYFCAREDSMGYYFDLWGP

GTLVTISS

GQPKAPSVFPLAPCCGDTPSSTVTLGCLVKGYLPEPVTVTWNSGTLTNGVRTFPSVRQSSGLYS

LSSVVSVTSSSQPVTCNVAHPATNTKVDKTVAPSTCSKPTCPPPELLGGPSVFIFPPKPKDTLM

ISRTPEVTCVVVDVSQDDPEVQFTWYINNEQVRTARPPLREQQFNSTIRVVSTLPIAHQDWLRG

KEFKCKVHNKALPAPIEKTISKARGQPLEPKVYTMGPPREELSSRSVSLTCMINGFYPSDISVE

WEKNGKAEDNYKTTPAVLDSDGSYFLYSKLSVPTSEWQRGDVFTCSVMHEALHNHYTQKSISRS

PGK
```

```
MIL-44-148-2 L5 Nucleic Acid Sequence         (SEQ ID NO: 5)
ATGGACACGAGGGCCCCCACTCAGCTGCTGGGGCTCCTGCTGCTCTGGCTCCCAGGTGCCAGAT

GTGCCTATGATATGACCCAGACTCCAGCCTCTGTGGAGGTAGCTGTGGGAGGCACAGTCACCAT

CAAGTGCCAGGCCAGTCAGAGCATTAGTAACTGGTTAGCCTGGTATCAGCAGAAACCAGGGCAG

TCTCCCAAGCCCCTGATCTACAGGGCATCCACTCTGGCATCTGGGGTCTCATCGCGGTTCAGAG

GCAGTGGATCTGGGACACAGTTCACTCTCACCATCAGTGGCGTGGAGTGTGCCGATGCTGCCAC

TTACTACTGTCAGCAGACTTATACTAATAATCATCTTGATAATGGTTTCGGCGGAGGGACCGAG

GTGGTGGTCAAA

GGTGATCCAGTTGCACCTACTGTCCTCATCTTCCCACCAGCTGCTGATCAGGTGGCAACTGGAA

CAGTCACCATCGTGTGTGTGGCGAATAAATACTTTCCCGATGTCACCGTCACCTGGGAGGTGGA

TGGCACCACCCAAACAACTGGCATCGAGAACAGTAAAACACCGCAGAATTCTGCAGATTGTACC
```

-continued

TACAACCTCAGCAGCACTCTGACACTGACCAGCACACAGTACAACAGCCACAAAGAGTACACCT

GCAGGGTGACCCAGGGCACGACCTCAGTCGTCCAGAGCTTCAATAGGGGTGACTGTTAG

MIL-44-148-2 L5 Amino Acid Sequence                (SEQ ID NO: 43)
*MDTRAPTQLLGLLLLWLPGARC*AYDMTQTPASVEVAVGGTVTIKCQASQSISNWLAWYQQKPGQ

SPKPLIYRASTLASGVSSRFRGSGSGTQFTLTISGVECADAATYYCQQTYTNNHLDNGFGGGTE

VVVK

GDPVAPTVLIFPPAADQVATGTVTIVCVANKYFPDVTVTWEVDGTTQTTGIENSKTPQNSADCT

YNLSSTLTLTSTQYNSHKEYTCRVTQGTTSVVQSFNRGDC

MIL-44-67-4 H2 Nucleic Acid Sequence               (SEQ ID NO: 6)
*ATGGAGACTGGGCTGCGCTGGCTTCTCCTGGTCGCTGTGCTCAAAGGTGTCCAGTGT*CAGTCGG

TGGAGGAGTCCGGGGGTCGCCTGGTCACGCCTGGGACACCCCTGACACTCACCTGCACAGCCTC

TGGATCCGACATCAGTAACTATGCAATATCCTGGGTCCGCCAGGCTCCAGGGAAGGGGCTGGAA

TTCATCGGATATATTAGTTATGGTAAAAGTATATACTACGCGAGCTGGGCGAAAGGCCGGTTCG

CCATCTCCAAAACCTCGTCGACCACGGTGGATCTGGAAATCACCAGTCCGACAACCGAGGACAC

GGCCACCTATTTTTGTGCCAGAGAGGATAGTGCTACTTATAGTCCTAACTTGTGGGGCCCAGGC

ACCCTGGTCACCGTCTCCTCA

GGGCAACCTAAGGCTCCATCAGTCTTCCCACTGGCCCCCTGCTGCGGGGACACACCCAGCTCCA

CGGTGACCCTGGGCTGCCTGGTCAAAGGGTACCTCCCGGAGCCAGTGACCGTGACCTGGAACTC

GGGCACCCTCACCAATGGGGTACGCACCTTCCCGTCCGTCCGGCAGTCCTCAGGCCTCTACTCG

CTGAGCAGCGTGGTGAGCGTGACCTCAAGCAGCCAGCCCGTCACCTGCAACGTGGCCCACCCAG

CCACCAACACCAAAGTGGACAAGACCGTTGCGCCCTCGACATGCAGCAAGCCCACGTGCCCACC

CCCTGAACTCCTGGGGGGACCGTCTGTCTTCATCTTCCCCCCAAAACCCAAGGACACCCTCATG

ATCTCACGCACCCCCGAGGTCACATGCGTGGTGGTGGACGTGAGCCAGGATGACCCCGAGGTGC

AGTTCACATGGTACATAAACAACGAGCAGGTGCGCACCGCCCGGCCGCCGCTACGGGAGCAGCA

GTTCAACAGCACGATCCGCGTGGTCAGCACCCTCCCCATCGCGCACCAGGACTGGCTGAGGGGC

AAGGAGTTCAAGTGCAAAGTCCACAACAAGGCACTCCCGGCCCCCATCGAGAAAACCATCTCCA

AAGCCAGAGGGCAGCCCCTGGAGCCGAAGGTCTACACCATGGGCCCTCCCCGGGAGGAGCTGAG

CAGCAGGTCGGTCAGCCTGACCTGCATGATCAACGGCTTCTACCCTTCCGACATCTCGGTGGAG

TGGGAGAAGAACGGGAAGGCAGAGGACAACTACAAGACCACGCCGGCCGTGCTGGACAGCGACG

GCTCCTACTTCCTCTACAGCAAGCTCTCAGTGCCCACGAGTGAGTGGCAGCGGGGCGACGTCTT

CACCTGCTCCGTGATGCACGAGGCCTTGCACAACCACTACACGCAGAAGTCCATCTCCCGCTCT

CCGGGTAAATGA

MIL-44-67-4 H2 Amino Acid Sequence                 (SEQ ID NO: 44)
*METGLRWLLLVAVLKGVQC*QSVEESGGRLVTPGTPLTLTCTASGSDISNYAISWVRQAPGKGLE

FIGYISYGKSIYYASWAKGRFAISKTSSTTVDLEITSPTTEDTATYFCAREDSATYSPNLWGPG

TLVTVSS

-continued
```
GQPKAPSVFPLAPCCGDTPSSTVTLGCLVKGYLPEPVTVTWNSGTLTNGVRTFPSVRQSSGLYS

LSSVVSVTSSSQPVTCNVAHPATNTKVDKTVAPSTCSKPTCPPPELLGGPSVFIFPPKPKDTLM

ISRTPEVTCVVVDVSQDDPEVQFTWYINNEQVRTARPPLREQQFNSTIRVVSTLPIAHQDWLRG

KEFKCKVHNKALPAPIEKTISKARGQPLEPKVYTMGPPREELSSRSVSLTCMINGFYPSDISVE

WEKNGKAEDNYKTTPAVLDSDGSYFLYSKLSVPTSEWQRGDVFTCSVMHEALHNHYTQKSISRS

PGK

MIL-44-67-4 L4 Nucleic Acid Sequence                    (SEQ ID NO: 7)
ATGGACACGAGGGCCCCCACTCAGCTGCTGGGGCTCCTGCTGCTCTGGCTCCCAGGTGCCAGAT

GTGCCTATGATATGACCCAGACTCCAGCCTCTGTGGAGGTAGCTGTGGGAGGCACAGTCACCAT

CAAGTGCCAGGCCAGTCAGAGTATTAACACCTACTTAGCCTGGTATCAGCAGAAACCAGGGCAG

CGTCCCAAGCTCCTGATCTACAGGGCATCCACTCTGGCATCTGGGGTCTCATCGCGGTTCAAAG

GCAGTGGATCTGGGACAGAGTTCACTCTCACCATCAGCGGCGTGGAGTGTGCCGATGCTGCCAC

TTACTACTGTCAACAGGGTTATAGTTATAATAATCTTGATCGTGCTTTCGGCGGAGGGACCGAG

GTGGTGGTCACA

GGTGATCCAGTTGCACCTACTGTCCTCATCTTCCCACCAGCTGCTGATCAGGTGGCAACTGGAA

CAGTCACCATCGTGTGTGTGGCGAATAAATACTTTCCCGATGTCACCGTCACCTGGGAGGTGGA

TGGCACCACCCAAACAACTGGCATCGAGAACAGTAAAACACCGCAGAATTCTGCAGATTGTACC

TACAACCTCAGCAGCACTCTGACACTGACCAGCACACAGTACAACAGCCACAAAGAGTACACCT

GCAAGGTGACCCAGGGCACGACCTCAGTCGTCCAGAGCTTCAATAGGGGTGACTGTTAG

MIL-44-67-4 L4 Amino Acid Sequence                    (SEQ ID NO: 45)
MDTRAPTQLLGLLLLWLPGARCAYDMTQTPASVEVAVGGTVTIKCQASQSINTYLAWYQQKPGQ

RPKLLIYRASTLASGVSSRFKGSGSGTEFTLTISGVECADAATYYCQQGYSYNNLDRAFGGGTE

VVVT

GDPVAPTVLIFPPAADQVATGTVTIVCVANKYFPDVTVTWEVDGTTQTTGIENSKTPQNSADCT

YNLSSTLTLTSTQYNSHKEYTCKVTQGTTSVVQSFNRGDC
```

Example 3

Immunohistochemistry Using Anti-GCC Antibodies

Detection of GCC Expression in Human Tumor Xenograft Models

An IHC assay using the MIL-44-148-2 antibody was developed to evaluate GCC expression in HEK293-GCC xenograft tumors and several primary human tumor xenografts (PHTX) derived from mCRC patient samples in female SCID mice.

GCC protein levels in Formalin-Fixed, Paraffin-Embedded (FFPE) tissues were assessed on 5 μm thick sections and incubated with MIL-44-148-2 antibody (3.5 μg/mL) for 1 hour on the Ventana Medical Systems (Tucson, Ariz.) Discovery XT® automated stainer. Antibodies were biotinylated with a rabbit anti-goat secondary antibody (Vector Laboratories) and developed with the 3,3'-diaminobexidine (DAB) substrate map system (Ventana Medical Systems). Slides were counterstained with hematoxylin and imaged using the Aperio whole slide scanning system.

GCC levels differed significantly among these tumors with H-scores (scoring system described below) ranging from 4+ in HEK293-GCC tumor xenografts, and from 1+, 1-2+, 2+, 2-3+, and 4+ in various PHTX tumor xenografts. In general, in tumors with moderate/well differentiated tumor cells that maintained a polarized epithelial structure, GCC was concentrated on the luminal side of the tumor tissue.

Detection of GCC Expression in Colon Samples and Tumor Microarrays

The MIL-44-148-2 and MIL-44-67-4 antibodies described herein were also screened as a GCC detection reagent in an IHC protocol described above using the above-reference primary human tumor xenografts (PHTX), HT29 and HEK293 GCC transfected cell pellets, in addition to malignant and benign human colon samples (FFPE and tumor microarrays (TMAs)).

HT-29 and HEK293 GCC transfected cell pellets stained as expected. The PHTXs demonstrated a wide range of staining intensities with the MIL-44-148-2 and MIL-44-67-4 clones. Both MIL-44-148-2 and MIL-44-67-4 stained positive in well or moderately differentiated colon carcinoma in situ or metastasis. Poorly differentiated tumors stained less intensely. Normal colon tissue demonstrated positive apical staining using antibodies produced by both the MIL-44-148-2 and MIL-44-67-4 subclones.

Antibodies from both the MIL-44-148-2 and MIL-44-67-4 subclones provided intense and specific staining without any non-specific staining in the parental cell line. However, MIL-44-148-2 demonstrated an overall higher sensitivity and specificity than MIL-44-67-4 in IHC. While MIL-44-67-4 demonstrated a better dynamic range than MIL-44-148-2 in cell pellets, MIL-44-148-2 demonstrated a superior dynamic range over that of MIL-44-67-4 in TMAs.

Based on the results of the initial IHC experiments described above, the MIL-44-148-2 subclone was selected for the development and validation of an automated protocol equivalent to the IHC protocol described above using a Tek-Mate automated stainer. The automated IHC assay is a useful tool for screening cancer patients for GCC expressing tumors as a clinical trial enrollment criteria for a cancer therapeutic directed towards GCC.

The IHC protocol shown in Table 14 was developed for detection of GCC in FFPE human cells and tissues, and approximately 53 colorectal tumors and 20 normal colon tissues, as well as 2 colon cancer TMAs (purchased from US Biomax) were screened for GCC expression. These tumors covered a range of tumor grades as well as colon cancer metastatic tissues.

Four-micron sections were prepared from the various tissue samples. Tissue sections were dewaxed through 4, 5-minute changes of xylene followed by a graded alcohol series to distilled water. Steam heat induced epitope recovery (SHIER) was used with SHIER2 solution for 20 minutes in the capillary gap in the upper chamber of a Black and Decker Steamer.

TABLE 14

IHC Procedure

| TechMate Steps | UltraVision Detection (UV) |
|---|---|
| 1. | UltraVision Block-15 minutes |
| 2. | Primary Antibody Incubation-Overnight |
| 3. | Primary Antibody Enhancer-25 minutes |
| 4. | Hydrogen peroxide block-3 × 2.5 minutes each |
| 5. | Polymer Detection-25 minutes |
| 6. | DAB Chromogen-3 × 5.0 minutes each |
| 7. | Hematoxylin Counter Stain-1 minute |

The above protocol used an overnight antibody incubation of MIL-44-148-2 at 1.0 µg/ml with a non-biotin based peroxidase detection (Ultravision kit from Thermo/Lab Vision) and DAB as chromogen. This procedure was completely automated using the TechMate 500 or TechMate 1000 (Roche Diagnostics). After staining, slides were dehydrated through an alcohol series to absolute ethanol followed by xylene rinses. Slides were permanently coverslipped with glass coverslips and CytoSeal. Slides were examined under a microscope to assess staining. Positive staining is indicated by the presence of a brown (DAB-HRP) reaction product. Hematoxylin counterstain provides a blue nuclear stain to assess cell and tissue morphology.

Upon evaluating the GCC staining, it was determined that an H-score approach would be the best approach for quantitating GCC expression. The H-score approach provides optimal data resolution for determining variation in intensity and tumor percentage of staining within and among tumor types. It also provides a good tool for determining thresholds for positive staining. In this method, the percentage of cells (0-100) within a tumor with staining intensities ranging from 0-3+ are provided. With the instant method, scores with intensities of 0, 0.5, 1, 2 and 3 were provided. Depending on the marker, 0.5 staining can be scored as positive or negative, and reflects light but perceptible staining for the marker. To obtain an H-score, the percentage of tumor cells are multiplied by each intensity and added together. The maximum H-score is 300 if 100% of tumor cells label with 3+ intensity.

Initially, as a control, the total H-score alone was not be used to compare samples, but evaluated in addition to a review of the break-down of the percentage of cells at each intensity. For example, a score of 90 could represent 90% of tumor cells staining with 1+ intensity or 30% of cells with 3+ intensity. These samples have the same H-score but very different GCC expression. The percentage of cells to be scored at each intensity can vary, but are normally scored in increments of 10%; however, a small percentage of scoring of a single component can be estimated at 1% and 5% as well in order to demonstrate that some level of staining is present. For GCC, apical staining may be considered for evaluating at low level increments, such as 1 and 5%.

Two different sub-cellular localizations were scored for GCC using the H-score approach. These include cytoplasmic staining and apical associated staining. The cytoplasmic staining pattern was generally observed as diffuse throughout the cytoplasm of tumor cells. However, in some cases there were variations of the cytoplasmic staining, which included intense globular staining or punctate, coarse granular staining. Intense globular staining was scored as 3+ cytoplasmic staining. The punctate staining was associated with apical staining and was not given a separate score for this type of cytoplasmic staining (n=4 samples for punctate staining). GCC apical staining was observed when lumen were present. Other GCC staining patterns observed included membrane-like, non-lumen staining (one case) and extra-cellular staining present in tumor lumen. In normal colon tissues, staining was generally apical along with diffuse cytoplasmic staining.

Overall, staining in a normal colon samples illustrated that GCC is anatomically privileged, being expressed on the apical surface. GCC was expressed on more than 95% of tumor samples and, in contrast to normal tissue, demonstrated diffuse cytoplasmic staining in some cases. Strong focal GCC staining in human CRC liver metastasis samples was also seen.

Tables 15A shows cytoplasmic and apical H-score staining results for normal and tumor tissues that were screened. Data shown in Table 15 is broken-out according to sample origin (in-house (denoted as MLNM), TMAs (denoted as BIOMAX), and CRO (denoted as QualTek)) and tumor grade. Summary data of positivity is provided when using thresholds of 0.5 and 1.0+ staining intensity. A total of 173 tumor samples were scored. When using a 0.5+ cut-off for positive staining intensity for either cytoplasmic or apical staining, 95% of tumors are considered positive. When using a 1.0+ cut-off, 92% of samples are considered positive.

The source of tissues shows variation in the percentage of positive tumors cells as well as the H-scores. For 1+ staining positivity threshold, the range is from 84% (CRO tumor MTB samples) to 100% (in-house samples or CRO single tissue samples—note the smaller number of samples in these groups). The in-house tumor tissues showed a very high apical H-score of 253 (n=9 samples). There were also differences in the scoring results of the 2 TMAs. US Biomax TMA C0992 stained stronger than C0701. Without intending to be bound by any theory, the difference in the TMAs may be due to a difference with fixation with the source of tissues or one block could have been cut more recently than the other.

The stability of the antigen in a cut section and the freshness of the cut samples were considered. Samples tested the instant study included samples that were cut and stored and samples that were cut fresh, indicating a need to further research the stability of the tissue samples over time.

Some differences were observed in GCC positivity and tumor grade (see Table 15B), with greater positive staining associated with well differentiated tumors vs. poorly differentiated tumors (six tumors from US Biomax did not include a grade). Grade 1 tumors (n=20) showed 100% positivity; Grade 2 tumors (n=95) labeled with 98% of positive cases; and grade 3 tumors (n=44) labeled at a positivity rate of 88%. Poorly differentiated tumors generally lack lumen, which may account for some of this decrease in staining due to a lack of apical staining. This percent positivity was based on a 0.5+ staining intensity threshold. Seven of 7 distant mets were positive (from in-house and CRO tissues). Metastatic tumors from the US Biomax TMA were listed as mets to lymph nodes.

Overall, GCC stains a very high percentage of colon tumors and normal colon tissues regardless of the source of the tissue or the tumor grade.

TABLE 15A

Summary of colon cancer staining by sample source

| Colon CA Samples | Total Colon CA Samples | No. Sample Positive | | | | Mean H-Score 0-300 | |
|---|---|---|---|---|---|---|---|
| | | 0.5+ & Greater | | 1.0+ & Greater | | | |
| | | No. | % | No. | % | Cyto | Apical |
| MLNM Samples | 9 | 9 | 100% | 9 | 100% | 83 | 253 |
| QualTek Single Samples | 4 | 4 | 100% | 4 | 100% | 69 | 98 |
| QualTek Colon CA MTBS | 43 | 39 | 91% | 36 | 84% | 66 | 118 |
| BIOMAX C0992 Array | 65 | 63 | 97% | 63 | 97% | 144 | 164 |
| BIOMAX C0701 Array | 52 | 49 | 94% | 48 | 92% | 98 | 118 |
| Total | 173 | 164 | 95% | 160 | 92% | 102 | 138 |

TABLE 15B

Summary of colon cancer staining by tumor grade

| Colon Samples | No. Positive | Total Samples | % |
|---|---|---|---|
| Normal | 57 | 58 | 98% |
| Grade 1 | 25 | 20 | 100% |
| Grade 2 | 95 | 97 | 98% |
| Grade 3 | 44 | 50 | 88% |
| Total | 216 | 225 | 96% |

Intra-assay precision of the GCC IHC assay was evaluated within one run utilizing 5 replicates each from three cell pellets and 14 different colon carcinoma tissues. Cell pellets were prepared on separate slides. Colon tumor samples were included in two different multi-tumor blocks. These tissues were scored for GCC IHC reactivity.

Precision staining of cell pellets: Near identical staining was observed in all of the 5 intra-run replicates of the 3 cell pellets.

Precision staining of colon tumor samples: Very similar to near identical staining was observed among the 5 intra-run replicates of the 14 colon tumor samples. Samples were scored by a certified pathologist using the H-score approach as described previously. The standard deviation demonstrated that in all cases the variance was minimal, thus demonstrating good precision of staining within the same run. Overall, there was very consistent intra-run GCC IHC staining of the cell pellet and colon carcinoma samples tested.

Between-run assay variability and variability due to different operators was evaluated in 5 separate GCC IHC staining runs. Four runs were performed on different days by one operator and a second operator performed the fifth run. Staining included testing of the same tissues in the precision testing described above.

Reproducibility staining of cell pellets: Near identical staining as observed in all of the 5 inter-run replicates of the 3 cell pellets.

Reproducibility staining of colon tumor samples: Very similar to near identical staining was observed among the 5 inter-run replicates of the 14 colon tumor samples. Samples were scored by a certified pathologist using the H-score approach as described previously. The standard deviation demonstrated that in all cases the variance as minimal, thus demonstrating good reproducibility of staining from day to day and with a different operator. Overall, there was very consistent inter-run and inter-operator GCC IHC staining of the cell pellet and colon carcinoma samples tested.

Specificity of the GCC IHC assay was evaluated by testing a panel of normal human tissues. These normal human tissues included 30 different tissue types: adrenal, bladder, bone marrow, breast, cerebral cortex, cervix, fallopian tube, heart, kidney, liver, lung, lymph node, nerve, ovary, pancreas, parotid (salivary gland), pituitary, placenta, prostate, skeletal muscle, skin, spinal cord, spleen, stomach, testis, thymus, thyroid, tonsil, ureter, and uterus. For each tissue type, at least 3 unique specimens were stained and evaluated for GCC immunoreactivity.

Overall, the GCC IHC assay using the MIL-44-148-2 antibody was shown by the IHC assay described herein to be very specific for colon tumor samples compared to normal tissue staining, particularly for apical staining. Apical staining was only detected in 2 of the stomach samples; however, this staining was also observed in the negative control. Cytoplasmic staining, generally light, was observed in several tissue types, including ovarian follicle (1 of 3 samples), skin (follicle and dermis, 2 of 3 samples), stomach parietal cells (2 of 3 samples), prostate glandular epithelium (light in 3 of 3 cases), pituitary (2 of 3 cases), uterus epithelium (3 of 3 cases), fallopian tube epithelium (2 of 3 cases), placenta trophoblast (light in 2 of 3 cases) and lung (endothelium in 3 of 3 cases and bronchiole epithelium in 1 of 3 cases). The strongest cytoplasmic staining (2+) was present in one case of fallopian tube and one case of pituitary. In both cases there was lighter staining in the same compartments in the negative control. Plasma cells were positive in a number of tissues, including spleen, tonsil and lymph node. Histiocytes were positive in spleen, lung and lymph node. Stromal staining was present in testis (2 of 3 cases), uterus (3 of 3 cases) and ovary (1 of 3 cases). Extracellular staining of blood vessels was widely observed and appears to be non-specific binding of serum.

The GCC assay, using the rabbit monoclonal antibody, MIL-44-148-2, on the TechMate staining platform shows consistent inter and intra-run staining of tumors and control cell pellets. The GCC assay appears to be highly sensitive in colon carcinoma as it stains the vast majority of colon tumor samples tested. The GCC assay also appears to be much more specific for colon tumors compared to normal tissues. GCC expression observed in many colon tumors is far stronger than any staining observed in a 30 tissue normal panel with at least 3 replicates of each tissue type. No specific apical GCC staining was detected in any of the normal tissues, whereas apical staining is common in the majority of GCC samples. Only cytoplasmic staining is observed in some normal tissue types and this staining is generally light. The MIL-44-148-2 antibody appears to be a reproducible, sensitive and relatively specific IHC marker for staining formalin-fixed, paraffin-embedded (FFPE) colon tumors.

While this invention has been shown and described with references to provided embodiments thereof, it will be understood by those skilled in the art that various changes in form and details may be made therein without departing from the scope of the invention encompassed by the appended claims.

What is claimed is:

1. Isolated nucleic acid sequences that encode:
   a) an anti-GCC antibody molecule, comprising
      (i) a light chain variable region (SEQ ID NO: 13) and a heavy chain variable region (SEQ ID NO: 11) of antibody MIL-44-148-2; or
      (ii) a light chain variable region (SEQ ID NO: 17) and a heavy chain variable region (SEQ ID NO: 15) of antibody MIL-44-67-4; or
   b) an anti-GCC antibody molecule, comprising
      (i) light chain CDR1 (SEQ ID NO: 27), CDR2 (SEQ ID NO: 28), and CDR3 (SEQ ID NO: 29), and heavy chain CDR1 (SEQ ID NO: 21), CDR2 (SEQ ID NO: 22), and CDR3 (SEQ ID NO: 23) of antibody MIL-44-148-2, or
      (ii) light chain CDR1 (SEQ ID NO: 39), CDR2 (SEQ ID NO: 40), and CDR3 (SEQ ID NO: 41) and heavy chain CDR1 (SEQ ID NO: 33), CDR2 (SEQ ID NO: 34), and CDR3 (SEQ ID NO: 35) of antibody MIL-44-67-4.

2. A cell comprising the isolated nucleic acid sequences of claim 1.

3. A method of producing an antibody molecule comprising culturing the cell of claim 2 under conditions that allow production of an antibody molecule, thereby producing:
   a) an anti-GCC antibody molecule, comprising
      (i) a light chain variable region (SEQ ID NO: 13) and a heavy chain variable region (SEQ ID NO: 11) of antibody MIL-44-148-2; or
      (ii) a light chain variable region (SEQ ID NO: 17) and a heavy chain variable region (SEQ ID NO: 15) of antibody MIL-44-67-4; or
   b) an anti-GCC antibody molecule, comprising
      (i) light chain CDR1 (SEQ ID NO: 27), CDR2 (SEQ ID NO: 28), and CDR3 (SEQ ID NO: 29), and heavy chain CDR1 (SEQ ID NO: 21), CDR2 (SEQ ID NO: 22), and CDR3 (SEQ ID NO: 23) of antibody MIL-44-148-2, or
      (ii) light chain CDR1 (SEQ ID NO: 39), CDR2 (SEQ ID NO: 40), and CDR3 (SEQ ID NO: 41) and heavy chain CDR1 (SEQ ID NO: 33), CDR2 (SEQ ID NO: 34), and CDR3 (SEQ ID NO: 35) of antibody MIL-44-67-4.

4. A vector comprising one or both of the light chain and heavy chain of:
   a) an anti-GCC body molecule, comprising
      (i) a light chain variable region (SEQ ID NO: 13) and a heavy chain variable region (SEQ ID NO: 11) of antibody MIL-44-148-2; or
      (ii) a light chain variable region (SEQ ID NO: 17) and a heavy chain variable region (SEQ ID NO: 15) of antibody MIL-44-67-4; or
   b) an anti-GCC antibody molecule, comprising
      (i) light chain CDR1 (SEQ ID NO: 27), CDR2 (SEQ ID NO: 28), and CDR3 (SEQ ID NO: 29), and heavy chain CDR1 (SEQ ID NO: 21), CDR2 (SEQ ID NO: 22), and CDR3 (SEQ ID NO: 23) of antibody MIL-44-148-2, or
      (ii) light chain CDR1 (SEQ ID NO: 39), CDR2 (SEQ ID NO: 40), and CDR3 (SEQ ID NO: 41) and heavy chain CDR1 (SEQ ID NO: 33), CDR2 (SEQ ID NO: 34), and CDR3 (SEQ ID NO: 35) of antibody MIL-44-67-4.

5. A method of detecting a GCC molecule comprising contacting the molecule with:
   a) an anti-GCC body molecule, comprising
      (i) a light chain variable region (SEQ ID NO: 13) and a heavy chain variable region (SEQ ID NO: 11) of antibody MIL-44-148-2; or
      (ii) a light chain variable region (SEQ ID NO: 17) and a heavy chain variable region (SEQ ID NO: 15) of antibody MIL-44-67-4; or
   b) an anti-GCC antibody molecule, comprising
      (i) light chain CDR1 (SEQ ID NO: 27), CDR2 (SEQ ID NO: 28), and CDR3 (SEQ ID NO: 29), and heavy chain CDR1 (SEQ ID NO: 21), CDR2 (SEQ ID NO: 22), and CDR3 (SEQ ID NO: 23) of antibody MIL-44-148-2, or
      (ii) light chain CDR1 (SEQ ID NO: 39), CDR2 (SEQ ID NO: 40), and CDR3 (SEQ ID NO: 41) and heavy chain CDR1 (SEQ ID NO: 33), CDR2 (SEQ ID NO: 34), and CDR3 (SEQ ID NO: 35) of antibody MIL-44-67-4.

6. The method of claim 5, wherein said method comprises an immunohistochemistry assay using a biological sample derived from a patient suspected of having a GCC expressing cancer.

7. The method of claim 6, wherein said biological sample is a tumor biopsy.

8. The method of claim 6, further comprising the step of quantifying GCC expression in said biological sample.

9. The method of claim 8, wherein said quantification of GCC expression comprises apical GCC expression, cytoplasmic GCC expression, or both.

10. The method of claim 8, wherein said quantification step comprises an H-score approach.

11. The method of claim 6, wherein said GCC expressing cancer is selected from the group consisting of: colorectal cancer, gastric cancer, esophageal cancer, pancreatic cancer, liver cancer, ovarian cancer, lung cancer, a gastrointestinal neuroendocrine tumor, and a bronchopulmonary neuroendocrine tumor.

12. A method of treating a patient having cancer characterized by GCC-expressing tumor cells, comprising:
    a. detecting GCC expression on a sample of tumor cells from the patient by contacting said sample with;
       (1) an anti-GCC antibody molecule, comprising
          (i) a light chain variable region (SEQ ID NO: 13) and a heavy chain variable region (SEQ ID NO: 11) of antibody MIL-44-145-2; or
          (ii) a light chain variable region (SEQ ID NO: 17) and a heavy chain variable region (SEQ ID NO: 15) of antibody MIL-44-67-4; or
       (2) an anti-GCC antibody molecule, comprising
          (i) light chain CDR1 (SEQ ID NO: 27), CDR2 (SEQ ID NO: 28), and CDR3 (SEQ ID NO: 29), and heavy chain CDR1 (SEQ ID NO: 21), CDR2 (SEQ ID NO: 22), and CDR3 (SEQ ID NO: 23) of antibody MIL-44-148-2, or
          (ii) light chain CDR1 (SEQ ID NO: 39), CDR2 (SEQ ID NO: 40), and CDR3 (SEQ ID NO: 41) and heavy chain CDR1 (SEQ ID NO: 33), CDR2 (SEQ ID NO: 34), and CDR3 (SEQ ID NO: 35) of antibody MIL-44-67-4; and
    b. administering a therapeutic anti-CGG antibody molecule conjugated to a toxin if the tumor cells express GCC on the cell surface.

* * * * *

UNITED STATES PATENT AND TRADEMARK OFFICE
CERTIFICATE OF CORRECTION

| | | |
|---|---|---|
| PATENT NO. | : 9,273,146 B1 | Page 1 of 1 |
| APPLICATION NO. | : 14/634438 | |
| DATED | : March 1, 2016 | |
| INVENTOR(S) | : Helen Frank et al. | |

It is certified that error appears in the above-identified patent and that said Letters Patent is hereby corrected as shown below:

Claims

Claim 4, col. 146, line 22, "a) an anti-GCC body molecule, comprising" should read -- "a) an anti-GCC antibody molecule, comprising"

Claim 5, col. 146, line 42, "a) an anti-GCC body molecule, comprising" should read -- "a) an anti-GCC antibody molecule, comprising"

Claim 5, col. 146, line 59, "44-67-4." should read -- "44-67-4; and determining if said antibody molecule binds to said GCC molecule."

Claim 6, col. 146, line 62, "derived from a patient suspected of having a GCC expressing" should read -- "derived from a patient suspected of having a GCC-expressing"

Claim 12, col. 147, line 19, "antibody MIL-44-145-2; or" should read -- "antibody MIL-44-148-2; or"

Claim 12, col. 148, line 16, "b. administering a therapeutic anti-CGG antibody mol-" should read -- "b. administering a therapeutic anti-GCC antibody mol-"

Signed and Sealed this
Twelfth Day of July, 2016

Michelle K. Lee
*Director of the United States Patent and Trademark Office*

SEQUENCE LISTING

```
<160> NUMBER OF SEQ ID NOS: 89

<210> SEQ ID NO 1
<211> LENGTH: 18
<212> TYPE: PRT
<213> ORGANISM: Escherichia coli

<400> SEQUENCE: 1

Asn Thr Phe Tyr Cys Cys Glu Leu Cys Cys Asn Pro Ala Cys Ala Gly
1               5                   10                  15

Cys Tyr

<210> SEQ ID NO 2
<211> LENGTH: 3360
<212> TYPE: DNA
<213> ORGANISM: Homo sapiens

<400> SEQUENCE: 2
gaccagagag aagcgtgggg aagagtgggc tgagggactc cactagaggc tgtccatctg      60
gattccctgc ctccctagga gcccaacaga gcaaagcaag tgggcacaag gagtatggtt     120
ctaacgtgat tggggtcatg aagacgttgc tgttggactt ggctttgtgg tcactgctct     180
tccagcccgg gtggctgtcc tttagttccc aggtgagtca gaactgccac aatggcagct     240
atgaaatcag cgtcctgatg atgggcaact cagcctttgc agagccctg aaaaacttgg      300 aagatgcggt gaatgagggg ctggaaatag tgagaggacg tctgcaaaat gctggcctaa     360
atgtgactgt gaacgctact ttcatgtatt cggatggtct gattcataac tcaggcgact     420
gccggagtag cacctgtgaa ggcctcgacc tactcaggaa aatttcaaat gcacaacgga     480
tgggctgtgt cctcataggg ccctcatgta catactccac cttccagatg taccttgaca     540
cagaattgag ctacccatg atctcagctg gaagttttgg attgtcatgt gactataaag      600
aaaccttaac caggctgatg tctccagcta gaaagttgat gtacttcttg gttaactttt     660
ggaaaaccaa cgatctgccc ttcaaaactt attcctggag cacttcgtat gtttacaaga     720
atggtacaga aactgaggac tgtttctggt accttaatgc tctggaggct agcgtttcct     780
atttctccca cgaactcggc tttaaggtgg tgttaagaca agataaggag tttcaggata     840
tcttaatgga ccacaacagg aaaagcaatg tgattattat gtgtggtggt ccagagttcc     900
tctacaagct gaagggtgac cgagcagtgg ctgaagacat tgtcattatt ctagtggatc     960
ttttcaatga ccagtacttt gaggacaatg tcacagcccc tgactatatg aaaaatgtcc    1020
ttgttctgac gctgtctcct gggaattccc ttctaaatag ctctttctcc aggaatctat    1080
caccaacaaa acgagacttt gctcttgcct atttgaatgg aatcctgctc tttggacata    1140
```

-continued

```
tgctgaagat atttcttgaa aatggagaaa atattaccac ccccaaattt gctcatgctt    1200
tcaggaatct cacttttgaa gggtatgacg gtccagtgac cttggatgac tgggggatg     1260 ttgacagtac catggtgctt ctgtatacct ctgtggacac caagaaatac aaggttcttt    1320
tgacctatga tacccacgta aataagacct atcctgtgga tatgagcccc acattcactt    1380
ggaagaactc taaacttcct aatgatatta caggccgggg ccctcagatc ctgatgattg    1440
cagtcttcac cctcactgga gctgtggtgc tgctcctgct cgtcgctctc ctgatgctca    1500
gaaaatatag aaaagattat gaacttcgtc agaaaaaatg gtcccacatt cctcctgaaa    1560
atatctttcc tctggagacc aatgagacca atcatgttag cctcaagatc gatgatgaca    1620
aaagacgaga tacaatccag agactacgac agtgcaaata cgacaaaaag cgagtgattc    1680
tcaaagatct caagcacaat gatggtaatt tcactgaaaa acagaagata gaattgaaca    1740
agttgcttca gattgactat tacaacctga ccaagttcta cggcacagtg aaacttgata    1800
ccatgatctt cggggtgata gaatactgtg agagaggatc cctccgggaa gttttaaatg    1860
acacaatttc ctaccctgat ggcacattca tggattggga gtttaagatc tctgtcttgt    1920
atgacattgc taagggaatg tcatatctgc actccagtaa gacagaagtc catggtcgtc    1980
tgaaatctac caactgcgta gtggacagta aatggtggt gaagatcact gattttggct    2040
gcaattccat tttacctcca aaaaaggacc tgtggacagc tccagagcac ctccgccaag    2100
ccaacatctc tcagaaagga gatgtgtaca gctatgggat catcgcacag gagatcatcc    2160
tgcggaaaga aaccttctac actttgagct gtcgggaccg gaatgagaag attttcagag    2220
tggaaaattc caatggaatg aaaccctttcc gcccagattt attcttggaa acagcagagg    2280
aaaaagagct agaagtgtac ctacttgtaa aaaactgttg ggaggaagat ccagaaaaga    2340
gaccagattt caaaaaaatt gagactacac ttgccaagat atttggactt tttcatgacc    2400
aaaaaaatga agctatatg gataccttga tccgacgtct acagctatat tctcgaaacc    2460
tggaacatct ggtagaggaa aggacacagc tgtacaaggc agagagggac agggctgaca    2520
gacttaactt tatgttgctt ccaaggctag tggtaaagtc tctgaaggag aaaggctttg    2580
tggagccgga actatatgag gaagttacaa tctacttcag tgacattgta ggtttcacta    2640
ctatctgcaa atacagcacc cccatggaag tggtggacat gcttaatgac atctataaga    2700
gttttgacca cattgttgat catcatgatg tctacaaggt ggaaaccatc ggtgatgcgt    2760
acatggtggc tagtggtttg cctaagagaa atggcaatcg gcatgcaata gacattgcca    2820
agatggcctt ggaaatcctc agcttcatgg ggacctttga gctggagcat cttcctggcc    2880
tcccaatatg gattcgcatt ggagttcact ctggtccctg tgctgctgga gttgtgggaa    2940
tcaagatgcc tcgttattgt ctatttggag atacggtcaa cacagcctct aggatggaat    3000
ccactggcct cccctttgaga attcacgtga gtggctccac catagccatc ctgaagagaa    3060
ctgagtgcca gttcctttat gaagtgagag agaaacata cttaaaggga agaggaaatg    3120
agactaccta ctggctgact gggatgaagg accagaaatt caacctgcca accctccta    3180 ctgtggagaa tcaacagcgt ttgcaagcag aattttcaga catgattgcc aactctttac    3240
agaaaagaca ggcagcaggg ataagaagcc aaaaacccag acgggtagcc agctataaaa    3300
aaggcactct ggaatacttg cagctgaata ccacagacaa ggagagcacc tattttttaaa    3360
```

<210> SEQ ID NO 3
<211> LENGTH: 1073
<212> TYPE: PRT
<213> ORGANISM: Homo sapiens

<400> SEQUENCE: 3

```
Met Lys Thr Leu Leu Leu Asp Leu Ala Leu Trp Ser Leu Leu Phe Gln
1               5                   10                  15

Pro Gly Trp Leu Ser Phe Ser Ser Gln Val Ser Gln Asn Cys His Asn
            20                  25                  30

Gly Ser Tyr Glu Ile Ser Val Leu Met Met Gly Asn Ser Ala Phe Ala
        35                  40                  45

Glu Pro Leu Lys Asn Leu Glu Asp Ala Val Asn Gly Leu Glu Ile
    50                  55                  60

Val Arg Gly Arg Leu Gln Asn Ala Gly Leu Asn Val Thr Val Asn Ala
65              70                  75                  80

Thr Phe Met Tyr Ser Asp Gly Leu Ile His Asn Ser Gly Asp Cys Arg
                85                  90                  95

Ser Ser Thr Cys Glu Gly Leu Asp Leu Leu Arg Lys Ile Ser Asn Ala
                100                 105                 110

Gln Arg Met Gly Cys Val Leu Ile Gly Pro Ser Cys Thr Tyr Ser Thr
            115                 120                 125

Phe Gln Met Tyr Leu Asp Thr Glu Leu Ser Tyr Pro Met Ile Ser Ala
130                 135                 140

Gly Ser Phe Gly Leu Ser Cys Asp Tyr Lys Glu Thr Leu Thr Arg Leu
145                 150                 155                 160

Met Ser Pro Ala Arg Lys Leu Met Tyr Phe Leu Val Asn Phe Trp Lys
                165                 170                 175

Thr Asn Asp Leu Pro Phe Lys Thr Tyr Ser Trp Ser Thr Ser Tyr Val
            180                 185                 190

Tyr Lys Asn Gly Thr Glu Thr Glu Asp Cys Phe Trp Tyr Leu Asn Ala
        195                 200                 205

Leu Glu Ala Ser Val Ser Tyr Phe Ser His Glu Leu Gly Phe Lys Val
    210                 215                 220

Val Leu Arg Gln Asp Lys Glu Phe Gln Asp Ile Leu Met Asp His Asn
225                 230                 235                 240

Arg Lys Ser Asn Val Ile Ile Met Cys Gly Gly Pro Glu Phe Leu Tyr
                245                 250                 255

Lys Leu Lys Gly Asp Arg Ala Val Ala Glu Asp Ile Val Ile Ile Leu
            260                 265                 270

Val Asp Leu Phe Asn Asp Gln Tyr Phe Glu Asp Asn Val Thr Ala Pro
        275                 280                 285

Asp Tyr Met Lys Asn Val Leu Val Leu Thr Leu Ser Pro Gly Asn Ser
    290                 295                 300

Leu Leu Asn Ser Ser Phe Ser Arg Asn Leu Ser Pro Thr Lys Arg Asp
305                 310                 315                 320

Phe Ala Leu Ala Tyr Leu Asn Gly Ile Leu Leu Phe Gly His Met Leu
                325                 330                 335

Lys Ile Phe Leu Glu Asn Gly Glu Asn Ile Thr Thr Pro Lys Phe Ala
            340                 345                 350

His Ala Phe Arg Asn Leu Thr Phe Glu Gly Tyr Asp Gly Pro Val Thr
        355                 360                 365

Leu Asp Asp Trp Gly Asp Val Asp Ser Thr Met Val Leu Leu Tyr Thr
    370                 375                 380

Ser Val Asp Thr Lys Lys Tyr Lys Val Leu Leu Thr Tyr Asp Thr His
385                 390                 395                 400

Val Asn Lys Thr Tyr Pro Val Asp Met Ser Pro Thr Phe Thr Trp Lys
```

```
                405                 410                 415
Asn Ser Lys Leu Pro Asn Asp Ile Thr Gly Arg Gly Pro Gln Ile Leu
            420                 425                 430

Met Ile Ala Val Phe Thr Leu Thr Gly Ala Val Leu Leu Leu Leu
            435                 440                 445

Val Ala Leu Leu Met Leu Arg Lys Tyr Arg Lys Asp Tyr Glu Leu Arg
450                 455                 460

Gln Lys Lys Trp Ser His Ile Pro Pro Glu Asn Ile Phe Pro Leu Glu
465                 470                 475                 480

Thr Asn Glu Thr Asn His Val Ser Leu Lys Ile Asp Asp Lys Arg
                485                 490                 495

Arg Asp Thr Ile Gln Arg Leu Arg Gln Cys Lys Tyr Asp Lys Lys Arg
                500                 505                 510

Val Ile Leu Lys Asp Leu Lys His Asn Asp Gly Asn Phe Thr Glu Lys
                515                 520                 525

Gln Lys Ile Glu Leu Asn Lys Leu Leu Gln Ile Asp Tyr Tyr Asn Leu
                535                 540                 
            530

Thr Lys Phe Tyr Gly Thr Val Lys Leu Asp Thr Met Ile Phe Gly Val
545                 550                 555                 560

Ile Glu Tyr Cys Glu Arg Gly Ser Leu Arg Glu Val Leu Asn Asp Thr
                565                 570                 575

Ile Ser Tyr Pro Asp Gly Thr Phe Met Asp Trp Glu Phe Lys Ile Ser
            580                 585                 590

Val Leu Tyr Asp Ile Ala Lys Gly Met Ser Tyr Leu His Ser Ser Lys
                595                 600                 605

Thr Glu Val His Gly Arg Leu Lys Ser Thr Asn Cys Val Val Asp Ser
            610                 615                 620

Arg Met Val Val Lys Ile Thr Asp Phe Gly Cys Asn Ser Ile Leu Pro
625                 630                 635                 640

Pro Lys Lys Asp Leu Trp Thr Ala Pro Glu His Leu Arg Gln Ala Asn
                645                 650                 655

Ile Ser Gln Lys Gly Asp Val Tyr Ser Tyr Gly Ile Ile Ala Gln Glu
                660                 665                 670

Ile Ile Leu Arg Lys Glu Thr Phe Tyr Thr Leu Ser Cys Arg Asp Arg
            675                 680                 685

Asn Glu Lys Ile Phe Arg Val Glu Asn Ser Asn Gly Met Lys Pro Phe
            690                 695                 700

Arg Pro Asp Leu Phe Leu Glu Thr Ala Glu Glu Lys Glu Leu Glu Val
705                 710                 715                 720

Tyr Leu Leu Val Lys Asn Cys Trp Glu Glu Asp Pro Glu Lys Arg Pro
                725                 730                 735

Asp Phe Lys Lys Ile Glu Thr Thr Leu Ala Lys Ile Phe Gly Leu Phe
            740                 745                 750

His Asp Gln Lys Asn Glu Ser Tyr Met Asp Thr Leu Ile Arg Arg Leu
            755                 760                 765

Gln Leu Tyr Ser Arg Asn Leu Glu His Leu Val Glu Glu Arg Thr Gln
            770                 775                 780

Leu Tyr Lys Ala Glu Arg Asp Arg Ala Asp Arg Leu Asn Phe Met Leu
785                 790                 795                 800

Leu Pro Arg Leu Val Val Lys Ser Leu Lys Glu Lys Gly Phe Val Glu
                805                 810                 815

Pro Glu Leu Tyr Glu Glu Val Thr Ile Tyr Phe Ser Asp Ile Val Gly
            820                 825                 830
```

Phe Thr Thr Ile Cys Lys Tyr Ser Thr Pro Met Glu Val Val Asp Met
            835                 840                 845

Leu Asn Asp Ile Tyr Lys Ser Phe Asp His Ile Val Asp His His Asp
        850                 855                 860

Val Tyr Lys Val Glu Thr Ile Gly Asp Ala Tyr Met Val Ala Ser Gly
865                 870                 875                 880

Leu Pro Lys Arg Asn Gly Asn Arg His Ala Ile Asp Ile Ala Lys Met
            885                 890                 895

Ala Leu Glu Ile Leu Ser Phe Met Gly Thr Phe Glu Leu Glu His Leu
        900                 905                 910

Pro Gly Leu Pro Ile Trp Ile Arg Ile Gly Val His Ser Gly Pro Cys
            915                 920                 925

Ala Ala Gly Val Val Gly Ile Lys Met Pro Arg Tyr Cys Leu Phe Gly
        930                 935                 940

Asp Thr Val Asn Thr Ala Ser Arg Met Glu Ser Thr Gly Leu Pro Leu
945                 950                 955                 960

Arg Ile His Val Ser Gly Ser Thr Ile Ala Ile Leu Lys Arg Thr Glu
            965                 970                 975

Cys Gln Phe Leu Tyr Glu Val Arg Gly Glu Thr Tyr Leu Lys Gly Arg
        980                 985                 990

Gly Asn Glu Thr Thr Tyr Trp Leu Thr Gly Met Lys Asp Gln Lys Phe
            995                 1000                1005

Asn Leu Pro Thr Pro Pro Thr Val Glu Asn Gln Gln Arg Leu Gln
        1010                1015                1020

Ala Glu Phe Ser Asp Met Ile Ala Asn Ser Leu Gln Lys Arg Gln
        1025                1030                1035

Ala Ala Gly Ile Arg Ser Gln Lys Pro Arg Arg Val Ala Ser Tyr
        1040                1045                1050

Lys Lys Gly Thr Leu Glu Tyr Leu Gln Leu Asn Thr Thr Asp Lys
        1055                1060                1065

Glu Ser Thr Tyr Phe
        1070

<210> SEQ ID NO 4
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atggagactg ggctgcgctg gcttctcctg gtcgctgtgc tcaaaggtgt ccagtgtcag    60
tcagtgaagg agtccggggg aggcctcttc aagccaacgg ataccctgac actcacctgc   120
accgtctctg gattctccct cagtagtcat agaatgaact gggtccgcca gactccaggg   180 aagggctgg  aatggatcgc aatcattact cataatagta tcacatacta cgcgagctgg   240
gcgaaaagcc gatccaccat caccagaaac accagcgaga cacggtgac  tctgaaaatg   300 accagtctga cagccgcgga cacgccact  tatttctgtg ccagagagga tagtatgggg   360
tattattttg acttgtgggg cccaggcacc ctggtcacca tctcctcagg caacctaag    420 gctccatcag tcttcccact ggccccctgc tgcgggaca  cacccagctc acggtgacc    480 ctgggctgcc tggtcaaagg gtacctcccg gagccagtga ccgtgacctg gaactcgggc   540
accctcacca tggggtacg  caccttcccg tccgtccggc agtcctcagg cctctactcg   600

```
ctgagcagcg tggtgagcgt gacctcaagc agccagcccg tcacctgcaa cgtggcccac    660
ccagccacca acaccaaagt ggacaagacc gttgcgccct cgacatgcag caagcccacg    720
tgcccacccc ctgaactcct gggggggaccg tctgtcttca tcttccccccc aaaacccaag    780 gacaccctca tgatctcacg cacccccgag gtcacatgcg tggtggtgga cgtgagccac    840
gatgaccccg aggtgcagtt cacatggtac ataaacaacg agcaggtgcg caccgcccgg    900
ccgccgctac gggagcagca gttcaacagc acgatccgcg tggtcagcac cctccccatc    960
gcgcaccagg actggctgag gggcaaggag ttcaagtgca aagtccacaa caaggcactc   1020
ccggccccca tcgagaaaac catctccaaa gccagagggc agcccctgga gccgaaggtc   1080
tacaccatgg gcctccccg ggaggagctg agcagcaggt cggtcagcct gacctgcatg   1140
atcaacggct tctacccttc cgacatctcg gtggagtggg agaagaacgg gaaggcagag   1200
gacaactaca agaccacgcc ggccgtgctg gacagcgacg gctcctactt cctctacagc   1260
aagctctcag tgcccacgag tgagtggcag cggggcgacg tcttcacctg ctccgtgatg   1320
cacgaggcct tgcacaacca ctacacgcag aagtccatct cccgctctcc gggtaaatga   1380
```

```
<210> SEQ ID NO 5
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
```

```
atggacacga gggcccccac tcagctgctg gggctcctgc tgctctggct cccaggtgcc     60
agatgtgcct atgatatgac ccagactcca gcctctgtgg aggtagctgt gggaggcaca    120
gtcaccatca agtgccaggc cagtcagagc attagtaact ggttagcctg gtatcagcag    180
aaaccagggc agtctcccaa gcccctgatc tacagggcat ccactctggc atctggggtc    240
tcatcgcggt tcagaggcag tggatctggg acacagttca ctctcaccat cagtggcgtg    300
gagtgtgccg atgctgccac ttactactgt cagcagactt atactaataa tcatcttgat    360
aatggtttcg gcggagggac cgaggtggtg gtcaaaggtg atccagttgc acctactgtc    420
ctcatcttcc caccagctgc tgatcaggtg gcaactggaa cagtcaccat cgtgtgtgtg    480
gcgaataaat actttcccga tgtcaccgtc acctgggagg tggatggcac acccaaaca    540 actggcatcg agaacagtaa aaccccgcag aattctgcag attgtaccta caacctcagc    600
agcactctga cactgaccag cacacagtac aacagccaca aagagtacac ctgcagggtg    660
acccagggca cgacctcagt cgtccagagc ttcaataggg gtgactgtta g            711
```

```
<210> SEQ ID NO 6
<211> LENGTH: 1377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
```

```
atggagactg gctgcgctg gcttctcctg gtcgctgtgc tcaaaggtgt ccagtgtcag     60
tcggtggagg agtccggggg tcgcctggtc acgcctggga cacccctgac actcacctgc    120
acagcctctg gatccgacat cagtaactat gcaatatcct gggtccgcca ggctccaggg    180
```

```
aaggggctgg aattcatcgg atatattagt tatggtaaaa gtatatacta cgcgagctgg    240
gcgaaaggcc ggttcgccat ctccaaaacc tcgtcgacca cggtggatct ggaaatcacc    300
agtccgacaa ccgaggacac ggccacctat ttttgtgcca gagaggatag tgctacttat    360
agtcctaact tgtggggccc aggcaccctg gtcaccgtct cctcaggca acctaaggct     420 ccatcagtct tcccactggc ccctgctgc ggggacacac ccagctccac ggtgaccctg     480
ggctgcctgg tcaaagggta cctcccggag ccagtgaccg tgacctggaa ctcgggcacc    540
ctcaccaatg gggtacgcac cttcccgtcc gtccggcagt cctcaggcct ctactcgctg    600
agcagcgtgg tgagcgtgac ctcaagcagc cagcccgtca cctgcaacgt ggcccaccca    660
gccaccaaca ccaaagtgga caagaccgtt gcgcctcga catgcagcaa gcccacgtgc      720
ccaccccctg aactcctggg gggaccgtct gtcttcatct ccccccaaa acccaaggac      780 accctcatga tctcacgcac ccccgaggtc acatgcgtgg tggtggacgt gagccaggat    840
gaccccgagg tgcagttcac atggtacata aacaacgagc aggtgcgcac cgccggccg     900 ccgctacggg agcagcagtt caacagcacg atccgcgtgg tcagcaccct ccccatcgcg    960
caccaggact ggctgagggg caaggagttc aagtgcaaag tccacaacaa ggcactcccg   1020
gcccccatcg agaaaaccat ctccaaagcc agagggcagc cctggagcc gaaggtctac    1080 accatgggcc ctcccggga ggagctgagc agcaggtcgg tcagcctgac ctgcatgatc    1140
aacggcttct acccttccga catctcggtg gagtgggaga gaacgggaa ggcagaggac    1200 aactacaaga ccacgccggc cgtgctggac agcgacggct cctacttcct ctacagcaag   1260
ctctcagtgc ccacgagtga gtggcagcgg ggcgacgtct tcacctgctc cgtgatgcac    1320
gaggccttgc acaaccacta cacgcagaag tccatctccc gctctccggg taaatga       1377

<210> SEQ ID NO 7
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atggacacga gggcccccac tcagctgctg ggctcctgc tgctctggct cccaggtgcc      60
agatgtgcct atgatatgac ccagactcca gcctctgtgg aggtagctgt gggaggcaca    120
gtcaccatca gtgccaggc cagtcagagt attaacacct acttagcctg gtatcagcag    180
aaaccagggc agcgtcccaa gctcctgatc tacagggcat ccactctggc atctggggtc    240
tcatcgcggt tcaaaggcag tggatctggg acagagttca ctctcaccat cagcggcgtg    300
gagtgtgccg atgctgccac ttactactgt caacagggtt atagttataa taatcttgat    360
cgtgctttcg gcggagggac cgaggtggtg gtcacaggtg atccagttgc acctactgtc    420
ctcatcttcc caccagctgc tgatcaggtg gcaactggaa cagtcaccat cgtgtgtgtg    480
gcgaataaat actttcccga tgtcaccgtc acctgggagg tggatggcac cacccaaaca    540
actggcatcg agaacagtaa aaccaccgcag aattctgcag attgtaccta caacctcagc    600
agcactctga cactgaccag cacacagtac aacagccaca aagagtacac ctgcaaggtg    660
acccagggca cgacctcagt cgtccagagc ttcaataggg gtgactgtta g             711

<210> SEQ ID NO 8
<211> LENGTH: 30
<212> TYPE: PRT
```

<213> ORGANISM: Homo sapiens

<400> SEQUENCE: 8

Ile Leu Val Asp Leu Phe Asn Asp Gln Tyr Phe Glu Asp Asn Val Thr
1               5                   10                  15
Ala Pro Asp Tyr Met Lys Asn Val Leu Val Leu Thr Leu Ser
            20                  25                  30

<210> SEQ ID NO 9
<211> LENGTH: 25
<212> TYPE: PRT
<213> ORGANISM: Homo sapiens

<400> SEQUENCE: 9

Phe Ala His Ala Phe Arg Asn Leu Thr Phe Glu Gly Tyr Asp Gly Pro
1               5                   10                  15
Val Thr Leu Asp Asp Trp Gly Asp Val
            20                  25

<210> SEQ ID NO 10
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
cagtcagtga aggagtccgg gggaggcctc ttcaagccaa cggataccct gacactcacc      60
tgcaccgtct ctggattctc cctcagtagt catagaatga actgggtccg ccagactcca     120
gggaaggggc tggaatggat cgcaatcatt actcataata gtatcacata ctacgcgagc     180
tgggcgaaaa gccgatccac catcaccaga aacaccagcg agaacacggt gactctgaaa     240
atgaccagtc tgacagccgc ggacacggcc acttatttct gtgccagaga ggatagtatg     300
gggtattatt ttgacttgtg gggcccaggc accctggtca ccatctcctc a              351

<210> SEQ ID NO 11
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Ser Val Lys Glu Ser Gly Gly Gly Leu Phe Lys Pro Thr Asp Thr
1               5                   10                  15
Leu Thr Leu Thr Cys Thr Val Ser Gly Phe Ser Leu Ser Ser His Arg
            20                  25                  30
Met Asn Trp Val Arg Gln Thr Pro Gly Lys Gly Leu Glu Trp Ile Ala
        35                  40                  45
Ile Ile Thr His Asn Ser Ile Thr Tyr Tyr Ala Ser Trp Ala Lys Ser
    50                  55                  60
Arg Ser Thr Ile Thr Arg Asn Thr Ser Glu Asn Thr Val Thr Leu Lys
65                  70                  75                  80
Met Thr Ser Leu Thr Ala Ala Asp Thr Ala Thr Tyr Phe Cys Ala Arg
                85                  90                  95
Glu Asp Ser Met Gly Tyr Tyr Phe Asp Leu Trp Gly Pro Gly Thr Leu
            100                 105                 110

Val Thr Ile Ser Ser
        115

<210> SEQ ID NO 12
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gcctatgata tgacccagac tccagcctct gtggaggtag ctgtgggagg cacagtcacc      60
atcaagtgcc aggccagtca gagcattagt aactggttag cctggtatca gcagaaacca     120
gggcagtctc ccaagcccct gatctacagg gcatccactc tggcatctgg ggtctcatcg     180
cggttcagag gcagtggatc tgggacacag ttcactctca ccatcagtgg cgtggagtgt     240
gccgatgctg ccacttacta ctgtcagcag acttatacta taatcatct tgataatggt      300 ttcggcggag ggaccgaggt ggtggtcaaa                                       330

<210> SEQ ID NO 13
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Asn Trp
            20                  25                  30

Leu Ala Trp Tyr Gln Gln Lys Pro Gly Gln Ser Pro Lys Pro Leu Ile
        35                  40                  45

Tyr Arg Ala Ser Thr Leu Ala Ser Gly Val Ser Ser Arg Phe Arg Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Thr Tyr Thr Asn Asn His
                85                  90                  95

Leu Asp Asn Gly Phe Gly Gly Gly Thr Glu Val Val Val Lys
            100                 105                 110

<210> SEQ ID NO 14
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
cagtcggtgg aggagtccgg gggtcgcctg gtcacgcctg ggacacccct gacactcacc      60
tgcacagcct ctggatccga catcagtaac tatgcaatat cctgggtccg ccaggctcca     120
gggaaggggc tggaattcat cggatatatt agttatggta aaagtatata ctacgcgagc     180
tgggcgaaag gccggttcgc catctcccaaa acctcgtcga ccacggtgga tctggaaatc     240
accagtccga caaccgagga cacggccacc tattttgtg ccagagagga tagtgctact      300
tatagtccta acttgtgggg cccaggcacc ctggtcaccg tctcctca           348

<210> SEQ ID NO 15
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ser Val Glu Glu Ser Gly Gly Arg Leu Val Thr Pro Gly Thr Pro
1               5                   10                  15

Leu Thr Leu Thr Cys Thr Ala Ser Gly Ser Asp Ile Ser Asn Tyr Ala
            20                  25                  30

Ile Ser Trp Val Arg Gln Ala Pro Gly Lys Gly Leu Glu Phe Ile Gly
        35                  40                  45

Tyr Ile Ser Tyr Gly Lys Ser Ile Tyr Tyr Ala Ser Trp Ala Lys Gly
    50                  55                  60

Arg Phe Ala Ile Ser Lys Thr Ser Ser Thr Thr Val Asp Leu Glu Ile
65                  70                  75                  80

Thr Ser Pro Thr Thr Glu Asp Thr Ala Thr Tyr Phe Cys Ala Arg Glu
                85                  90                  95

Asp Ser Ala Thr Tyr Ser Pro Asn Leu Trp Gly Pro Gly Thr Leu Val
            100                 105                 110

Thr Val Ser Ser
        115

<210> SEQ ID NO 16
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gcctatgata tgacccagac tccagcctct gtggaggtag ctgtgggagg cacagtcacc     60
atcaagtgcc aggccagtca gagtattaac acctacttag cctggtatca gcagaaacca   120
gggcagcgtc ccaagctcct gatctacagg catccactc tggcatctgg ggtctcatcg     180
cggttcaaag gcagtggatc tgggacagag ttcactctca ccatcagcgg cgtggagtgt   240
gccgatgctg ccacttacta ctgtcaacag ggttatagtt ataataatct tgatcgtgct   300
ttcggcggag ggaccgaggt ggtggtcaca                                    330

<210> SEQ ID NO 17
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Asn Thr Tyr
            20                  25                  30

Leu Ala Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
            50                  55                  60

Ser Gly Ser Gly Thr Glu Phe Thr Leu Thr Ile Ser Gly Val Glu Cys
65                  70                  75                  80

Ala Asp Ala Ala Thr Tyr Tyr Cys Gln Gln Gly Tyr Ser Tyr Asn Asn
                85                  90                  95

Leu Asp Arg Ala Phe Gly Gly Gly Thr Glu Val Val Val Thr
            100                 105                 110

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agtcatagaa tgaac                                                    15

<210> SEQ ID NO 19
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atcattactc ataatagtat cacatactac gcgagctggg cgaaaagc                48

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gaggatagta tggggtatta ttttgacttg                                    30

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser His Arg Met Asn
1               5

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Ile Thr His Asn Ser Ile Thr Tyr Tyr Ala Ser Trp Ala Lys Ser
1               5                   10                  15

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Asp Ser Met Gly Tyr Tyr Phe Asp Leu
1               5                   10

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
caggccagtc agagcattag taactggtta gcc                                   33

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
agggcatcca ctctggcatc t                                                21

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cagcagactt atactaataa tcatcttgat aatggt                                36

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Ala Ser Gln Ser Ile Ser Asn Trp Leu Ala
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Arg Ala Ser Thr Leu Ala Ser
1               5

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Gln Thr Tyr Thr Asn Asn His Leu Asp Asn Gly
1               5                   10

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aactatgcaa tatcc                                                    15

<210> SEQ ID NO 31
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tatattagtt atggtaaaag tatatactac gcgagctggg cgaaaggc                48

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
agtcctaact tg                                                       12

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asn Tyr Ala Ile Ser
1               5

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 34

Tyr Ile Ser Tyr Gly Lys Ser Ile Tyr Tyr Ala Ser Trp Ala Lys Gly
1               5                   10                  15

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Asp Ser Ala Thr Tyr Ser Pro Asn Leu
1               5                   10

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
caggccagtc agagtattaa cacctactta gcc                                    33

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agggcatcca ctctggcatc t                                                 21

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
caacagggtt atagttataa taatcttgat cgtgct                                 36

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ala Ser Gln Ser Ile Asn Thr Tyr Leu Ala
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 40

Arg Ala Ser Thr Leu Ala Ser
1               5

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Gln Gly Tyr Ser Tyr Asn Asn Leu Asp Arg Ala
1               5                   10

<210> SEQ ID NO 42
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Glu Thr Gly Leu Arg Trp Leu Leu Leu Val Ala Val Leu Lys Gly
1               5                   10                  15

Val Gln Cys Gln Ser Val Lys Glu Ser Gly Gly Gly Leu Phe Lys Pro
            20                  25                  30

Thr Asp Thr Leu Thr Leu Thr Cys Thr Val Ser Gly Phe Ser Leu Ser
        35                  40                  45

Ser His Arg Met Asn Trp Val Arg Gln Thr Pro Gly Lys Gly Leu Glu
    50                  55                  60

Trp Ile Ala Ile Ile Thr His Asn Ser Ile Thr Tyr Tyr Ala Ser Trp
65                  70                  75                  80

Ala Lys Ser Arg Ser Thr Ile Thr Arg Asn Thr Ser Glu Asn Thr Val
                85                  90                  95

Thr Leu Lys Met Thr Ser Leu Thr Ala Ala Asp Thr Ala Thr Tyr Phe
            100                 105                 110

Cys Ala Arg Glu Asp Ser Met Gly Tyr Tyr Phe Asp Leu Trp Gly Pro
        115                 120                 125

Gly Thr Leu Val Thr Ile Ser Ser Gly Gln Pro Lys Ala Pro Ser Val
    130                 135                 140

Phe Pro Leu Ala Pro Cys Cys Gly Asp Thr Pro Ser Ser Thr Val Thr
145                 150                 155                 160

Leu Gly Cys Leu Val Lys Gly Tyr Leu Pro Glu Pro Val Thr Val Thr
                165                 170                 175

Trp Asn Ser Gly Thr Leu Thr Asn Gly Val Arg Thr Phe Pro Ser Val
            180                 185                 190

Arg Gln Ser Ser Gly Leu Tyr Ser Leu Ser Ser Val Val Ser Val Thr
        195                 200                 205

Ser Ser Ser Gln Pro Val Thr Cys Asn Val Ala His Pro Ala Thr Asn
    210                 215                 220

Thr Lys Val Asp Lys Thr Val Ala Pro Ser Thr Cys Ser Lys Pro Thr
225                 230                 235                 240

Cys Pro Pro Pro Glu Leu Leu Gly Gly Pro Ser Val Phe Ile Phe Pro
                245                 250                 255
```

```
Pro Lys Pro Lys Asp Thr Leu Met Ile Ser Arg Thr Pro Glu Val Thr
            260                 265                 270

Cys Val Val Asp Val Ser Gln Asp Pro Glu Val Gln Phe Thr
            275                 280                 285

Trp Tyr Ile Asn Asn Glu Gln Val Arg Thr Ala Arg Pro Pro Leu Arg
        290                 295                 300

Glu Gln Gln Phe Asn Ser Thr Ile Arg Val Val Ser Thr Leu Pro Ile
305                 310                 315                 320

Ala His Gln Asp Trp Leu Arg Gly Lys Glu Phe Lys Cys Lys Val His
                325                 330                 335

Asn Lys Ala Leu Pro Ala Pro Ile Glu Lys Thr Ile Ser Lys Ala Arg
                340                 345                 350

Gly Gln Pro Leu Glu Pro Lys Val Tyr Thr Met Gly Pro Pro Arg Glu
                355                 360                 365

Glu Leu Ser Ser Arg Ser Val Ser Leu Thr Cys Met Ile Asn Gly Phe
    370                 375                 380

Tyr Pro Ser Asp Ile Ser Val Glu Trp Glu Lys Asn Gly Lys Ala Glu
385                 390                 395                 400

Asp Asn Tyr Lys Thr Thr Pro Ala Val Leu Asp Ser Asp Gly Ser Tyr
                405                 410                 415

Phe Leu Tyr Ser Lys Leu Ser Val Pro Thr Ser Glu Trp Gln Arg Gly
                420                 425                 430

Asp Val Phe Thr Cys Ser Val Met His Glu Ala Leu His Asn His Tyr
            435                 440                 445

Thr Gln Lys Ser Ile Ser Arg Ser Pro Gly Lys
    450                 455

<210> SEQ ID NO 43
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Gln Ser Ile Ser Asn Trp Leu Ala Trp Tyr Gln Gln Lys Pro Gly Gln
    50                  55                  60

Ser Pro Lys Pro Leu Ile Tyr Arg Ala Ser Thr Leu Ala Ser Gly Val
65                  70                  75                  80

Ser Ser Arg Phe Arg Gly Ser Gly Ser Gly Thr Gln Phe Thr Leu Thr
                85                  90                  95

Ile Ser Gly Val Glu Cys Ala Asp Ala Ala Thr Tyr Tyr Cys Gln Gln
            100                 105                 110

Thr Tyr Thr Asn Asn His Leu Asp Asn Gly Phe Gly Gly Gly Thr Glu
        115                 120                 125

Val Val Val Lys Gly Asp Pro Val Ala Pro Thr Val Leu Ile Phe Pro
    130                 135                 140

Pro Ala Ala Asp Gln Val Ala Thr Gly Thr Val Thr Ile Val Cys Val
```

```
145                 150                 155                 160
Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
            195                 200                 205

Gln Tyr Asn Ser His Lys Glu Tyr Thr Cys Arg Val Thr Gln Gly Thr
        210                 215                 220

Thr Ser Val Val Gln Ser Phe Asn Arg Gly Asp Cys
225                 230                 235

<210> SEQ ID NO 44
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Ser Asp Ile Ser
        35                  40                  45

Asn Tyr Ala Ile Ser Trp Val Arg Gln Ala Pro Gly Lys Gly Leu Glu
    50                  55                  60

Phe Ile Gly Tyr Ile Ser Tyr Gly Lys Ser Ile Tyr Tyr Ala Ser Trp
65                  70                  75                  80

Ala Lys Gly Arg Phe Ala Ile Ser Lys Thr Ser Ser Thr Thr Val Asp
                85                  90                  95

Leu Glu Ile Thr Ser Pro Thr Thr Glu Asp Thr Ala Thr Tyr Phe Cys
            100                 105                 110

Ala Arg Glu Asp Ser Ala Thr Tyr Ser Pro Asn Leu Trp Gly Pro Gly
        115                 120                 125

Thr Leu Val Thr Val Ser Ser Gly Gln Pro Lys Ala Pro Ser Val Phe
    130                 135                 140

Pro Leu Ala Pro Cys Cys Gly Asp Thr Pro Ser Ser Thr Val Thr Leu
145                 150                 155                 160

Gly Cys Leu Val Lys Gly Tyr Leu Pro Glu Pro Val Thr Val Thr Trp
                165                 170                 175

Asn Ser Gly Thr Leu Thr Asn Gly Val Arg Thr Phe Pro Ser Val Arg
            180                 185                 190

Gln Ser Ser Gly Leu Tyr Ser Leu Ser Ser Val Val Ser Val Thr Ser
        195                 200                 205

Ser Ser Gln Pro Val Thr Cys Asn Val Ala His Pro Ala Thr Asn Thr
    210                 215                 220

Lys Val Asp Lys Thr Val Ala Pro Ser Thr Cys Ser Lys Pro Thr Cys
225                 230                 235                 240

Pro Pro Pro Glu Leu Leu Gly Gly Pro Ser Val Phe Ile Phe Pro Pro
                245                 250                 255

Lys Pro Lys Asp Thr Leu Met Ile Ser Arg Thr Pro Glu Val Thr Cys
            260                 265                 270
```

Val Val Val Asp Val Ser Gln Asp Asp Pro Glu Val Gln Phe Thr Trp
            275                 280                 285

Tyr Ile Asn Asn Glu Gln Val Arg Thr Ala Arg Pro Pro Leu Arg Glu
        290                 295                 300

Gln Gln Phe Asn Ser Thr Ile Arg Val Val Ser Thr Leu Pro Ile Ala
305                 310                 315                 320

His Gln Asp Trp Leu Arg Gly Lys Glu Phe Lys Cys Lys Val His Asn
                325                 330                 335

Lys Ala Leu Pro Ala Pro Ile Glu Lys Thr Ile Ser Lys Ala Arg Gly
            340                 345                 350

Gln Pro Leu Glu Pro Lys Val Tyr Thr Met Gly Pro Pro Arg Glu Glu
        355                 360                 365

Leu Ser Ser Arg Ser Val Ser Leu Thr Cys Met Ile Asn Gly Phe Tyr
    370                 375                 380

Pro Ser Asp Ile Ser Val Glu Trp Glu Lys Asn Gly Lys Ala Glu Asp
385                 390                 395                 400

Asn Tyr Lys Thr Thr Pro Ala Val Leu Asp Ser Asp Gly Ser Tyr Phe
                405                 410                 415

Leu Tyr Ser Lys Leu Ser Val Pro Thr Ser Glu Trp Gln Arg Gly Asp
            420                 425                 430

Val Phe Thr Cys Ser Val Met His Glu Ala Leu His Asn His Tyr Thr
        435                 440                 445

Gln Lys Ser Ile Ser Arg Ser Pro Gly Lys
    450                 455

<210> SEQ ID NO 45
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Gln Ser Ile Asn Thr Tyr Leu Ala Trp Tyr Gln Gln Lys Pro Gly Gln
    50                  55                  60

Arg Pro Lys Leu Leu Ile Tyr Arg Ala Ser Thr Leu Ala Ser Gly Val
65                  70                  75                  80

Ser Ser Arg Phe Lys Gly Ser Gly Ser Gly Thr Glu Phe Thr Leu Thr
                85                  90                  95

Ile Ser Gly Val Glu Cys Ala Asp Ala Ala Thr Tyr Tyr Cys Gln Gln
            100                 105                 110

Gly Tyr Ser Tyr Asn Asn Leu Asp Arg Ala Phe Gly Gly Gly Thr Glu
        115                 120                 125

Val Val Val Thr Gly Asp Pro Val Ala Pro Thr Val Leu Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

```
Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235

<210> SEQ ID NO 46
<211> LENGTH: 420
<212> TYPE: PRT
<213> ORGANISM: Homo sapiens

<400> SEQUENCE: 46

Met Lys Thr Leu Leu Asp Leu Ala Leu Trp Ser Leu Leu Phe Gln
1               5                   10                  15

Pro Gly Trp Leu Ser Phe Ser Ser Gln Val Ser Gln Asn Cys His Asn
                20                  25                  30

Gly Ser Tyr Glu Ile Ser Val Leu Met Met Gly Asn Ser Ala Phe Ala
            35                  40                  45

Glu Pro Leu Lys Asn Leu Glu Asp Ala Val Asn Glu Gly Leu Glu Ile
        50                  55                  60

Val Arg Gly Arg Leu Gln Asn Ala Gly Leu Asn Val Thr Val Asn Ala
65                  70                  75                  80

Thr Phe Met Tyr Ser Asp Gly Leu Ile His Asn Ser Gly Asp Cys Arg
                85                  90                  95

Ser Ser Thr Cys Glu Gly Leu Asp Leu Leu Arg Lys Ile Ser Asn Ala
            100                 105                 110

Gln Arg Met Gly Cys Val Leu Ile Gly Pro Ser Cys Thr Tyr Ser Thr
        115                 120                 125

Phe Gln Met Tyr Leu Asp Thr Glu Leu Ser Tyr Pro Met Ile Ser Ala
    130                 135                 140

Gly Ser Phe Gly Leu Ser Cys Asp Tyr Lys Glu Thr Leu Thr Arg Leu
145                 150                 155                 160

Met Ser Pro Ala Arg Lys Leu Met Tyr Phe Leu Val Asn Phe Trp Lys
                165                 170                 175

Thr Asn Asp Leu Pro Phe Lys Thr Tyr Ser Trp Ser Thr Ser Tyr Val
            180                 185                 190

Tyr Lys Asn Gly Thr Glu Thr Glu Asp Cys Phe Trp Tyr Leu Asn Ala
        195                 200                 205

Leu Glu Ala Ser Val Ser Tyr Phe Ser His Glu Leu Gly Phe Lys Val
    210                 215                 220

Val Leu Arg Gln Asp Lys Glu Phe Gln Asp Ile Leu Met Asp His Asn
225                 230                 235                 240

Arg Lys Ser Asn Val Ile Ile Met Cys Gly Gly Pro Glu Phe Leu Tyr
                245                 250                 255

Lys Leu Lys Gly Asp Arg Ala Val Ala Glu Asp Ile Val Ile Ile Leu
            260                 265                 270

Val Asp Leu Phe Asn Asp Gln Tyr Phe Glu Asp Asn Val Thr Ala Pro
        275                 280                 285

Asp Tyr Met Lys Asn Val Leu Val Leu Thr Leu Ser Pro Gly Asn Ser
    290                 295                 300

Leu Leu Asn Ser Ser Phe Ser Arg Asn Leu Ser Pro Thr Lys Arg Asp
```

```
              305                 310                 315                 320
     Phe Ala Leu Ala Tyr Leu Asn Gly Ile Leu Leu Phe Gly His Met Leu
                     325                 330                 335

Lys Ile Phe Leu Glu Asn Gly Glu Asn Ile Thr Thr Pro Lys Phe Ala
                     340                 345                 350

His Ala Phe Arg Asn Leu Thr Phe Glu Gly Tyr Asp Gly Pro Val Thr
                     355                 360                 365

Leu Asp Asp Trp Gly Asp Val Asp Ser Thr Met Val Leu Leu Tyr Thr
         370                 375                 380

Ser Val Asp Thr Lys Lys Tyr Lys Val Leu Leu Thr Tyr Asp Thr His
     385                 390                 395                 400

Val Asn Lys Thr Tyr Pro Val Asp Met Ser Pro Thr Phe Thr Trp Lys
                     405                 410                 415

Asn Ser Lys Leu
                     420

<210> SEQ ID NO 47
<211> LENGTH: 2028
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
cgcggatccc tcaccatgaa gacgttgctg ttggacttgg ctttgtggtc actgctcttc      60
cagcccgggt ggctgtcctt tagttcccag gtgagtcaga actgccacaa tggcagctat     120
gaaatcagcg tcctgatgat gggcaactca gcctttgcag agcccctgaa aacttggaa      180 gatgcggtga atgaggggct ggaaatagtg agaggacgtc tgcaaaatgc tggcctaaat     240
gtgactgtga acgctacttt catgtattcg gatggtctga ttcataactc aggcgactgc     300
cggagtagca cctgtgaagg cctcgaccta ctcaggaaaa tttcaaatgc acaacggatg     360
ggctgtgtcc tcatagggcc ctcatgtaca tactccacct tccagatgta ccttgacaca     420
gaattgagct accccatgat ctcagctgga agttttggat tgtcatgtga ctataaagaa     480
accttaacca ggctgatgtc tccagctaga agttgatgt acttcttggt taacttttgg     540
aaaaccaacg atctgccctt caaaacttat tcctggagca cttcgtatgt ttacaagaat     600
ggtacagaaa ctgaggactg tttctggtac cttaatgctc tggaggctag cgtttcctat     660
ttctcccacg aactcggctt taaggtggtg ttaagacaag ataaggagtt tcaggatatc     720
ttaatggacc acaacaggaa agcaatgtg attattatgt gtggtggtcc agagttcctc     780
tacaagctga gggtgaccg agcagtggct gaagacattg tcattattct agtggatctt     840
ttcaatgacc agtacttgga ggacaatgtc acagcccctg actatatgaa aaatgtcctt     900
gttctgacgc tgtctcctgg gaattcccct ctaaatagct ctttctccag gaatctatca     960
ccaacaaaac gagactttgc tcttgcctat ttgaatggaa tcctgctctt tggacatatg    1020
ctgaagatat ttcttgaaaa tggagaaaat attaccaccc caaatttgc tcatgctttc    1080 aggaatctca cttttgaagg gtatgacggt ccagtgacct tggatgactg ggggatgtt    1140 gacagtacca tggtgcttct gtatacctct gtggacacca gaaatacaa ggttcttttg    1200 acctatgata cccacgtaaa taagacctat cctgtggata tgagcccac attcacttgg    1260 aagaactcta aacttcctaa tgatattaca ggcgggggcc ctcagcccag agtgcccata    1320
acacagaacc cctgtcctcc actcaaagag tgtccccat gcgcagctcc agacctcgca    1380
```

```
ggtgcaccat ccgtcttcat cttccctcca aagatcaagg atgtactcat gatctccctg    1440
agccccatgg tcacatgtgt ggtggtggat gtgagcgagg atgacccaga cgtccagatc    1500
agctggtttg tgaacaacgt ggaagtacac acagctcaga cacaaaccca tagagaggat    1560
tacaacagta ctctccgggt ggtcagtgcc ctccccatcc agcaccagga ctggatgagt    1620
ggcaaggcat tcaaatgcaa ggtcaacaac agagccctcc catcccccat cgagaaaacc    1680
atctcaaaac ccagagggcc agtaagagct ccacaggtat atgtcttgcc tccaccagca    1740
gaagagatga ctaagaaaga gttcagtctg acctgcatga tcacaggctt cttacctgcc    1800
gaaattgctg tggactggac cagcaatggg cgtacagagc aaaactacaa gaacaccgca    1860
acagtcctgg actctgatgg ttcttacttc atgtacagca agctcagagt acaaaagagc    1920
acttgggaaa gaggaagtct tttcgcctgc tcagtggtcc acgagggtct gcacaatcac    1980
cttacgacta agaccatctc ccggtctctg ggtaaataat ctagagca              2028
```

<210> SEQ ID NO 48
<211> LENGTH: 667
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Met Lys Thr Leu Leu Asp Leu Ala Leu Trp Ser Leu Leu Phe Gln
1               5                   10                  15

Pro Gly Trp Leu Ser Phe Ser Ser Gln Val Ser Gln Asn Cys His Asn
                20                  25                  30

Gly Ser Tyr Glu Ile Ser Val Leu Met Met Gly Asn Ser Ala Phe Ala
            35                  40                  45

Glu Pro Leu Lys Asn Leu Glu Asp Ala Val Asn Glu Gly Leu Glu Ile
        50                  55                  60

Val Arg Gly Arg Leu Gln Asn Ala Gly Leu Asn Val Thr Val Asn Ala
65                  70                  75                  80

Thr Phe Met Tyr Ser Asp Gly Leu Ile His Asn Ser Gly Asp Cys Arg
                85                  90                  95

Ser Ser Thr Cys Glu Gly Leu Asp Leu Leu Arg Lys Ile Ser Asn Ala
            100                 105                 110

Gln Arg Met Gly Cys Val Leu Ile Gly Pro Ser Cys Thr Tyr Ser Thr
        115                 120                 125

Phe Gln Met Tyr Leu Asp Thr Glu Leu Ser Tyr Pro Met Ile Ser Ala
130                 135                 140

Gly Ser Phe Gly Leu Ser Cys Asp Tyr Lys Glu Thr Leu Thr Arg Leu
145                 150                 155                 160

Met Ser Pro Ala Arg Lys Leu Met Tyr Phe Leu Val Asn Phe Trp Lys
                165                 170                 175

Thr Asn Asp Leu Pro Phe Lys Thr Tyr Ser Trp Ser Thr Ser Tyr Val
            180                 185                 190

Tyr Lys Asn Gly Thr Glu Thr Glu Asp Cys Phe Trp Tyr Leu Asn Ala
        195                 200                 205

Leu Glu Ala Ser Val Ser Tyr Phe Ser His Glu Leu Gly Phe Lys Val
210                 215                 220

Val Leu Arg Gln Asp Lys Glu Phe Gln Asp Ile Leu Met Asp His Asn
225                 230                 235                 240
```

```
Arg Lys Ser Asn Val Ile Ile Met Cys Gly Gly Pro Glu Phe Leu Tyr
                245                 250                 255

Lys Leu Lys Gly Asp Arg Ala Val Ala Glu Asp Ile Val Ile Ile Leu
            260                 265                 270

Val Asp Leu Phe Asn Asp Gln Tyr Leu Glu Asp Asn Val Thr Ala Pro
        275                 280                 285

Asp Tyr Met Lys Asn Val Leu Val Leu Thr Leu Ser Pro Gly Asn Ser
    290                 295                 300

Leu Leu Asn Ser Ser Phe Ser Arg Asn Leu Ser Pro Thr Lys Arg Asp
305                 310                 315                 320

Phe Ala Leu Ala Tyr Leu Asn Gly Ile Leu Leu Phe Gly His Met Leu
                325                 330                 335

Lys Ile Phe Leu Glu Asn Gly Glu Asn Ile Thr Thr Pro Lys Phe Ala
            340                 345                 350

His Ala Phe Arg Asn Leu Thr Phe Glu Gly Tyr Asp Gly Pro Val Thr
        355                 360                 365

Leu Asp Asp Trp Gly Asp Val Asp Ser Thr Met Val Leu Leu Tyr Thr
    370                 375                 380

Ser Val Asp Thr Lys Lys Tyr Lys Val Leu Leu Thr Tyr Asp Thr His
385                 390                 395                 400

Val Asn Lys Thr Tyr Pro Val Asp Met Ser Pro Thr Phe Thr Trp Lys
                405                 410                 415

Asn Ser Lys Leu Pro Asn Asp Ile Thr Gly Arg Gly Pro Gln Pro Arg
            420                 425                 430

Val Pro Ile Thr Gln Asn Pro Cys Pro Pro Leu Lys Glu Cys Pro Pro
        435                 440                 445

Cys Ala Ala Pro Asp Leu Ala Gly Ala Pro Ser Val Phe Ile Phe Pro
    450                 455                 460

Pro Lys Ile Lys Asp Val Leu Met Ile Ser Leu Ser Pro Met Val Thr
465                 470                 475                 480

Cys Val Val Val Asp Val Ser Glu Asp Pro Asp Val Gln Ile Ser
                485                 490                 495

Trp Phe Val Asn Asn Val Glu Val His Thr Ala Gln Thr Gln Thr His
            500                 505                 510

Arg Glu Asp Tyr Asn Ser Thr Leu Arg Val Val Ser Ala Leu Pro Ile
        515                 520                 525

Gln His Gln Asp Trp Met Ser Gly Lys Ala Phe Lys Cys Lys Val Asn
    530                 535                 540

Asn Arg Ala Leu Pro Ser Pro Ile Glu Lys Thr Ile Ser Lys Pro Arg
545                 550                 555                 560

Gly Pro Val Arg Ala Pro Gln Val Tyr Val Leu Pro Pro Ala Glu
                565                 570                 575

Glu Met Thr Lys Lys Glu Phe Ser Leu Thr Cys Met Ile Thr Gly Phe
            580                 585                 590

Leu Pro Ala Glu Ile Ala Val Asp Trp Thr Ser Asn Gly Arg Thr Glu
        595                 600                 605

Gln Asn Tyr Lys Asn Thr Ala Thr Val Leu Asp Ser Asp Gly Ser Tyr
    610                 615                 620

Phe Met Tyr Ser Lys Leu Arg Val Gln Lys Ser Thr Trp Glu Arg Gly
625                 630                 635                 640

Ser Leu Phe Ala Cys Ser Val Val His Glu Gly Leu His Asn His Leu
                645                 650                 655

Thr Thr Lys Thr Ile Ser Arg Ser Leu Gly Lys
```

<210> SEQ ID NO 49
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cgcggatccc tcaccatgaa gacgttgctg ttggacttgg c                41

<210> SEQ ID NO 50
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgggcactct gggctgaggg ccccggcctg taatatcatt ag               42

<210> SEQ ID NO 51
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
caggccgggg ccctcagccc agagtgccca taacacagaa cccctgtcc        49

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tgctctagat tatttaccca gagaccggga gatggtctta               40

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
acctgtggag ctcttactgg                                       20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
catttcaggt gtcgtgagga                                       20

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
atttaggtga cactatag                                                   18

<210> SEQ ID NO 56
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gttttcccag tcacgac                                                    17

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aacagctatg accatg                                                     16

<210> SEQ ID NO 58
<211> LENGTH: 8
<212> TYPE: PRT
<213> ORGANISM: Mus sp.

<400> SEQUENCE: 58

Pro Arg Val Pro Ile Thr Glu Asn
1               5

<210> SEQ ID NO 59
<211> LENGTH: 4
<212> TYPE: PRT
<213> ORGANISM: Mus sp.

<400> SEQUENCE: 59

Leu Leu Gly Gly
1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Ala Gly Ala
1

<210> SEQ ID NO 61
<211> LENGTH: 4

```
<212> TYPE: PRT
<213> ORGANISM: Mus sp.

<400> SEQUENCE: 61

Lys Lys Gly Gly
1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Ala Gly Ala
1

<210> SEQ ID NO 63
<211> LENGTH: 5
<212> TYPE: PRT
<213> ORGANISM: Mus sp.

<400> SEQUENCE: 63

Glu Phe Lys Cys Lys
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Phe Lys Cys Lys
1               5

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Phe Lys Cys Lys
1

<210> SEQ ID NO 66
<211> LENGTH: 5
<212> TYPE: PRT
<213> ORGANISM: Homo sapiens

<400> SEQUENCE: 66

Gly Arg Gly Pro Gln
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 67

Gly Tyr Tyr Trp Ser
1               5

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Ile Asn His Arg Gly Asn Thr Asn Asp Asn Pro Ser Leu Lys Ser
1               5                   10                  15

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Arg Gly Tyr Thr Tyr Gly Asn Phe Asp His
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Ala Ser Gln Ser Val Ser Arg Asn Leu Ala
1               5                   10

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ala Ser Thr Arg Ala Thr
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Gln Tyr Lys Thr Trp Pro Arg Thr
1               5

<210> SEQ ID NO 73
```

<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ggttactact ggagc                                                      15

<210> SEQ ID NO 74
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gaaatcaatc atcgtggaaa caccaacgac aacccgtccc tcaag                     45

<210> SEQ ID NO 75
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gaacgtggat acacctatgg taactttgac cac                                  33

<210> SEQ ID NO 76
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
agggccagtc agagtgttag cagaaactta gcc                                  33

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ggtgcatcca ccagggccac t                                               21

<210> SEQ ID NO 78
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cagcagtata aaacctggcc tcggacg                                         27

<210> SEQ ID NO 79
<211> LENGTH: 119

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Gln Gln Trp Gly Ala Gly Leu Leu Lys Pro Ser Glu
1               5                   10                  15

Thr Leu Ser Leu Thr Cys Ala Val Phe Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Thr Asn Asp Asn Pro Ser Leu Lys
    50                  55                  60

Ser Arg Val Thr Ile Ser Val Asp Thr Ser Lys Asn Gln Phe Ala Leu
65                  70                  75                  80

Lys Leu Ser Ser Val Thr Ala Ala Asp Thr Ala Val Tyr Tyr Cys Ala
                85                  90                  95

Arg Glu Arg Gly Tyr Thr Tyr Gly Asn Phe Asp His Trp Gly Gln Gly
            100                 105                 110

Thr Leu Val Thr Val Ser Ser
        115

<210> SEQ ID NO 80
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Thr Phe Gly Gln Gly Thr Asn Val Glu Ile Lys
            100                 105

<210> SEQ ID NO 81
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
caggtgcagc tacagcagtg gggcgcagga ctgttgaagc cttcggagac cctgtccctc      60
acctgcgctg tctttggtgg gtccttcagt ggttactact ggagctggat ccgccagccc     120
```

```
ccagggaagg ggctggagtg gattggggaa atcaatcatc gtggaaacac caacgacaac    180
ccgtccctca agagtcgagt caccatatca gtagacacgt ccaagaacca gttcgccctg    240
aagctgagtt ctgtgaccgc cgcggacacg gctgtttatt actgtgcgag agaacgtgga    300
tacacctatg gtaactttga ccactggggc cagggaaccc tggtcaccgt ctcctca      357

<210> SEQ ID NO 82
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
gaaatagtga tgacgcagtc tccagccacc ctgtctgtgt ctccagggga aagagccacc     60
ctctcctgca gggccagtca gagtgttagc agaaacttag cctggtatca gcagaaacct    120
ggccaggctc ccaggctcct catctatggt gcatccacca gggccactgg aatcccagcc    180
aggttcagtg gcagtgggtc tgggacagag ttcactctca ccatcggcag cctgcagtct    240
gaagattttg cagtttatta ctgtcagcag tataaaacct ggcctcggac gttcggccaa    300
gggaccaacg tggaaatcaa a                                              321

<210> SEQ ID NO 83
<211> LENGTH: 1444
<212> TYPE: DNA
<213> ORGANISM: Homo sapiens

<400> SEQUENCE: 83
gaattcctca ccatgggatg gagctgtatc atcctcttct tggtagcaac agctacaggt     60
gtccactccc aggtgcagct acagcagtgg ggcgcaggac tgttgaagcc ttcggagacc    120
ctgtccctca cctgcgctgt ctttggtggg tctttcagtg gttactactg gagctggatc    180
cgccagcccc cagggaaggg gctggagtgg attggggaaa tcaatcatcg tggaaacacc    240
aacgacaacc cgtccctcaa gagtcgagtc accatatcag tagacacgtc caagaaccag    300
ttcgccctga agctgagttc tgtgaccgcc gcggacacgg ctgtttatta ctgtgcgaga    360
gaacgtggat acacctatgg taactttgac cactggggcc agggaaccct ggtcaccgtc    420
agctcagcct ccaccaaggg cccatcggtc ttccccctgg cacctcctc caagagcacc    480 tctgggggca gcgcccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacaca tgcccaccgt gcccagcacc tgaactcctg    780
gggggaccgt cagtcttcct cttccccca aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgtgt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
```

-continued

```
gacatcgccg tggagtggga gagcaatggg cagccggaga acaactacaa gaccacgcct    1260
cccgtgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga agagcctctc cctgtctccg ggtaaataat agggataaca ggtaatact     1440 agag                                                                 1444

<210> SEQ ID NO 84
<211> LENGTH: 468
<212> TYPE: PRT
<213> ORGANISM: Homo sapiens

<400> SEQUENCE: 84
```

Met Gly Trp Ser Cys Ile Ile Leu Phe Leu Val Ala Thr Ala Thr Gly
1               5                   10                  15

Val His Ser Gln Val Gln Leu Gln Gln Trp Gly Ala Gly Leu Leu Lys
                20                  25                  30

Pro Ser Glu Thr Leu Ser Leu Thr Cys Ala Val Phe Gly Gly Ser Phe
            35                  40                  45

Ser Gly Tyr Tyr Trp Ser Trp Ile Arg Gln Pro Pro Gly Lys Gly Leu
        50                  55                  60

Glu Trp Ile Gly Glu Ile Asn His Arg Gly Asn Thr Asn Asp Asn Pro
65                  70                  75                  80

Ser Leu Lys Ser Arg Val Thr Ile Ser Val Asp Thr Ser Lys Asn Gln
                85                  90                  95

Phe Ala Leu Lys Leu Ser Ser Val Thr Ala Ala Asp Thr Ala Val Tyr
            100                 105                 110

Tyr Cys Ala Arg Glu Arg Gly Tyr Thr Tyr Gly Asn Phe Asp His Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn

```
            325                 330                 335
Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 85
<211> LENGTH: 722
<212> TYPE: DNA
<213> ORGANISM: Homo sapiens

<400> SEQUENCE: 85
gcggccgcct caccatggga tggagctgta tcatcctctt cttggtagca acagctacag      60
gtgtccactc cgaaatagtg atgacgcagt ctccagccac cctgtctgtg tctccagggg     120
aaagagccac cctctcctgc agggccagtc agagtgttag cagaaactta gcctggtatc     180
agcagaaacc tggccaggct cccaggctcc tcatctatgg tgcatccacc agggccactg     240
gaatcccagc caggttcagt ggcagtgggt ctgggacaga gttcactctc accatcggca     300
gcctgcagtc tgaagatttt gcagtttatt actgtcagca gtataaaacc tggcctcgga     360
cgttcggcca agggaccaac gtggaaatca aacgtacggt ggctgcacca tctgtcttca     420
tcttcccgcc atctgatgag cagttgaaat ctggaactgc ctctgttgtg tgcctgctga     480
ataacttcta tcccagagag gccaaagtac agtggaaggt ggataacgcc tccaatcgg     540 gtaactccca ggagagtgtc acagagcagg acagcaagga cagcacctac agcctcagca     600
gcaccctgac cctgagcaaa gcagactacg agaaacacaa agtctacgcc tgcgaagtca     660
cccatcaggg cctgagctcg cccgtcacaa agagcttcaa caggggagag tgttagtcta     720
ga                                                                    722

<210> SEQ ID NO 86
<211> LENGTH: 233
<212> TYPE: PRT
<213> ORGANISM: Homo sapiens

<400> SEQUENCE: 86

Met Gly Trp Ser Cys Ile Ile Leu Phe Leu Val Ala Thr Ala Thr Gly
1               5                   10                  15

Val His Ser Glu Ile Val Met Thr Gln Ser Pro Ala Thr Leu Ser Val
            20                  25                  30

Ser Pro Gly Glu Arg Ala Thr Leu Ser Cys Arg Ala Ser Gln Ser Val
            35                  40                  45
```

Ser Arg Asn Leu Ala Trp Tyr Gln Gln Lys Pro Gly Gln Ala Pro Arg
 50                  55                  60

Leu Leu Ile Tyr Gly Ala Ser Thr Arg Ala Thr Gly Ile Pro Ala Arg
 65                  70                  75                  80

Phe Ser Gly Ser Gly Ser Gly Thr Glu Phe Thr Leu Thr Ile Gly Ser
                 85                  90                  95

Leu Gln Ser Glu Asp Phe Ala Val Tyr Tyr Cys Gln Gln Tyr Lys Thr
            100                 105                 110

Trp Pro Arg Thr Phe Gly Gln Gly Thr Asn Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: misc_feature
<222> LOCATION: (1)..(6)
<223> OTHER INFORMATION: Disulfide bond between residues
<220> FEATURE:
<221> NAME/KEY: misc_feature
<222> LOCATION: (2)..(10)
<223> OTHER INFORMATION: Disulfide bond between residues
<220> FEATURE:
<221> NAME/KEY: misc_feature
<222> LOCATION: (5)..(13)
<223> OTHER INFORMATION: Disulfide bond between residues
<220> FEATURE:
<223> OTHER INFORMATION: C-term OH

<400> SEQUENCE: 87

Cys Cys Glu Tyr Cys Cys Asn Pro Ala Cys Thr Gly Cys Tyr
1               5                   10

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: misc_feature
<222> LOCATION: (1)..(6)
<223> OTHER INFORMATION: This sequence may encompass 2, 3, 4, 5, or 6

```
                               residues

<400> SEQUENCE: 88

His His His His His His
1               5

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Phe Leu Gly
1
```